US008252846B2

(12) United States Patent
Murthy et al.

(10) Patent No.: US 8,252,846 B2
(45) Date of Patent: *Aug. 28, 2012

(54) STRATEGIES FOR DELIVERY OF ACTIVE AGENTS USING MICELLES AND PARTICLES

(75) Inventors: Niren Murthy, Atlanta, GA (US); Bali Pulendran, Alpharetta, GA (US); Robert H. Pierce, Palo Alto, CA (US); Michael John Heffernan, Atlanta, GA (US); Jihua Hao, Cleveland, OH (US); Marcin Kwissa, Atlanta, GA (US); Michael Davis, Atlanta, GA (US); Stephen C. Yang, Mableton, GA (US)

(73) Assignees: Emory University, Atlanta, GA (US); Georgia Tech Research Corporation, Atlanta, GA (US); University of Rochester, Rochester, NY (US)

( * ) Notice: Subject to any disclaimer, the term of this patent is extended or adjusted under 35 U.S.C. 154(b) by 378 days.

This patent is subject to a terminal disclaimer.

(21) Appl. No.: 12/075,667

(22) Filed: Mar. 12, 2008

(65) Prior Publication Data
US 2009/0011993 A1    Jan. 8, 2009

Related U.S. Application Data

(63) Continuation-in-part of application No. 11/920,330, filed as application No. PCT/US2006/018182 on May 10, 2006, now abandoned.

(60) Provisional application No. 60/679,480, filed on May 10, 2005, provisional application No. 60/720,099, filed on Sep. 23, 2005.

(51) Int. Cl.
| A61K 47/30 | (2006.01) |
| A61K 38/18 | (2006.01) |
| A61K 31/70 | (2006.01) |
| A61K 47/48 | (2006.01) |
| A01N 43/04 | (2006.01) |
| C08G 2/00 | (2006.01) |

(52) U.S. Cl. ....... 514/772.3; 514/7.6; 514/23; 525/54.1; 525/54.2; 528/220

(58) Field of Classification Search ........................ None
See application file for complete search history.

(56) References Cited

U.S. PATENT DOCUMENTS
4,765,973 A * 8/1988 Heller ........................... 424/486

FOREIGN PATENT DOCUMENTS
WO    WO 2005023294 A2 *    3/2005

OTHER PUBLICATIONS

St. Pierre et al., (J Bioactive and Compatible Polymers. 1997;2(1):1-30).*
Darain et al., (Biosens Bioelectron. Nov. 1, 2004;20(4):857-63, Abstract Only).*

* cited by examiner

*Primary Examiner* — Cherie M Woodward
(74) *Attorney, Agent, or Firm* — Adriano & Associates

(57) ABSTRACT

The present invention provides biodegradable particles (e.g., three-dimensional particles) and micelles which can be used to encapsulate active agents for delivering to a subject. The present invention further provides methods for producing and delivering such particles and micelles. Additionally, the invention provides vaccination strategies that encompass the use of the novel particles and micelles.

12 Claims, 62 Drawing Sheets

(1) Cyclohexane-dimethanol used in food packaging
(2) Acetone metabolic product of lipids
(3) PCADK Mw = 6,000, PD 1.5
(4) Yield 30-40%

Step 1. Combine "oil phase" and "water phase".

Step 2. Sonicate to form microscopic droplets.

Step 3. Evaporate CHCl₃ to encapsulate drug in particles.

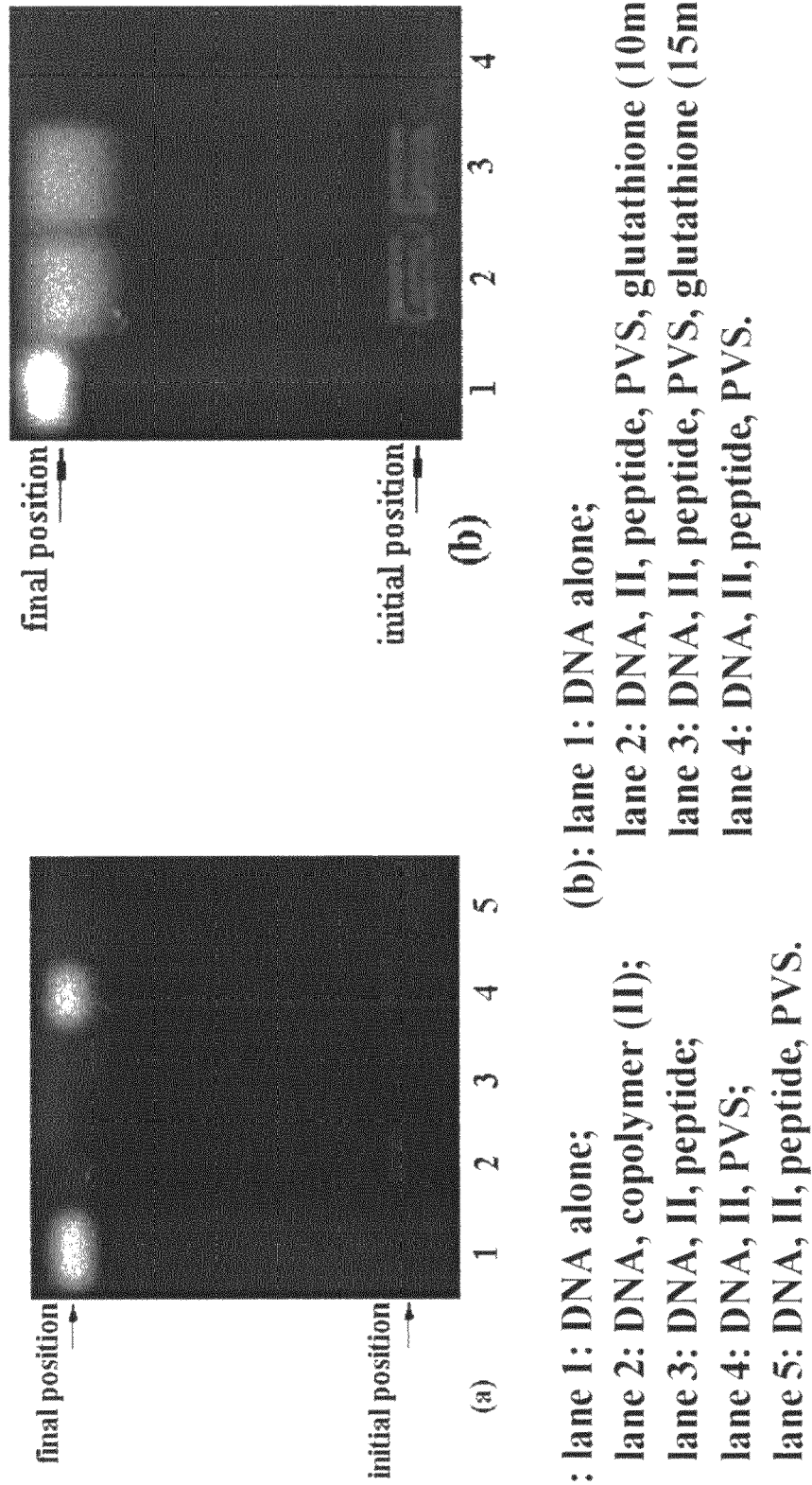

lane 1: DNA alone;

lane 2: DNA, Serum;

lane 3: DNA, II, peptide, GSH, Serum.

PEG-poly(Lysine-Thio-Pyridyl):

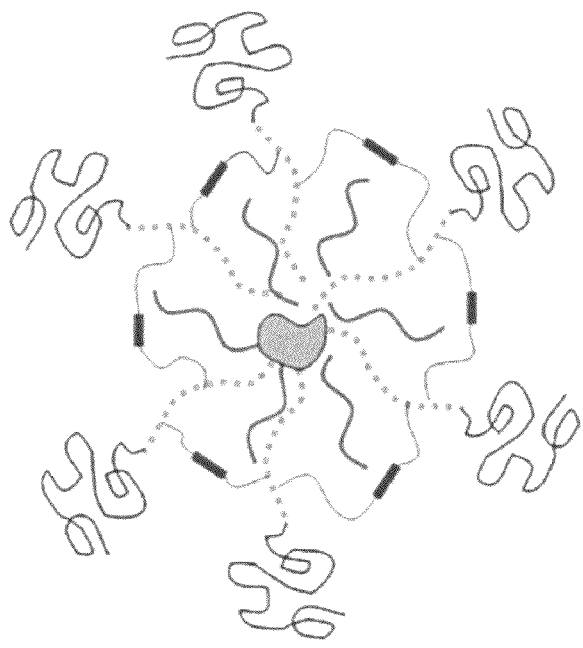
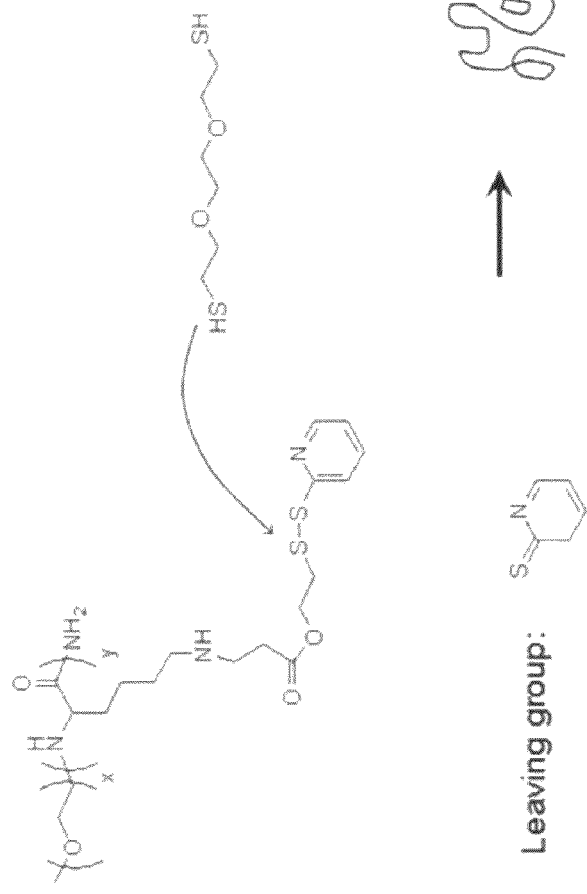
FIG. 11C

FIG. 12B
1. SIINFEKL-CFSE
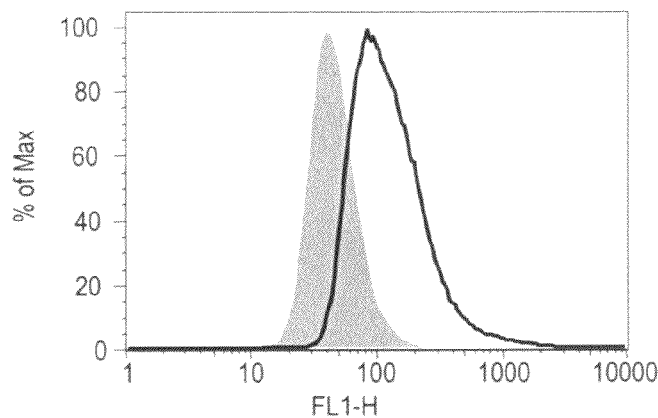
2. SIINFEKL-CFSE micelle 213.2
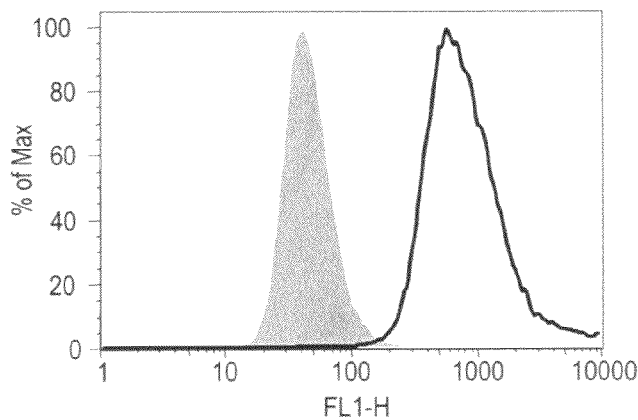
3. SIINFEKL-CFSE micelle 213.3
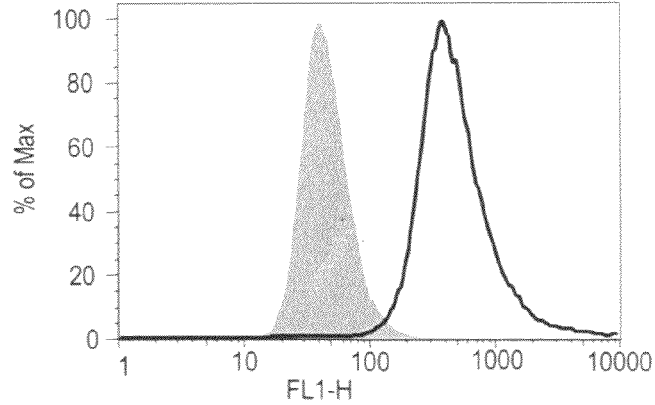

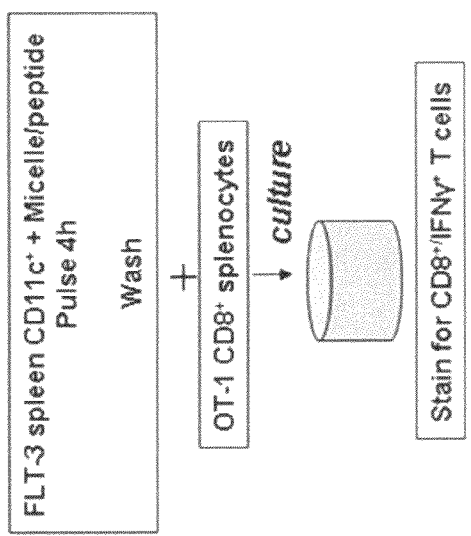
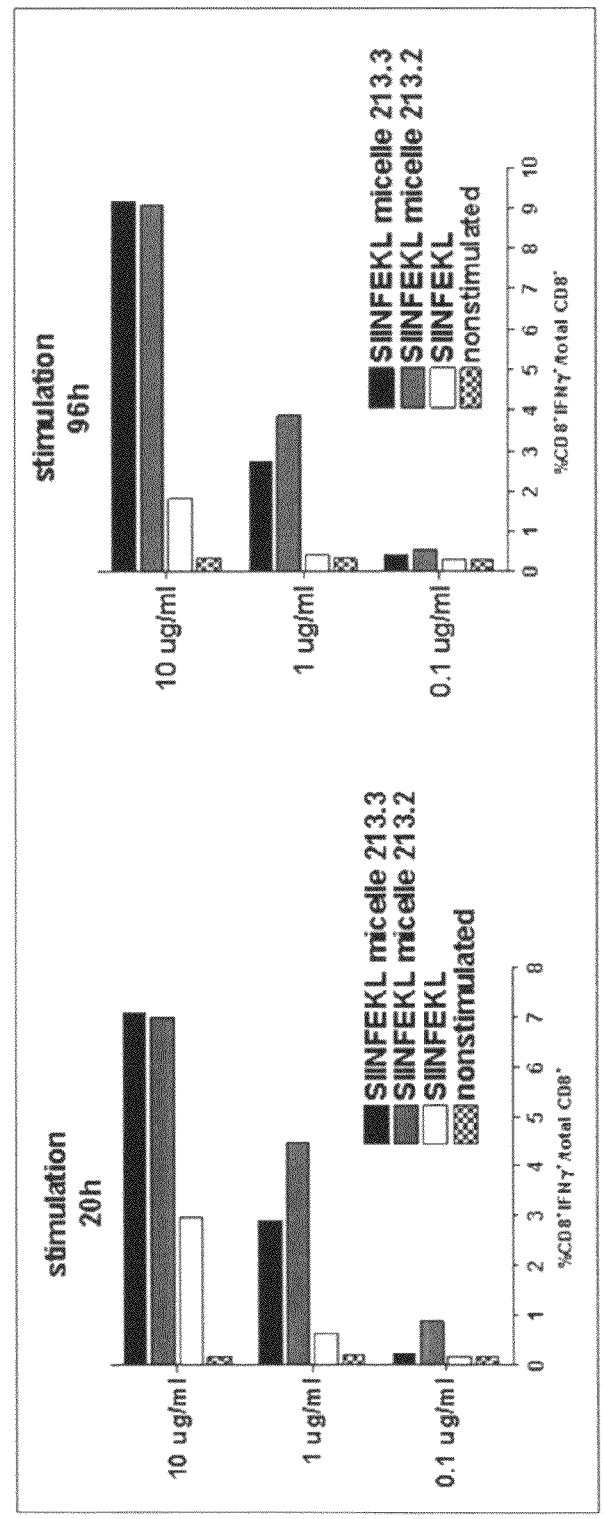
FIG. 13

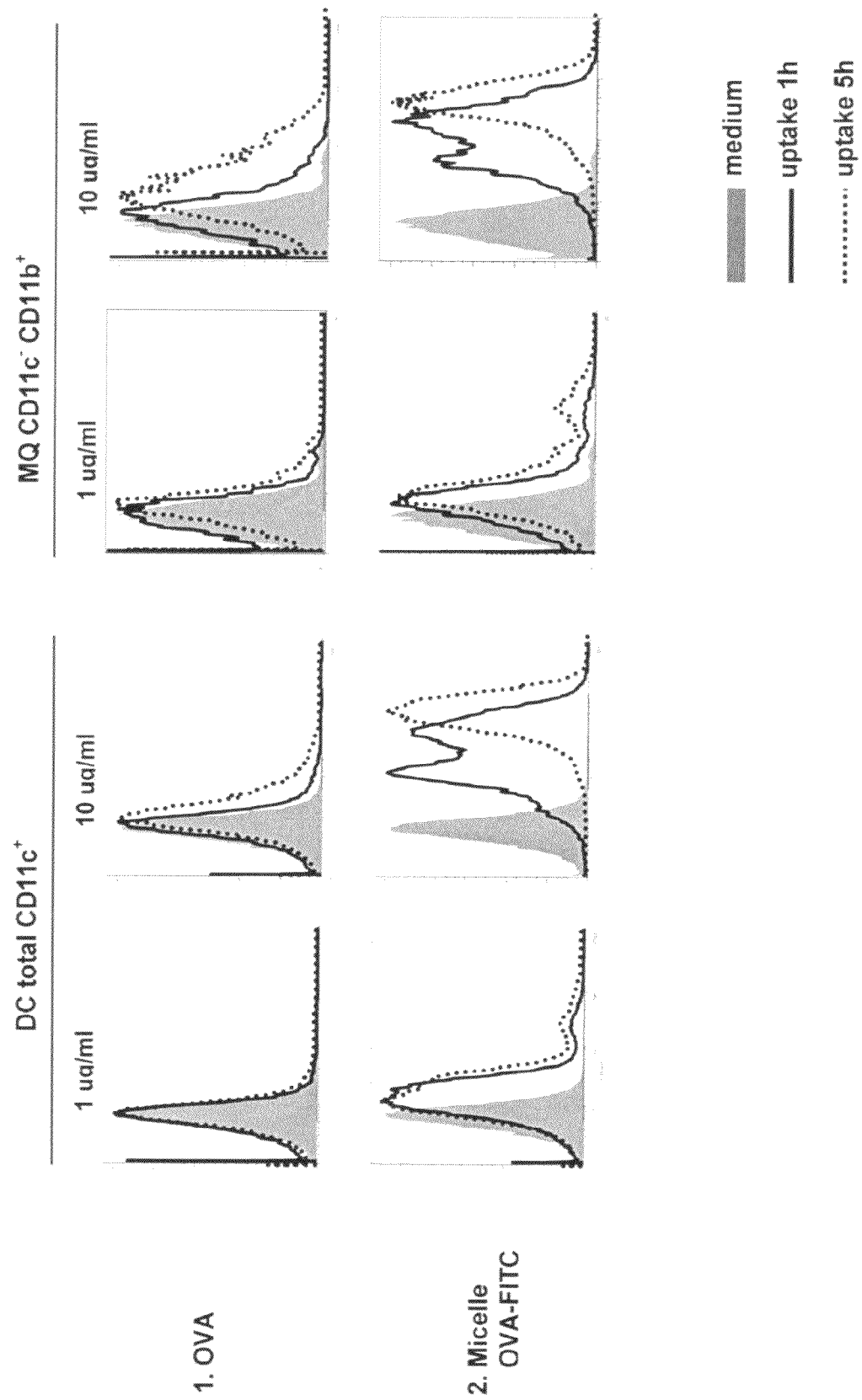

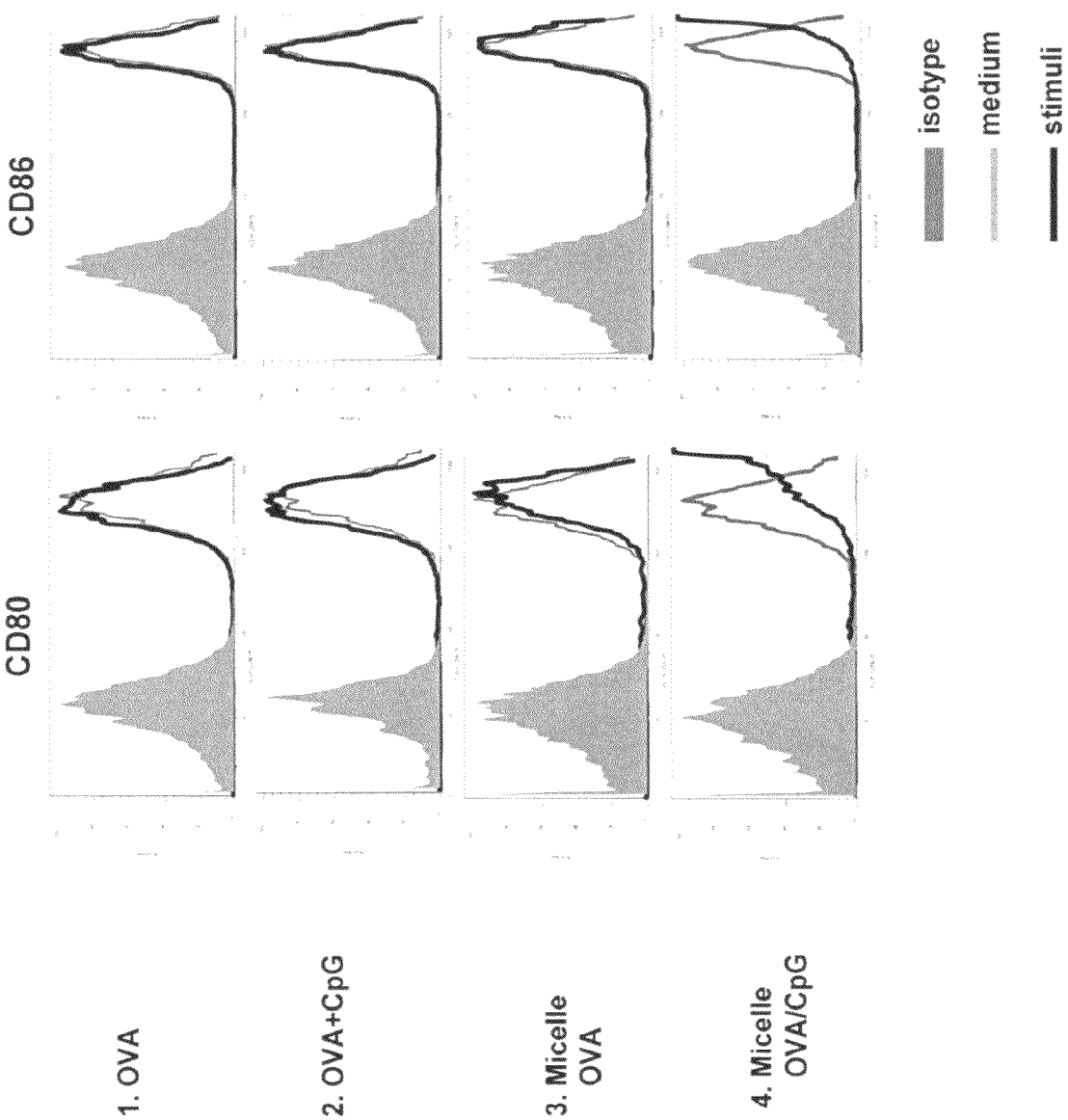

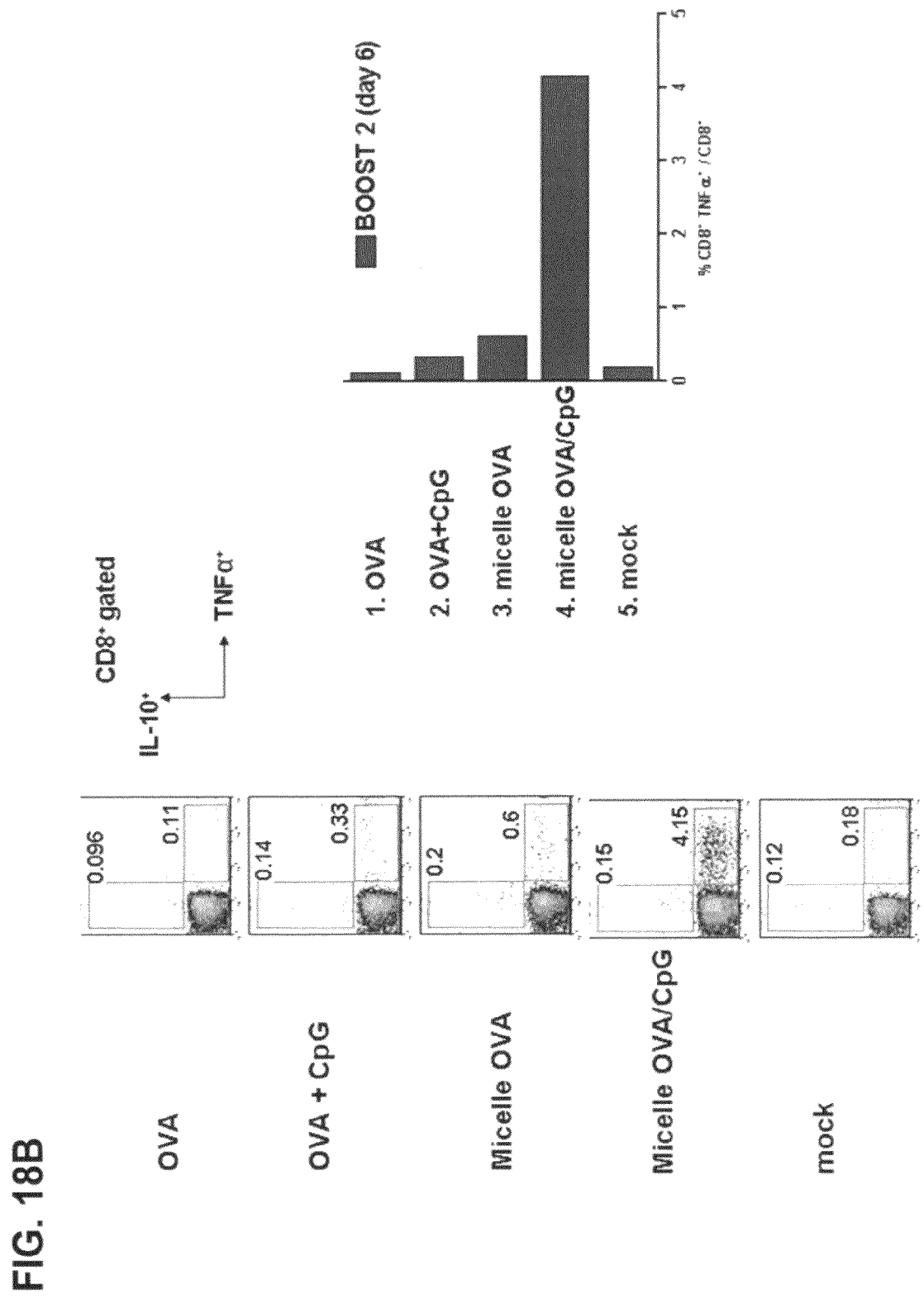

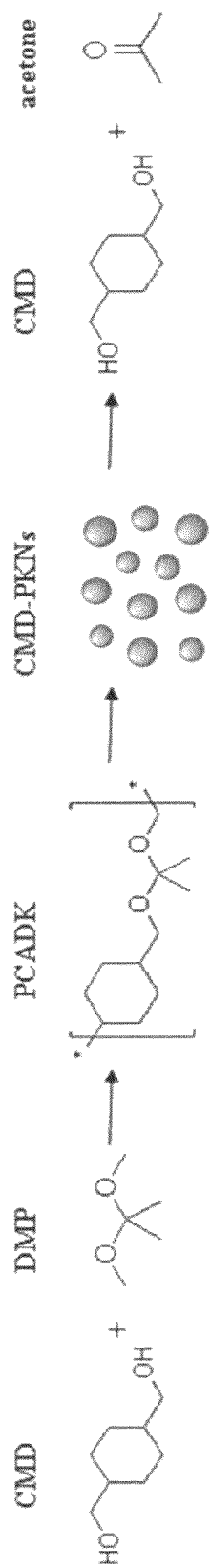
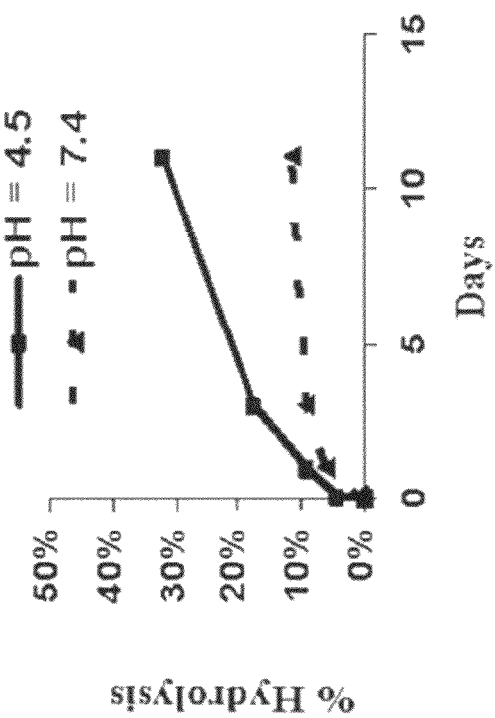
FIG. 19A
FIG. 19B

FIG. 20
SEM Images of PCADK-particles
(using sonication)
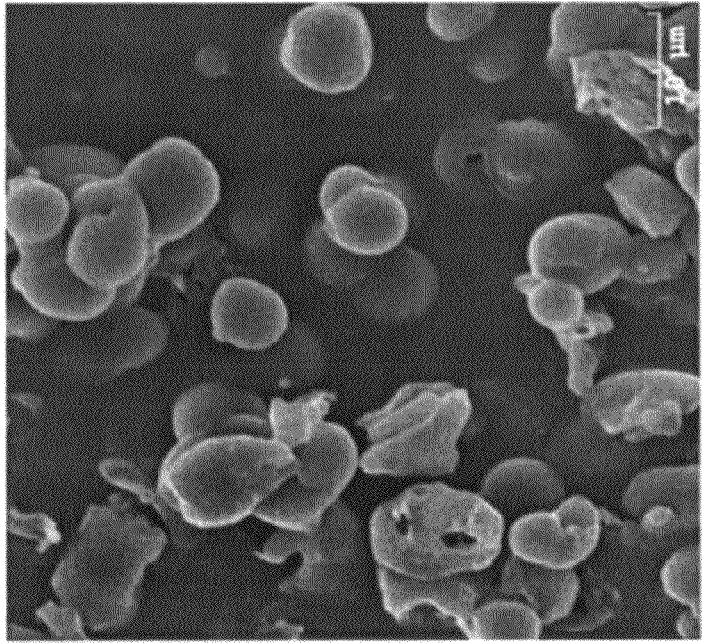
Ebselen
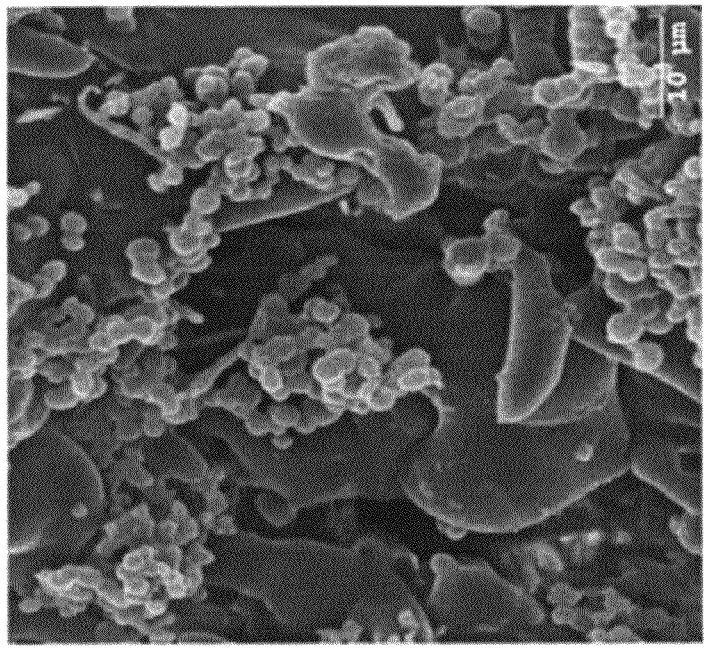
Rhodhamine

FIG. 27

Nanoparticles Formed with PCADK (using sonication)

- Nanoparticles formed by Solvent Evaporation (Single Emulsion)

| Batch | Polymer (mg) | PVA (mg) | CH₃Cl (ul) | Buffer (ml) | Effective Diameter (nm) |
|---|---|---|---|---|---|
| 1 | 20 | 10 | 500 | 5 | 361.3 |
| 2 | 40 | 10 | 500 | 5 | 367.8 |
| 3 | 10 | 10 | 500 | 5 | 307.8 |
| 4 | 20 | 5 | 500 | 5 | 457.5 |
| 5 | 20 | 20 | 500 | 5 | 307.4 |
| 6 | 20 | 10 | 250 | 5 | 331.2 |
| 7 | 20 | 10 | 1000 | 5 | 378.2 |

- Conclusion: Particles formed are in 200-300nm range

Synthesis of polyketal copolymers from 1,4-cyclohexanedimethanol, a second diol and 2,2-dimethoxypropane.

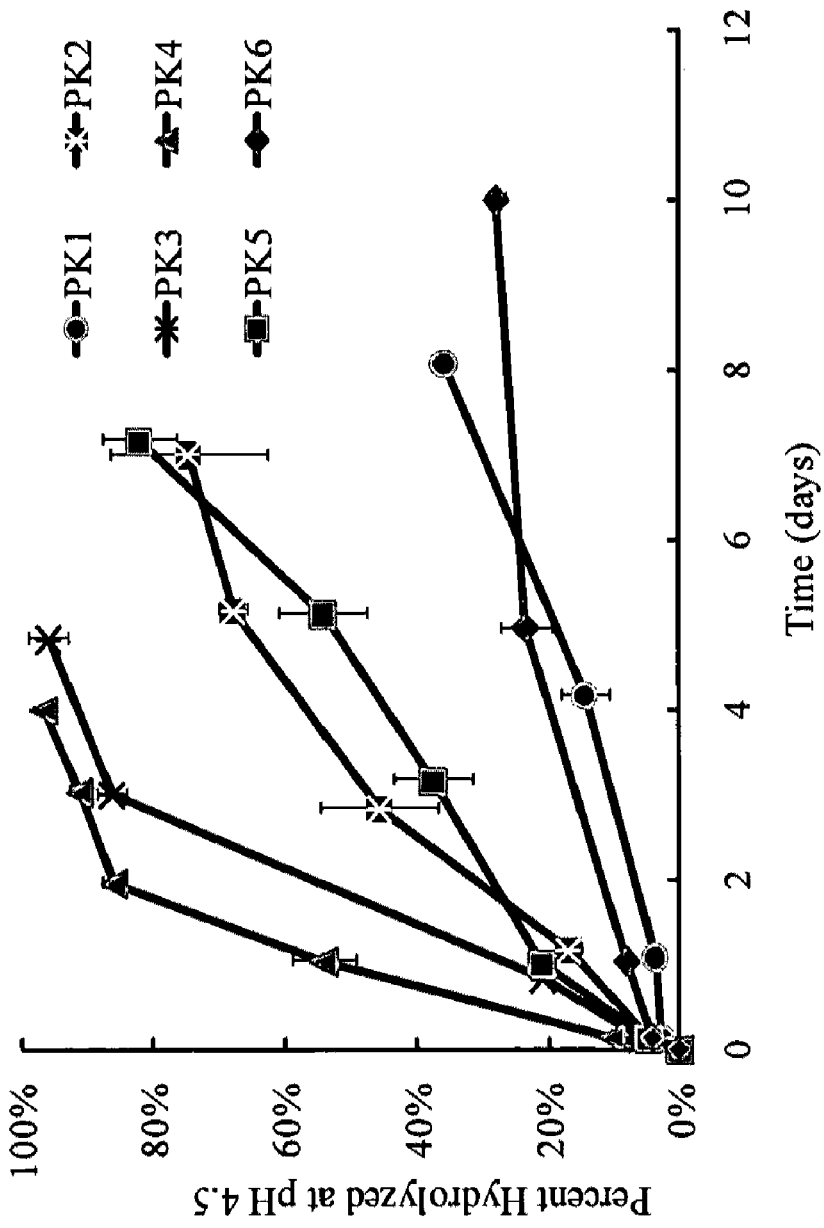

Hydrolysis kinetics of polyketals can be tuned by copolymerization. (A) Hydrolysis profiles of polyketal copolymers PK1 to PK6 in pH 4.5 buffer, and (B) hydrolysis profiles of PK1 to PK6 in pH 7.4 buffer.

SEM images of particles formulated with PK3. SEM image of empty
particles formulated via double emulsion procedures.

SEM micrographs of 10% NTA PCADK microparticles.

SEM micrographs of 10% NTA PCADK microparticles.

SEQUENCE LISTING

```
<160> NUMBER OF SEQ ID NOS: 6

<210> SEQ ID NO 1
<211> LENGTH: 8
<212> TYPE: PRT
<213> ORGANISM: Artificial Sequence
<220> FEATURE:
<223> OTHER INFORMATION: Micelle Encapsulated Peptide
```

```
<400> SEQUENCE: 1

Ser Ile Ile Asn Phe Glu Lys Leu
1               5

<210> SEQ ID NO 2
<211> LENGTH: 14
<212> TYPE: PRT
<213> ORGANISM: Artificial Sequence
<220> FEATURE:
<223> OTHER INFORMATION: Diacylated Lipopeptide

<400> SEQUENCE: 2

Cys Gly Asn Asn Asp Glu Ser Asn Ile Ser Phe Lys Glu Lys
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Diacylated Lipopeptide

<400> SEQUENCE: 3

Cys Gly Asn Asn Asp Glu Ser Asn Ile Ser Phe Lys Glu Lys Ser Lys
1               5                   10                  15

<210> SEQ ID NO 4
<211> LENGTH: 22
<212> TYPE: PRT
<213> ORGANISM: Artificial Sequence
<220> FEATURE:
<223> OTHER INFORMATION: HIV peptide

<400> SEQUENCE: 4

Cys Gly Cys Arg Ile Gln Arg Gly Pro Gly Arg Ala Phe Val Thr Ile
1               5                   10                  15

Gly Lys Cys Gly Cys Gly
            20

<210> SEQ ID NO 5
<211> LENGTH: 15
<212> TYPE: PRT
<213> ORGANISM: Artificial Sequence
<220> FEATURE:
<223> OTHER INFORMATION: GP-120 protein

<400> SEQUENCE: 5

Arg Ile Gln Arg Gly Pro Gly Arg Ala Phe Val Thr Ile Gly Lys
1               5                   10                  15

<210> SEQ ID NO 6
<211> LENGTH: 20
<212> TYPE: DNA
<213> ORGANISM: Artificial Sequence
<220> FEATURE:
<223> OTHER INFORMATION: ISS DNA

<400> SEQUENCE: 6
tccatgacgt tcctgacgtt                                               20
```

STRATEGIES FOR DELIVERY OF ACTIVE AGENTS USING MICELLES AND PARTICLES

Throughout this application various publications are referenced. The disclosures of these publications in their entireties are hereby incorporated by reference into this application in order to more fully describe the state of the art to which this invention pertains.

This application is a continuation-in-part of U.S. application U.S. Ser. No. 11/920,330 filed Nov. 9, 2007, which claims the benefit of international application PCT/US2006/018182 which claims the benefit of U.S. provisional applications U.S. Ser. No. 60/679,480 filed May 10, 2005 and U.S. Ser. No. 60/720,099 filed Sep. 23, 2005, which are incorporated herein in full by reference.

This invention was made with government support under NIH/NIAID grant AI048638, AI0564499, AI056947, AI057157, AI05726601, and NIH/NIDDK grant DK057665. The government has certain rights in the invention.

FIELD OF THE INVENTION

The invention relates to particle and micelle based strategies for delivering active agents, such as (i) vaccines; (ii) immune modulatory agents, (including TLR ligands or synthetic molecules, which modulate the function of innate immune cells such as dendritic cells, or synthetic molecules or siRNA that modulate signaling networks within cells (e.g., dendritic or other antigen presenting cells) and/or; (iii) drugs that target antigen-presenting cells so as to modulate innate and adaptive immunity, in a therapeutic or prophylactic setting.

BACKGROUND OF THE INVENTION

Harnessing Innate Immunity for Vaccination

A hallmark of the immune system is its ability to launch qualitatively different types of immune responses. Thus for example, T-helper 1 (or Th1) immune responses stimulate cytotoxic "killer" T cells, which kill virally infected cells or tumors. In contrast, T-helper 2 (or Th2) responses are associated with antibody production, particularly secretion of IgE antibodies, which confer protection against extracellular parasites or bacteria or toxins. Furthermore, T regulatory responses can suppress over exuberant immune responses, and thus limit the immune pathology caused by allergies, autoimmunity, transplant rejection, or sepsis like symptoms. Given the existence of such diverse types of immune responses, and their differential roles in conferring effective protection against viruses, tumors, extracellular parasites and bacteria, and in regulating deleterious immune responses in allergies, autoimmunity, transplantation and sepsis, a "rosetta stone" of modern immunology is to learn how to induce optimally effective immune responses in various clinical settings.

In this context, recent advances in immunology have revealed a fundamental role for the innate immune system in controlling both the quality and quantity of immune responses (Pulendran & Ahmed, Cell, 2006, 124:849-863). Thus, it has long been known that the immune system is unresponsive to most foreign proteins that are injected in a soluble, deaggregated form, but when injected together with immune-stimulating substances called "adjuvants," these foreign proteins can induce robust immunity. In fact it was known that the nature of the adjuvant is what determines the particular type of immune response that follows, which may be biased towards cytotoxic T-cell responses, antibody responses, or particular classes of T-helper responses (Pulendran, Immunol. Rev., 2004, 199:227-250; Pulendran, J. Immunol., 2005, 175:2457-2465; Pulendran & Ahmed, Cell, 2006, 124:849-863). Despite the importance of adjuvants, there is only one adjuvant, alum, licensed for clinical use in the United States, and most other experimental adjuvants consist of crude extracts of microbes or bacteria, which induce potent activation of immune cells, but also result in toxicities. Until recently, the mechanism of action of such adjuvants was not understood. However, recent advances in innate immunity have offered a conceptual framework with which to understand how adjuvants function. Central to this issue is a rare but widely distributed network of cells known as dendritic cells (DCs), which constitute an integral component of the innate immune system. DCs, which have been called 'Nature's adjuvants,' express receptors which can recognize components of microbes and viruses. Such receptors include the Toll-like receptors (TLRs), C-type lectins, and CATTERPILLAR proteins, which can "sense" microbial stimuli, and activate DCs and other immune cells (Pulendran, Immunol. Rev., 2004, 199:227-250; Pulendran, J. Immunol., 2005, 175:2457-2465; Pulendran & Ahmed, Cell, 2006, 124: 849-863]. It is now clear that DCs play essential roles in orchestrating the quality and quantity of the immune response.

There are currently some 13 TLRs described in mammals. Activating distinct TLRs on DCs induces qualitatively different types of immune responses (Pulendran, et al, 2001, supra; Dillon et al, 2004, supra; Agrawal et al, J. Immunol., 2003, 171:4984-4989; Dillon et al, J. Clin. Immunol., 2006, 116: 916-928). Thus, activating most TLRs can induce Th1 responses; activating TLR3, 7 or 9 can induce cytotoxic T cells that kill virally infected cells and tumors; and emerging evidence suggests that activating TLR2 induces Th2 responses, (which are associated with antibody responses that offer protection against viruses or extracellular bacteria or parasites), or even T regulatory or tolerogenic responses, (which suppress over exuberant immune responses, and thus offer protection against unbridled immunity in allergies, autoimmunity, sepsis, and transplantation). As such, DCs and TLRs and other recognition receptors, represent attractive immune modulatory targets for vaccinologists and drug developers. Thus learning how to exploit fundamental elements of the innate immune system such as DCs and TLRs, is of paramount importance in the development of novel drugs and vaccines.

An important corollary to this notion is that the vast majority of vaccines which have been developed over the past 200 years, (since the first recorded vaccination trial of Edward Jenner), have been developed empirically. Therefore, despite their successes in controlling various scourges such as smallpox, polio, TB and yellow fever, we have no knowledge of the scientific rationale for how these vaccines stimulate such effective immunity. For example, the yellow fever vaccine 17D [YF-17D] is one of the most effective vaccines known. Since its development more than 65 years ago, it has been administered to over 400 million people globally. Despite its success, the mechanism of its action is not known. Therefore, as stated above, the spectacular advances in innate immunity which have occurred in the last six years or so, offer us a new vision with which to understand the modus operandi of such "gold standard" vaccines, with a view to using such knowledge to devising future vaccines against emerging and re-emerging infections of the 21$^{st}$ century. In this context, our recent findings suggest that the highly effective Yellow Fever Vaccine (YF-17D) is a potent stimulator of DCs, and multiple TLRs, including TLR 2, 7, 8 and 9 (Querec et al., J. Exp.

Med., 2006, 203:413-421). Given, the different types of immune responses triggered by the distinct TLRs (Pulendran et al., 2001, supra; Agrawal et al., J. Immunol., 2003, 171: 4984-4989; Dillon et al, 2004, supra; Dillon et al, J. Clin. Immunol., 2006, 116:916-928), it was tempting to speculate that by activating multiple TLRs, YF-17D was inducing a broad spectrum of immune responses. Indeed, our data suggests that YF-17D triggers a broad spectrum of innate and adaptive immune responses (Th1, Th2, cytotoxic T cells, neutralizing antibody), and that distinct TLRs control different types of this polyvalent immunity (Querec et al., J. Exp. Med., 2006, 203:413-421). Eliciting such a broad spectrum of immune responses is also likely to be beneficial in designing vaccines against other infections, against which no effective vaccines currently exist, such as HIV, HCV, malaria, TB, influenza, anthrax and Ebola, or against tumors. Thus, strategies for designing future vaccines against emerging or re-emerging infections might benefit from incorporating multiple TLR ligands plus antigens, plus immune modulatory agents, in order to induce multi-pronged immune responses. Therefore, an important challenge is the development of delivery systems which are capable of delivering such immune modulatory agents in vivo.

As described herein, polyketal (PK) particles are a new class of biomaterials that hydrolyze in a controllable manner at physiological pH values and degrade into neutral compounds.

Delivery Systems for Novel Vaccines

Drug delivery vehicles based on polyesters and polyanhydrides have been widely used for the sustained release of therapeutics because of their excellent biocompatibility profiles and slow hydrolysis rates (Anderson, J. M. et al., *Adv. Drug Delivery Rev.*, 1997, 28:5-24; Jain, R. A., *Biomaterials*, 2000, 21:2475-2490; Mathiowitz, E. et al., *J. Appl. Polym. Sci.*, 1988, 35:755-774; Berkland, C. et al., *J Controlled Release*, 2004, 94:129-141). However, numerous medical applications, such as targeting the acidic environment of lysosomes and tumors, require drug delivery systems that undergo rapid, pH-sensitive degradation (Stubbs, M. et al., *Mol. Med. Today*, 2000, 6:15-19; Leroux, J.-C., *Adv. Drug Delivery Rev.*, 2004, 56:925-926). The majority of degradable polymers used for drug delivery cannot fulfill this requirement because they are composed of ester linkages, which degrade by base-catalyzed hydrolysis at physiological pH values. Particles made of ester based materials, such as Poly(lactic-glycolic acid) (PLGA), polyorthoesters, and polyanhydrides, all generate high quantities of acid when they degrade. This causes degradation of protein and DNA therapeutics and the degradation also takes weeks to months. Because the life span of mature DCs is around 2 days these materials are not ideal for vaccine development. Recently, pH sensitive hydrophobic microparticles based on poly(orthoesters) and poly(beta-amino esters) have been successfully used for intracellular drug delivery and tumor targeting, thus demonstrating the potential of acid-sensitive biomaterials for drug delivery (Heller, J. et al., *Biomacromolecules*, 2004, 5:1625-1632; Heller, J. et al., *Adv. Drug Delivery Rev.*, 2002, 54:1015-1039; Berry, D. et al., *Chem. Biol.*, 2004, 11:487-498; Potineni, A. et al., *J Controlled Release*, 2003, 86:223-234). Consequently, there is great interest in developing new strategies for the synthesis of pH-sensitive biodegradable polymers.

Vaccines based on recombinant proteins, peptide antigens, or DNA vaccines encoding such vaccine antigens, have tremendous therapeutic potential against infectious diseases and tumors, in which the antigenic epitopes have been defined. Such vaccines have been capable of generating protective immunity against infectious diseases, in animal models, and numerous clinical trials with such vaccines are currently in progress (van Endert, P M, *Biologicals,* 2001, 29:285-8; Purcell, A W et al., *Journal of Peptide Science,* 2003, 9:255-81; Shirai, M. et al., *Journal of Virology,* 1994, 68:3334-42; Hunziker, I P et al., *International Immunology,* 2002, 14:615-26). However, despite their promise, a major challenge concerns the efficient delivery of peptides, proteins, DNA vaccines and adjuvants, so as to target the appropriate type of antigen presenting cell in order to launch an effective immune response. Although promising results have been obtained with peptide vaccines composed of lipid conjugates and PLGA microparticles, there is still a great need for the development of new peptide vaccine delivery vehicles (Ertl, H C J et al., *Vaccine,* 1996, 14:879-85; Jackson, D C et al., *Vaccine,* 1997, 15:1697-705).

SUMMARY OF THE INVENTION

The present invention provides biodegradable particles (e.g., three-dimensional particles) and micelles which can be used to encapsulate active agents for delivering to a subject. The present invention further provides methods for producing and delivering such particles and micelles. Additionally, the invention provides vaccination strategies that encompass the use of the novel particles and micelles.

Hydrophobic Polyketal Particles

The present invention is directed to new type of hydrophobic polymers comprising ketal groups in the polymer backbone wherein the ketal groups are arranged in a way such that both oxygen atoms are located in the polymer backbone.

Further, the ketal polymer can be formed via a ketal exchange reaction between a ketal and a diol. In accordance with the invention, one or more types of the ketals and/or diols can be used for the formation of a homopolymer or copolymer.

Also encompassed by the present invention are polyketal polymers which are joined by other polymers (e.g. PEG, polyesters, polyamides, polysaccharides, polyethers, or polyanhydrides). The resulting polymers can be alternating copolymers, random copolymers, block copolymers, or graft copolymers. Polythioketal polymers, mixed polythio-amine ketals, polythio-hydroxyl ketals and polyhydroxyl-amine ketals are also in the scope of the present invention.

Polyketal polymers of the invention hydrolyze in aqueous solutions into low molecular weight, water soluble alcohols and ketones. The advantage of a ketal linkage in the backbone is that it degrades under acidic conditions of phagosomes, within 1-2 days at pH 5.0. Polyketals can therefore also be used for targeting the acidic environments of tumors, inflammation and phago-lysosomes. The degradation does not generate acidic degradation products. Thus, the ketal polymers are suitable for biological use.

Micelles

The present invention further provides novel biodegradable crosslinked micelles comprising multiple polymers, wherein the polymers are e.g., crosslinked by an external crosslinking agent (i.e., agents which are not introduced into the polymer chain). The advantage of using of external agents is the faster crosslinking reaction compared to a reaction wherein only crosslinkable moieties within the polymer are used. The external crosslinking agent also decreases the chances that the encapsulated is protein destroyed.

Figure 2:
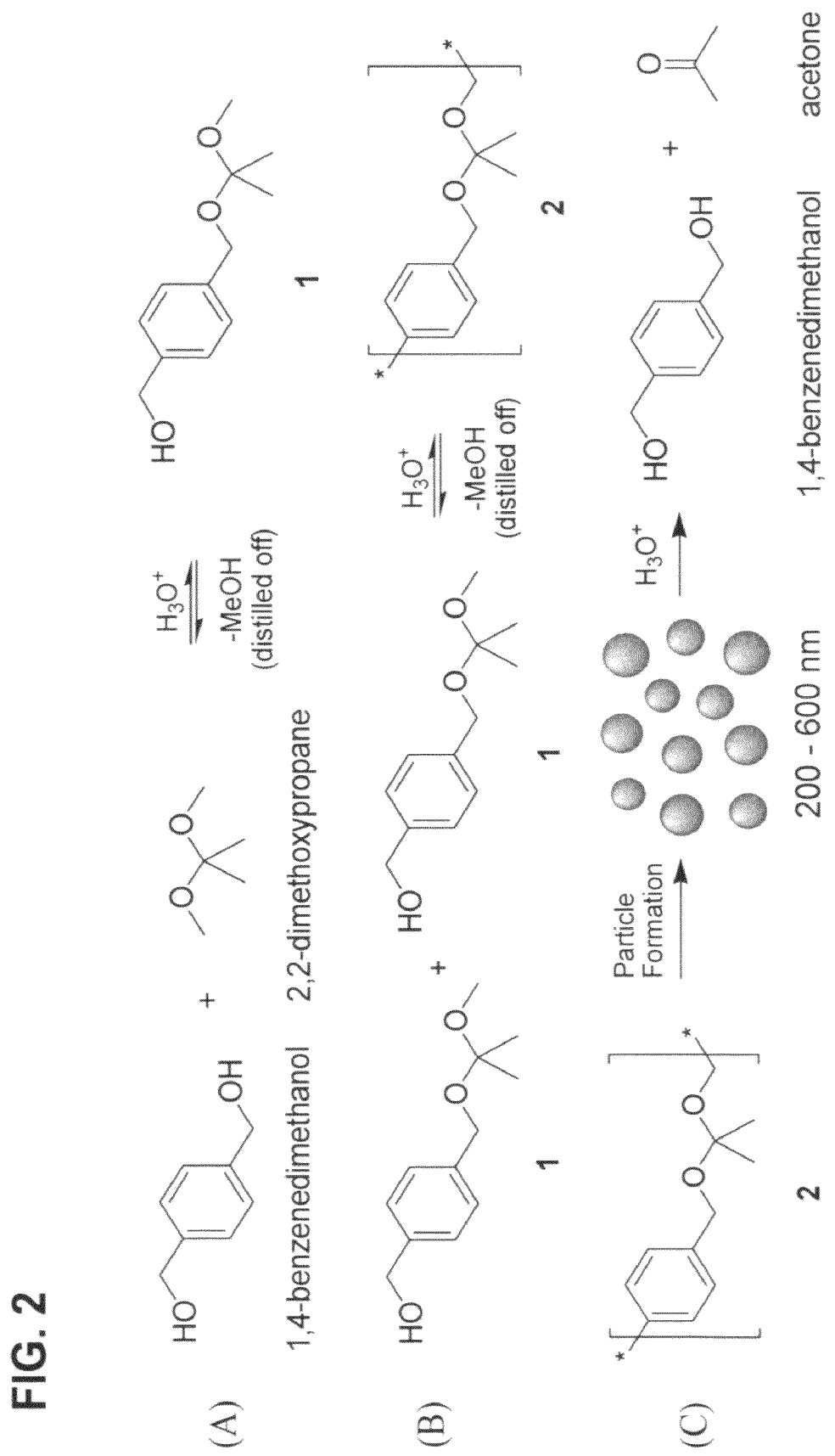

FIG. 2 is a diagrammatic representation showing the synthesis and degradation of Ketal-backbone polymer (polyketal). (A) Ketal exchange reaction between 1,4-benzenedimethanol and 2,2-dimethoxypropane to produce the ketal intermediate 1. (B) Stepwise polymerization of 1 to produce polyketal 2. Reaction steps A and B are driven forward by distilling off the methanol byproduct. (C) Formation of drug-loaded particles by the solvent evaporation method. Particles exhibit pH-sensitive degradation into low molecular weight excretable compounds (Example 4, infra).

Figure 3A:
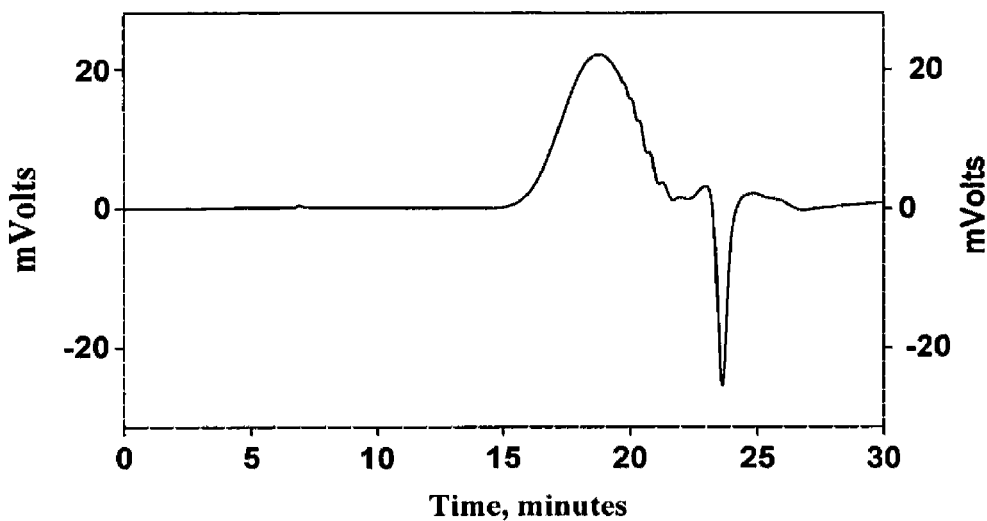
Figure 3B:
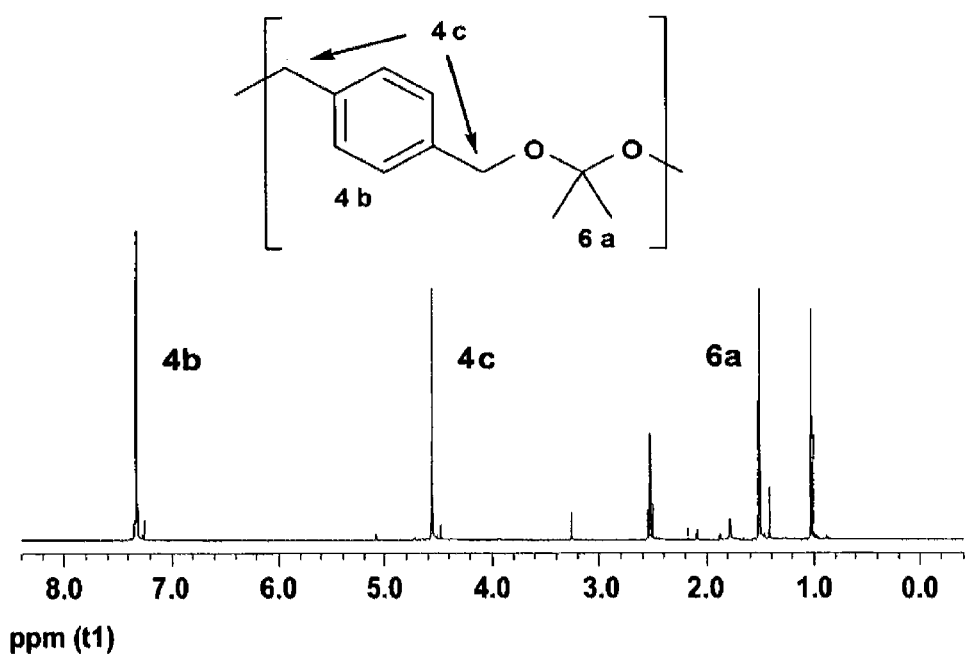

FIG. 3(A) is a graph showing a GPC trace of polyketal 2 (of FIG. 2) in THF (Shimadzu SCL-10A). $M_w$=4000, $M_w/M_n$=1.54 based on a polystyrene standard (Polymer Laboratories, Inc.). Y-axis indicates relative absorbance at 262 nm. FIG. 3(B) shows $^1$H NMR spectrum of polyketal 2 (of FIG. 2) in CDCl$_3$ (Varian Mercury Vx 400); repeating unit peaks at 7.3 ppm (4b), 4.5 ppm (4c), and 1.5 ppm (6a). Peaks at 2.5 and 1.0 are due to triethylamine added to prevent ketal hydrolysis. (Example 4, infra)

Figure 4:
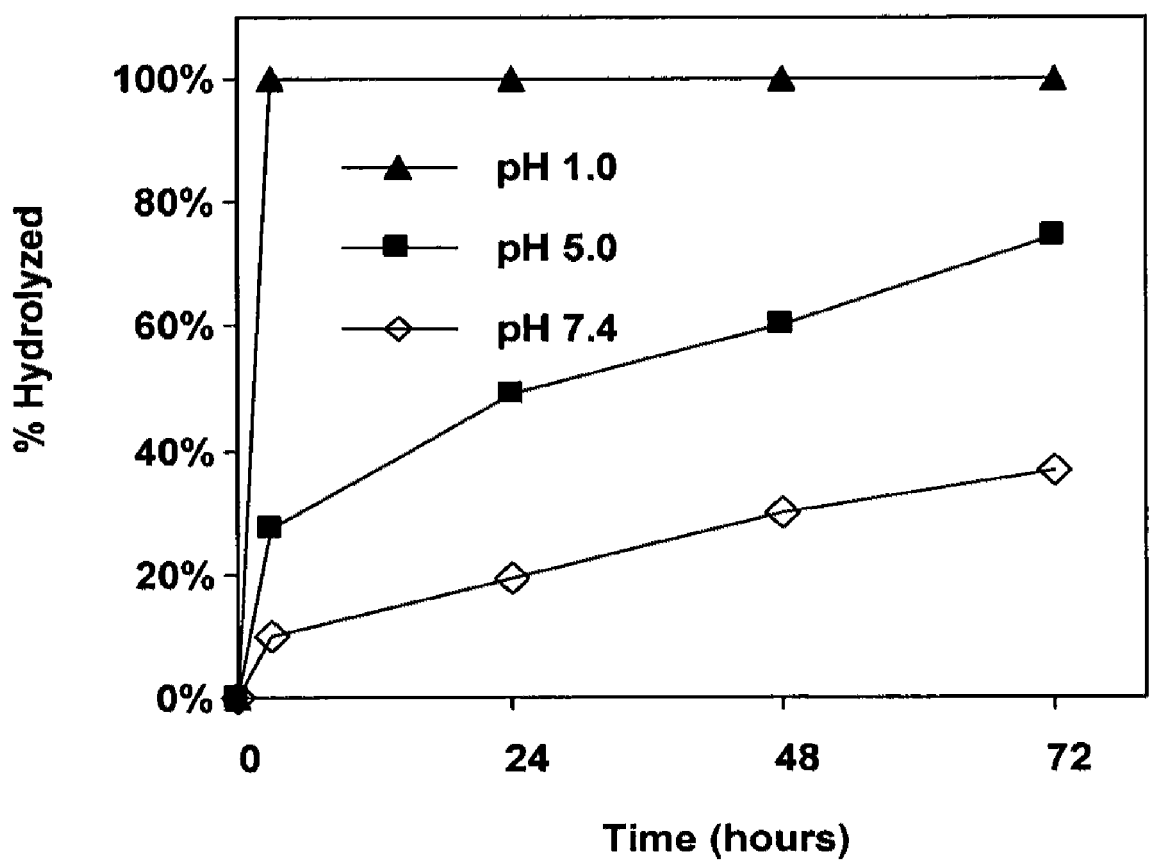

FIG. 4 is a line graph showing the hydrolysis kinetics of polyketal 2 (of FIG. 2) (finely ground powder) at pH 1.0, 5.0, and 7.4. Exponential decay half-lives are 102 h (pH 7.4) and 35 h (pH 5.0). The pH 1.0 control batch was completely hydrolyzed before the first time point. (Example 4, infra)

Figure 5:
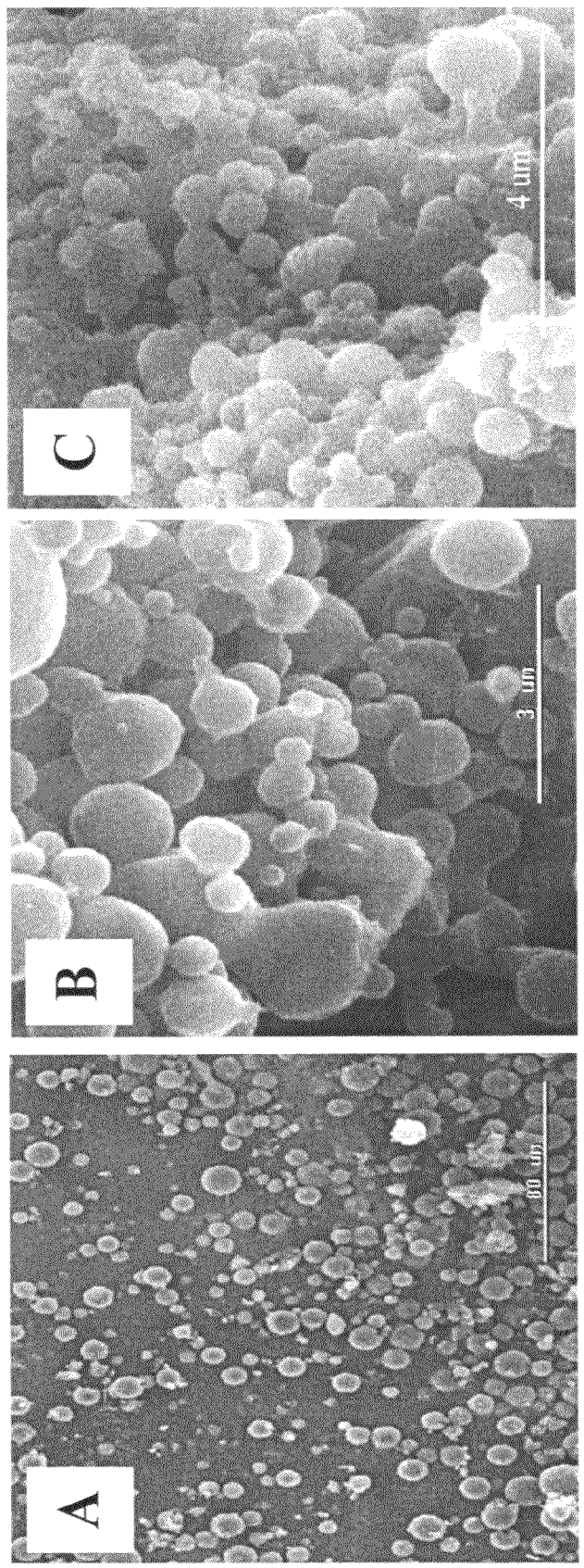

FIG. 5 shows SEM images of particles made with polyketal 2 (of FIG. 2). (A,B) Particles using 0.2:1 ratio of PVA to polyketal 2 (particle size: 0.5-30 µm). (C) Dexamethasone-loaded particles made using 1:1 PVA:polyketal 2 (particle size: 200-500 nm). Scale bars are (A) 80 µm, (B) 3 µm, and (C) 4 µm. (Examples 5 and 6, infra)

Figure 6A:
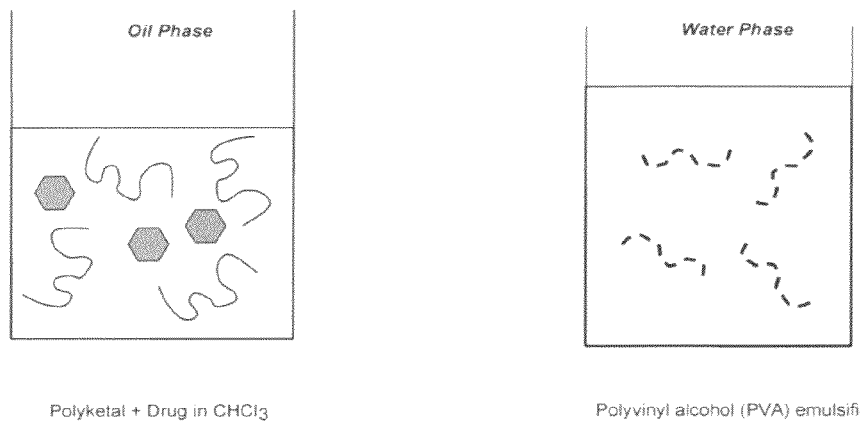
Figure 6B:
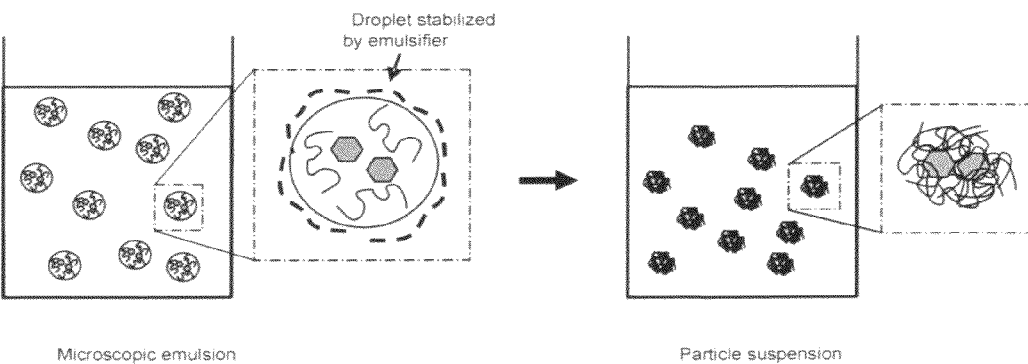

FIG. 6 is a schematic representation showing particle formation. A. Step 1: Dissolve polyketal and drug into chloroform; dissolve polyvinyl alcohol in water. B. Step 2: Add chloroform solution to water and sonicate, generate micron sized droplets. Step 3: Let chloroform evaoporate, generates particles. (Example 6, infra)

Figure 7:
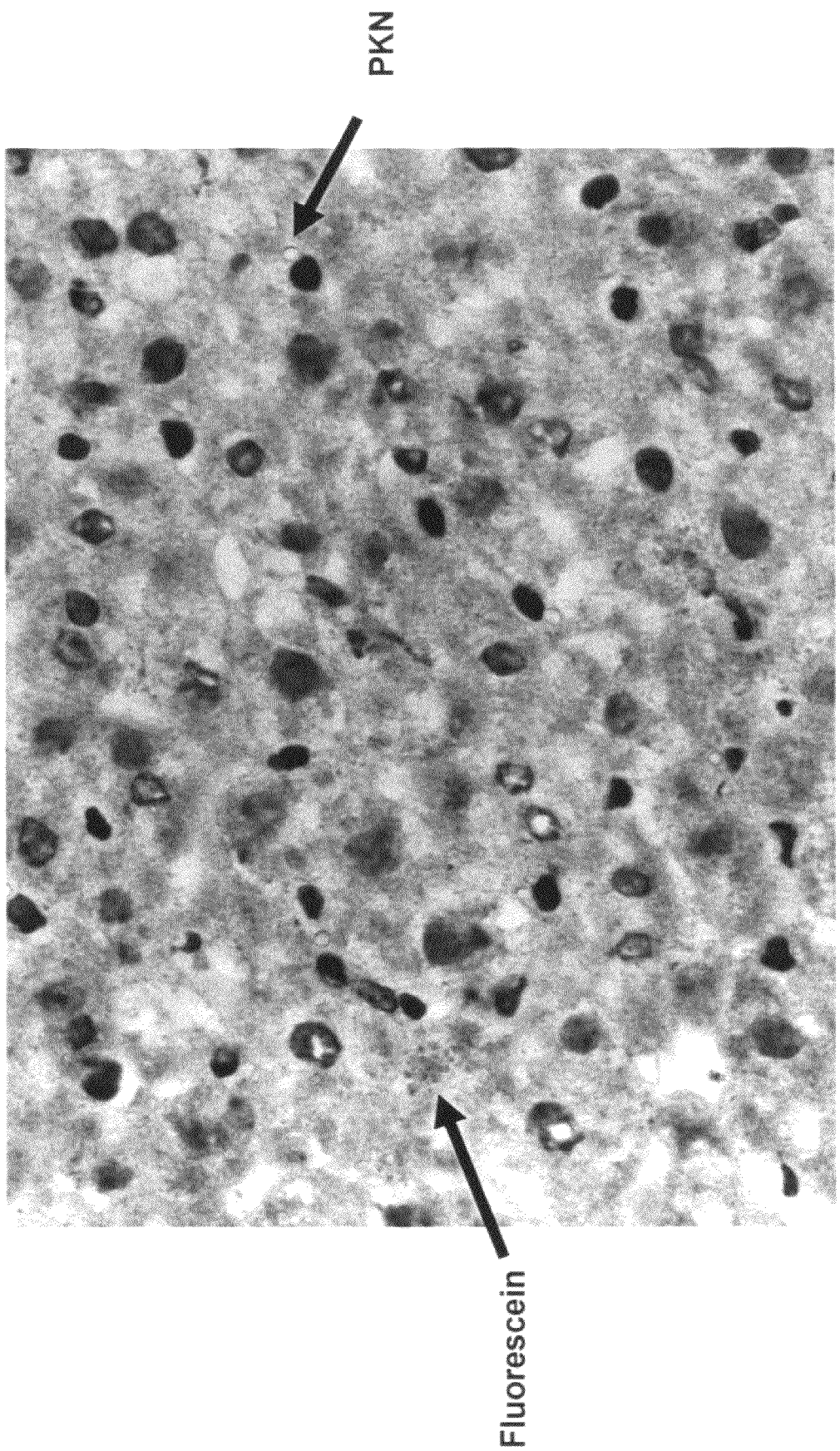

FIG. 7 is a photograph showing polyketal particles loaded with Fluorescein are taken up in the liver. Murine liver tissue slice is shown releaing fluorescein from PKNs following intravenous injection. (Example 6, infra)

Figure 8:
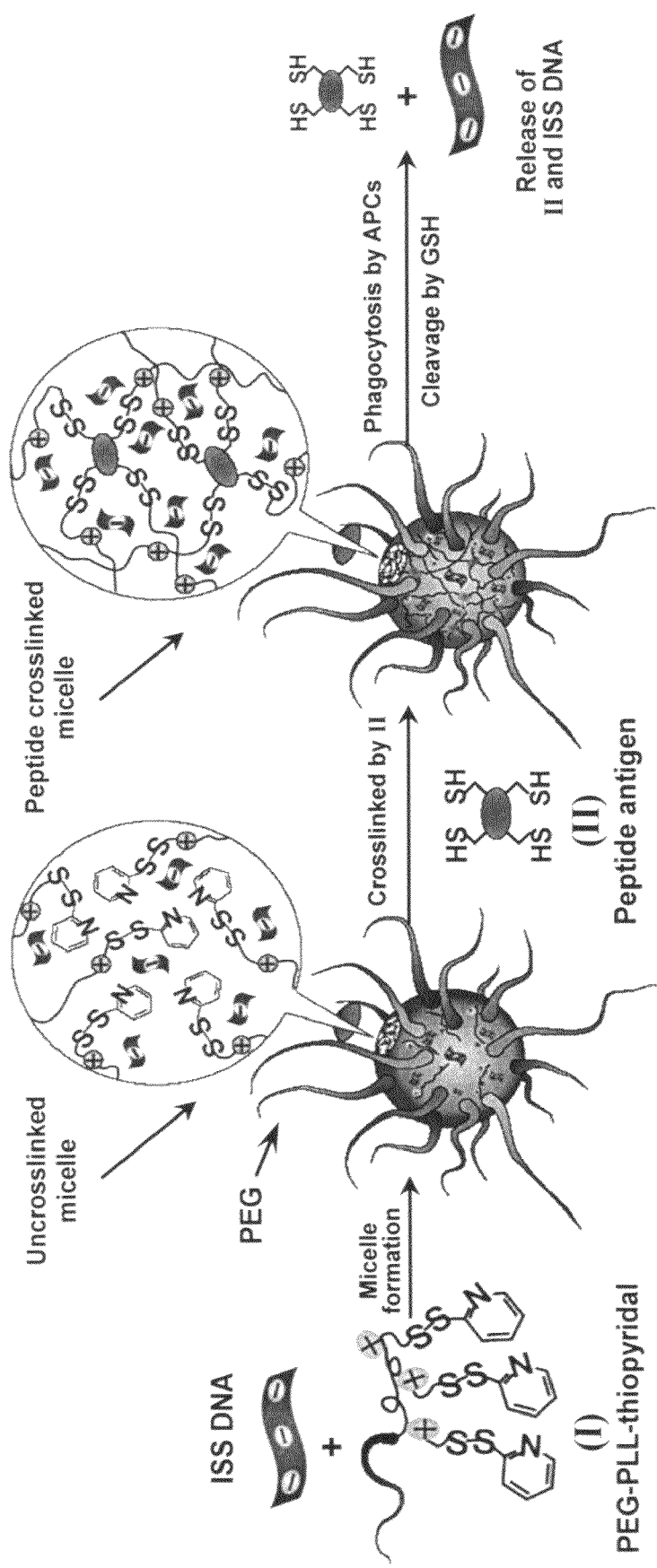
Figure 9A:
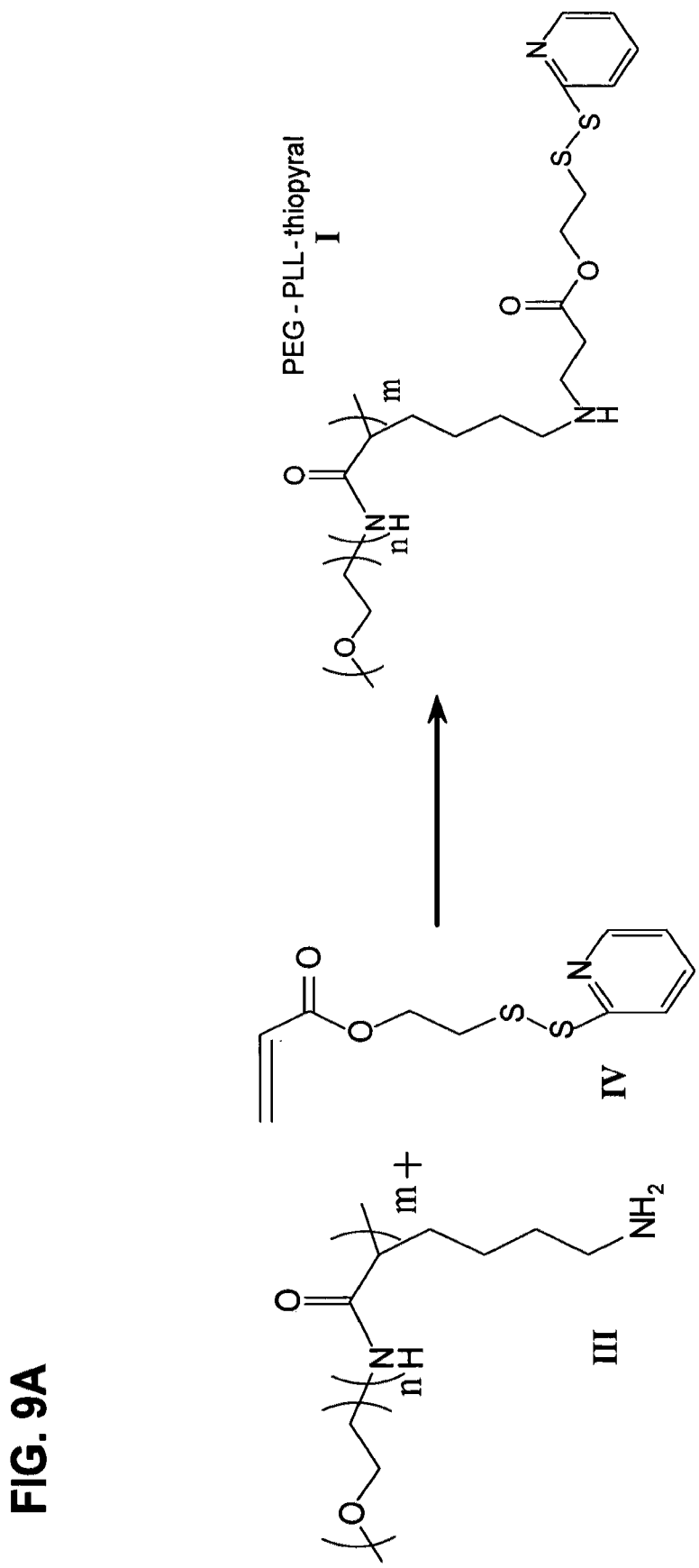
Figure 9B:
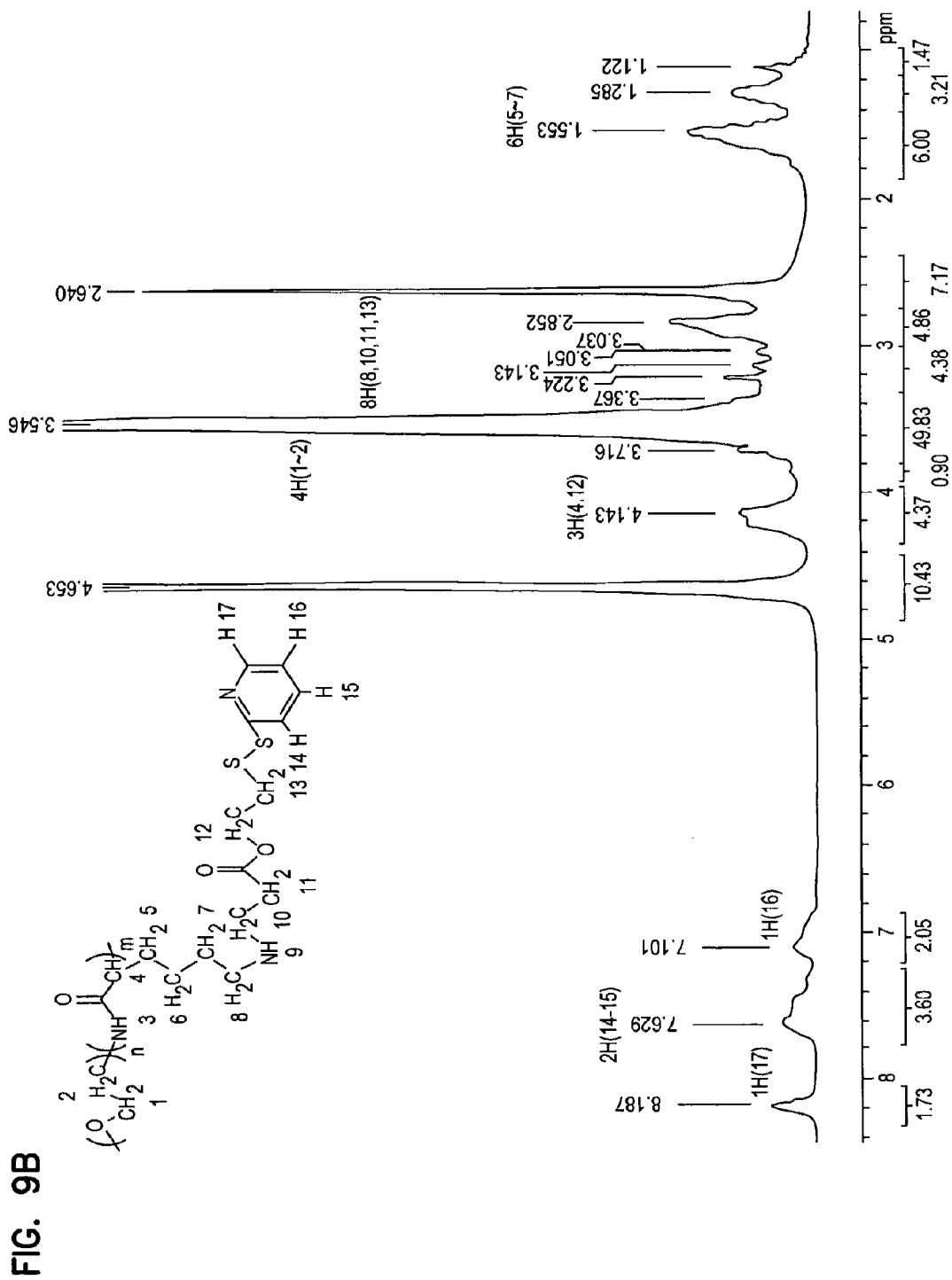
Figure 9C:
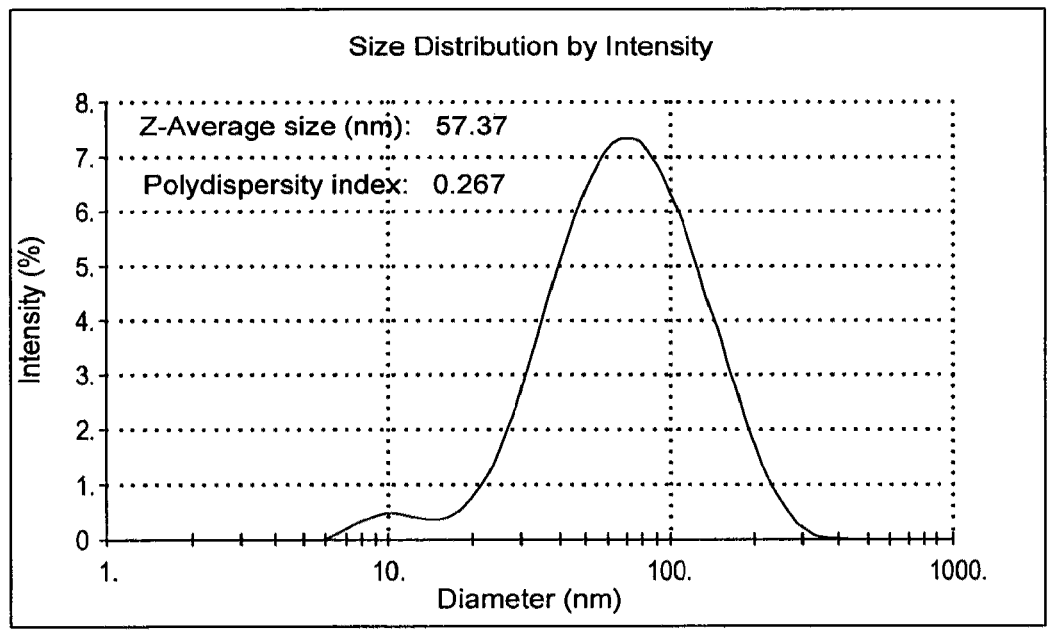
Figure 9D:
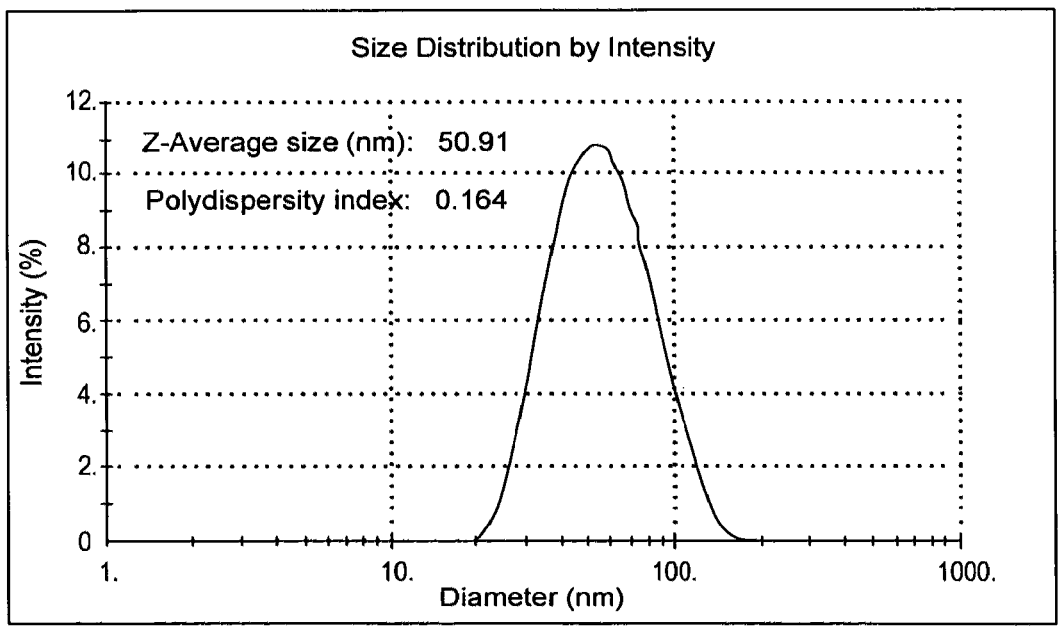
Figure 9E:
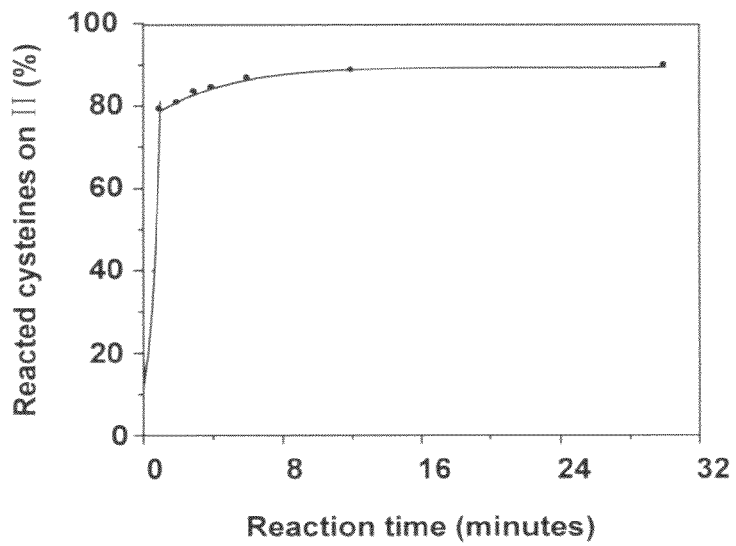
Figure 9F:
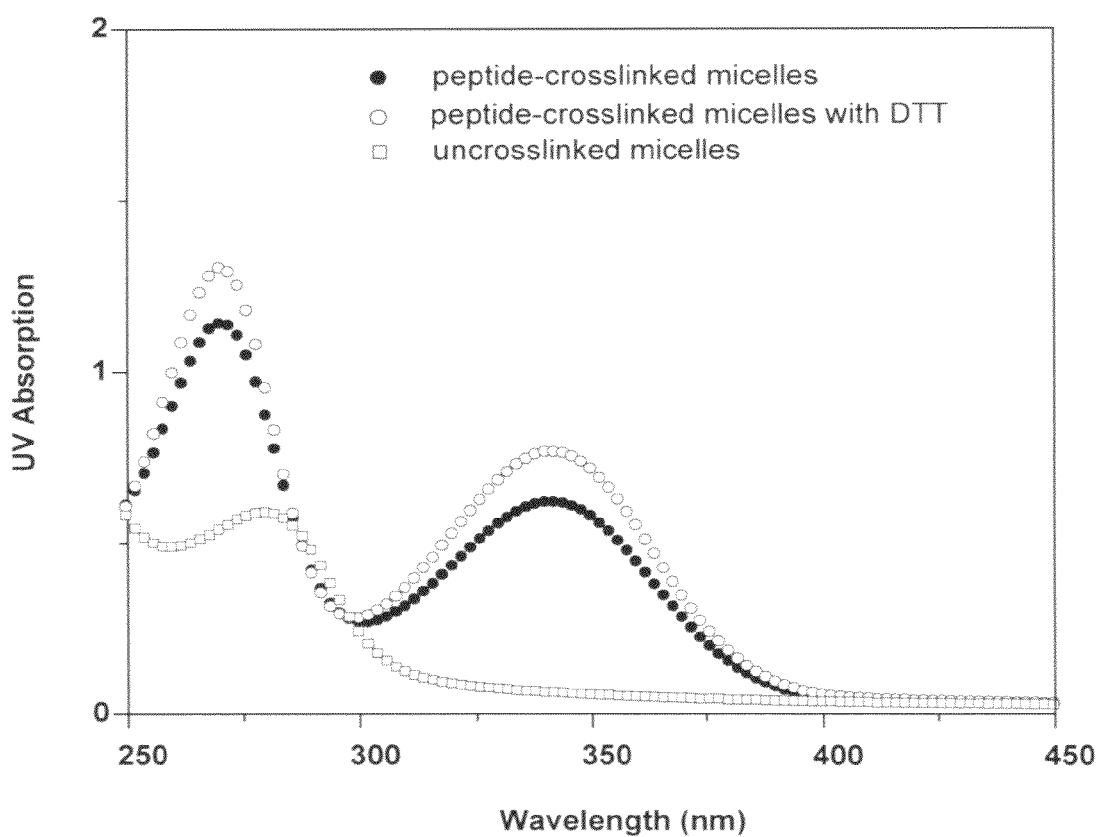

FIG. 8 is a schematic diagram showing a peptide crosslinked micelle design and synthesis. Step 1: ISS DNA and I are mixed to form micelles (uncrosslinked micelle). Step 2: These micelles are then crosslinked with the antigenic peptide (II) to generate a delivery system that can encapsulate both immunostimulatory molecules and peptide antigens. After phagocytosis by APCs, the peptide-crosslinked micelles release their components. (Example 6, infra)

FIG. 9 shows the synthesis and characterization of PEG-polylysine thiopyridal. A. is a chemical diagram showing the synthesis of PEG-polylysine thiopyridal. B is a 1H-NMR spectrum of PEG-PLL-thiopyridal in D$_2$O. C./D are graphs depicting the dynamic light scattering analysis of PCMs uncross-linked (C) and peptide cross-linked (D). E is a graph showing the crosslinking reaction of cysteines on peptide anigen II (FIG. 8). F is a graph showing the UV analysis of crosslinking reaction between peptide anigen II (FIG. 8) and block copolymer micelles. (Example 6, infra)

Figure 10A:
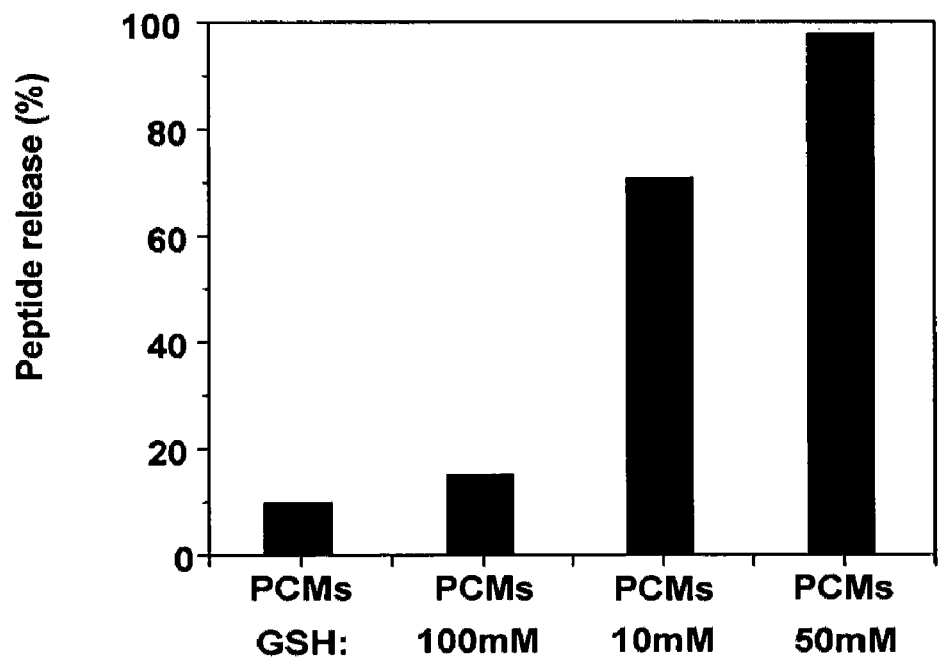
Figure 10C:
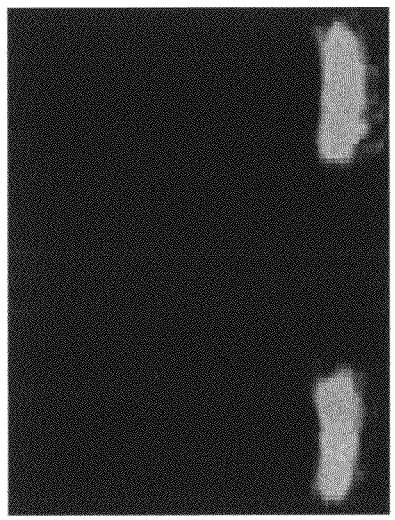

FIG. 10 shows the effect of GSH on release of peptides and DNA. A is a graph showing GSH sensitive peptide release. B is a gel elecrophoresis analysis showing GSH sensitive DNA release. C is a gel elecrophoresis analysis showing ISS-DNA is protected from serum nucleases in the PCMs. (Example 6, infra)

Figure 11A:
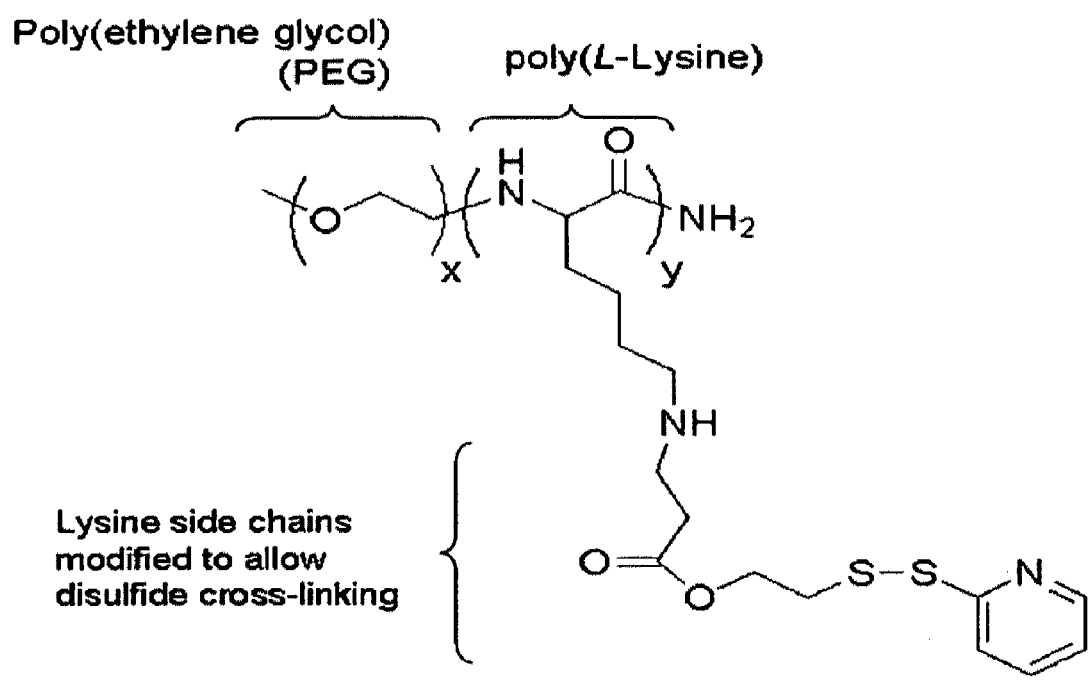
Figure 11B:
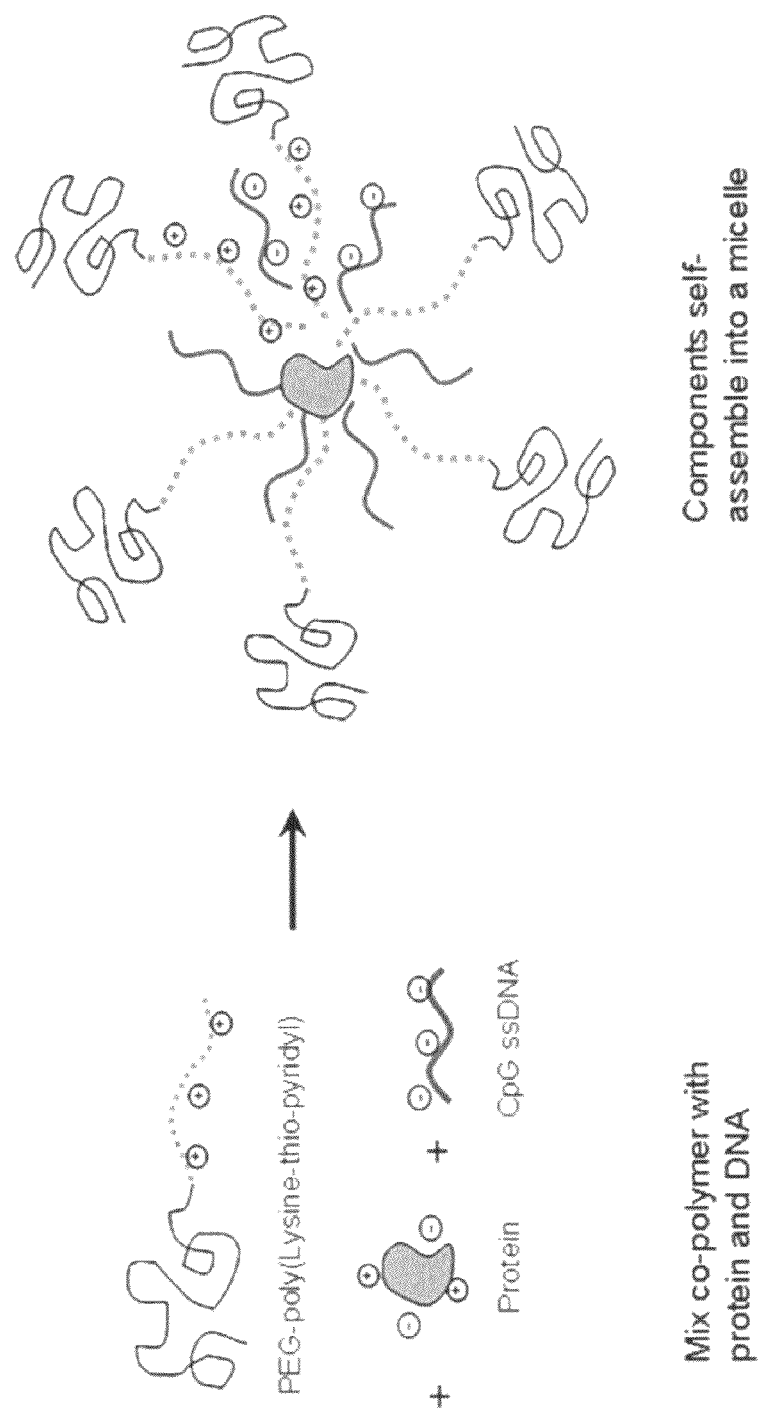
Figure 11D:
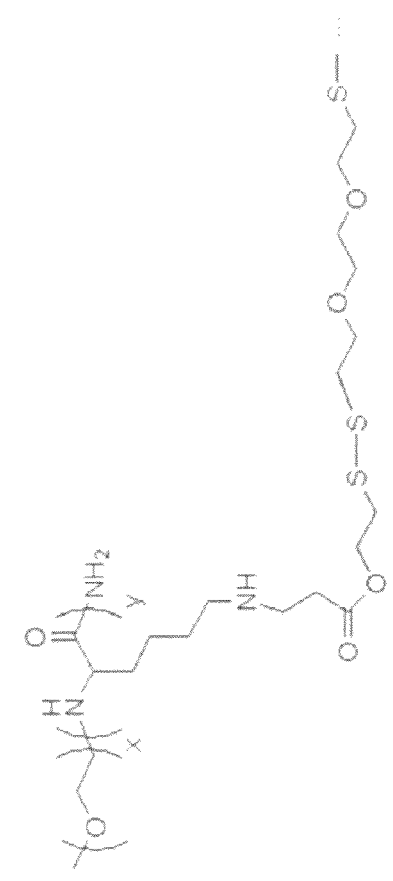

FIG. 11 depicts block copolymer micelles. A depicts the chemical structure of PEG-poly (lysine-thio-pyridyl). B is a schematic diagram showing micelle formation. C is a schematic diagram showing crosslinking of micelles. D is a schematic diagram showing reducing of crosslinked micelles. (Example 6, infra)

Figure 12A:
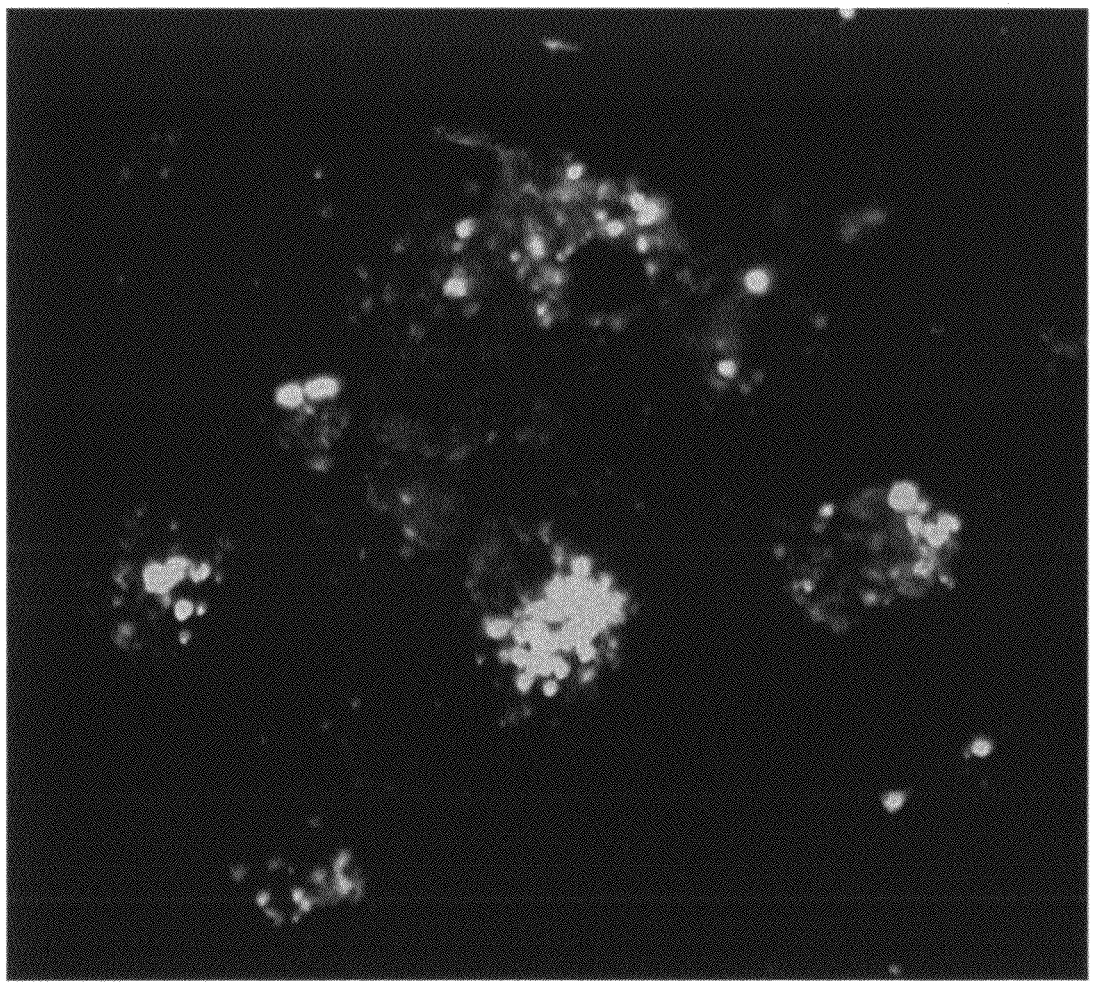
Figure 12C:
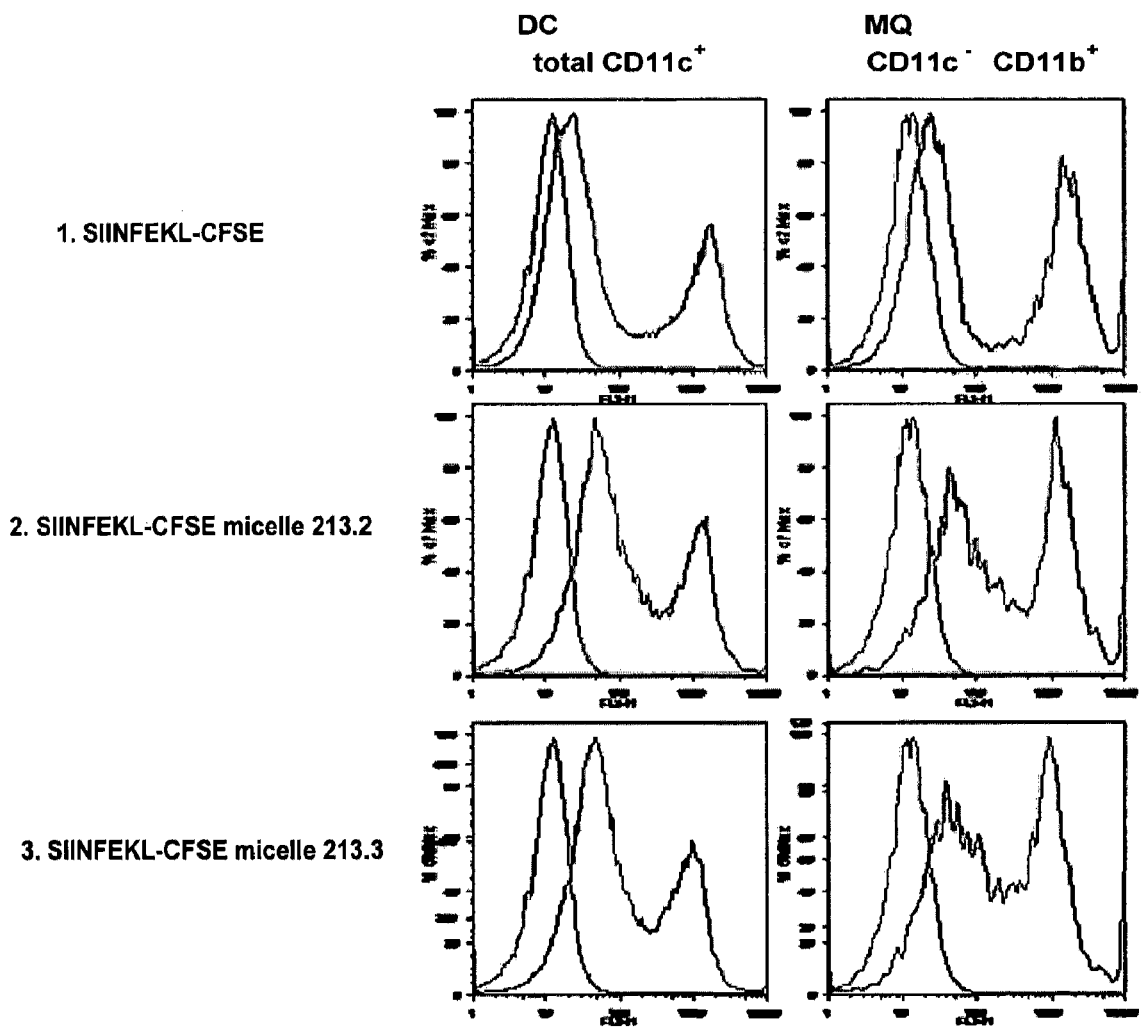

FIG. 12 shows the immunology of micelle. A. Confocal microscopic analysis of the uptake of SIINFEKL-CFSE (SEQ ID NO:1)micelles by human monocyte derived DCs. B. FACS analysis of uptake of micelle encapsulated SIINFEKL peptide (SEQ ID NO:1) by human monocyte derived DCs. C. FACS analysis of uptake of micelle encapsulated SIINFEKL peptide (SEQ ID NO:1) by mouse DCs and Macrophages. (Example 6, infra)

FIG. 13 is a bar graph showing micelle formulated SIINFEKL peptide (SEQ ID NO:1)induces potent T cell responses in-vitro (Example 6, infra).

FIG. 14 shows the immunology of micelle. A shows FACS analysis of efficient uptake of micelle encapsulated OVA protein by mouse DCs and Macrophages. B is a graph showing that micelle encapsulated OVA/CpG activates DCs in-vitro. (Example 6, infra)

Figure 15:
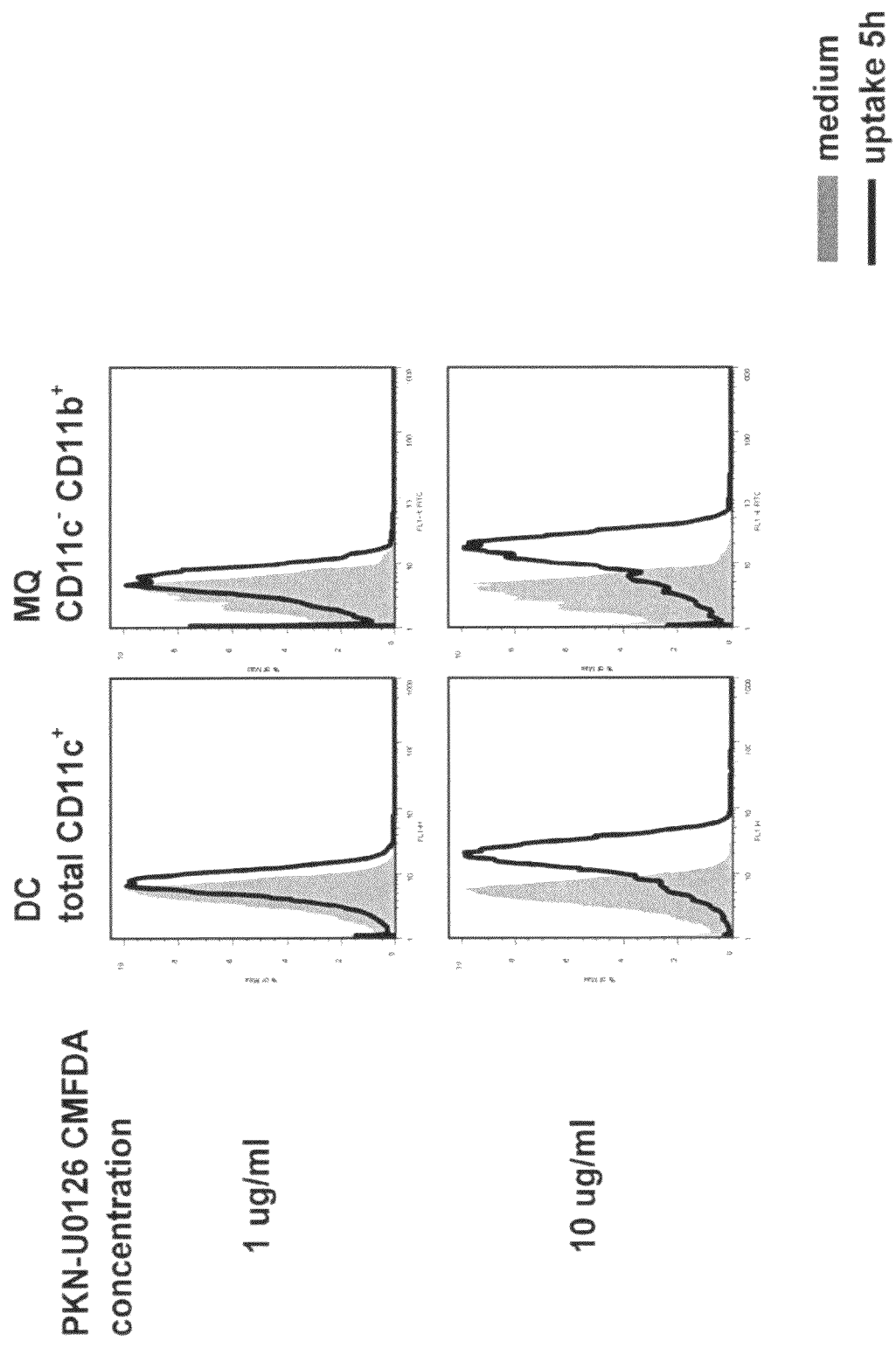

FIG. 15 is a graph depicting the immunology of polyketal particles. Uptake of polyketal particle (PKN) encapsulated U0126 by mouse DCs and Macrophages in-vitro. (Example 6, infra)

Figure 16:
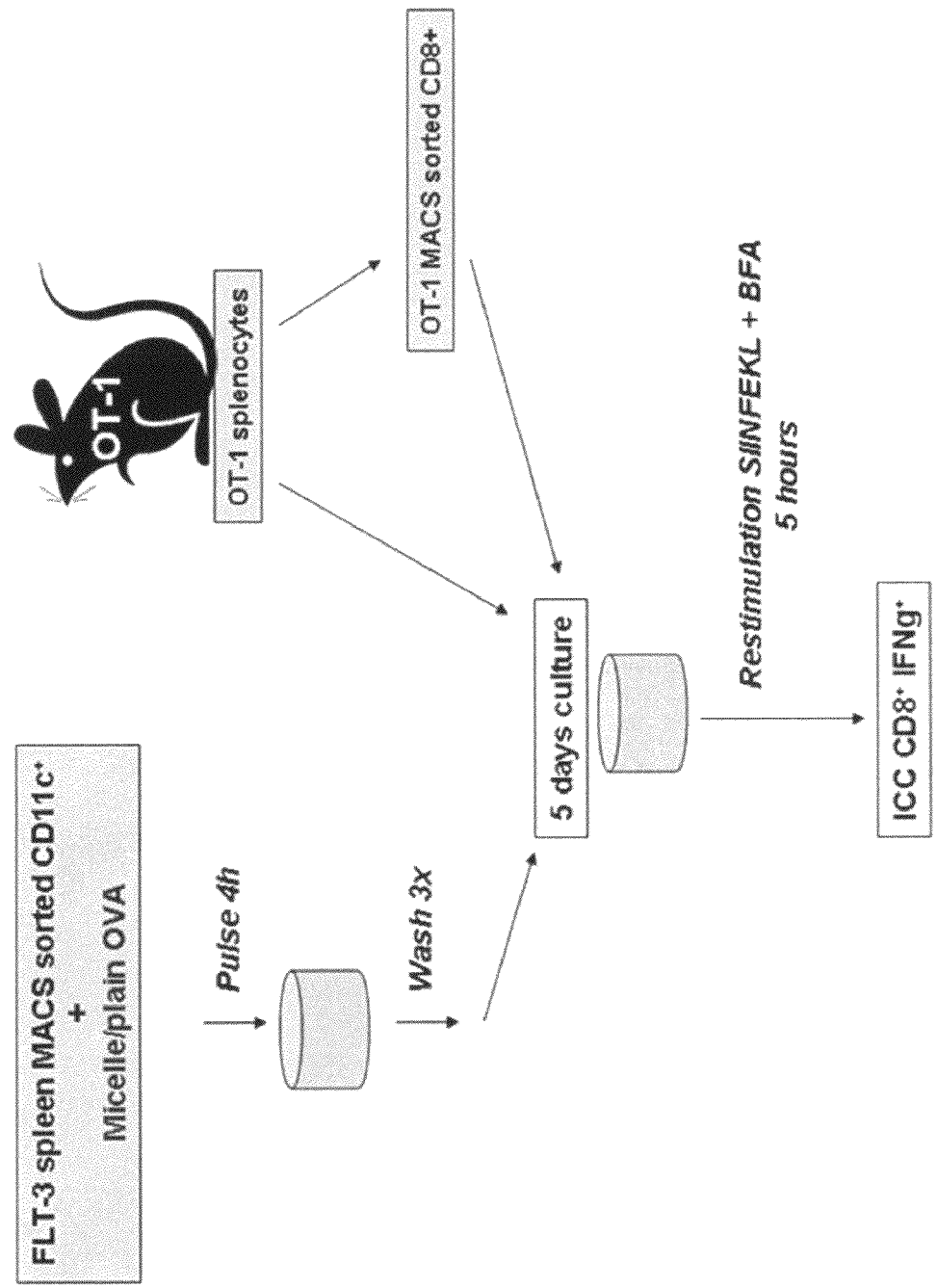

FIG. 16 is a schematic diagram showing the experimental outline for T cell stimulation in-vitro using OVA-OT/1 transgenic model. (Example 6, infra)

Figure 17A:
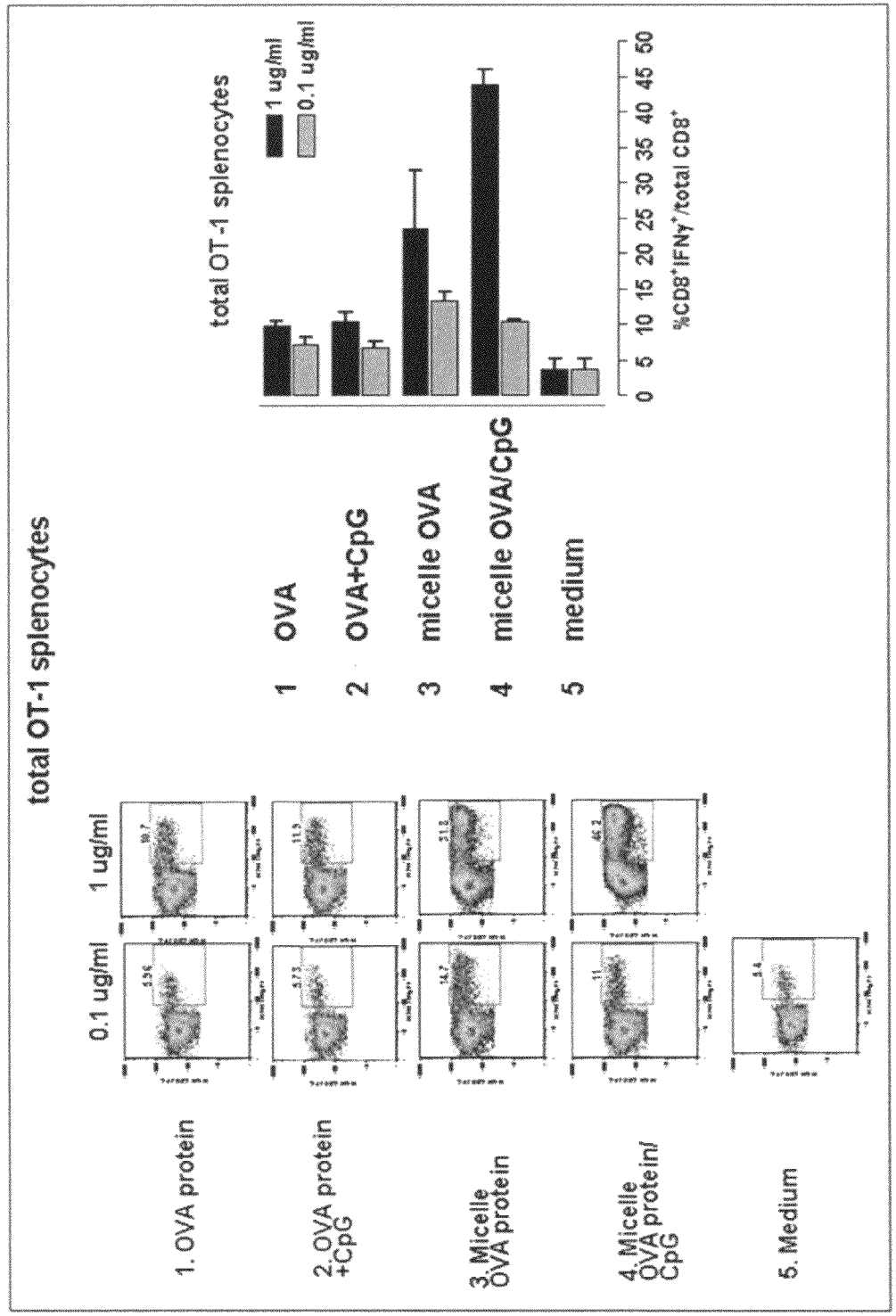
Figure 17B:
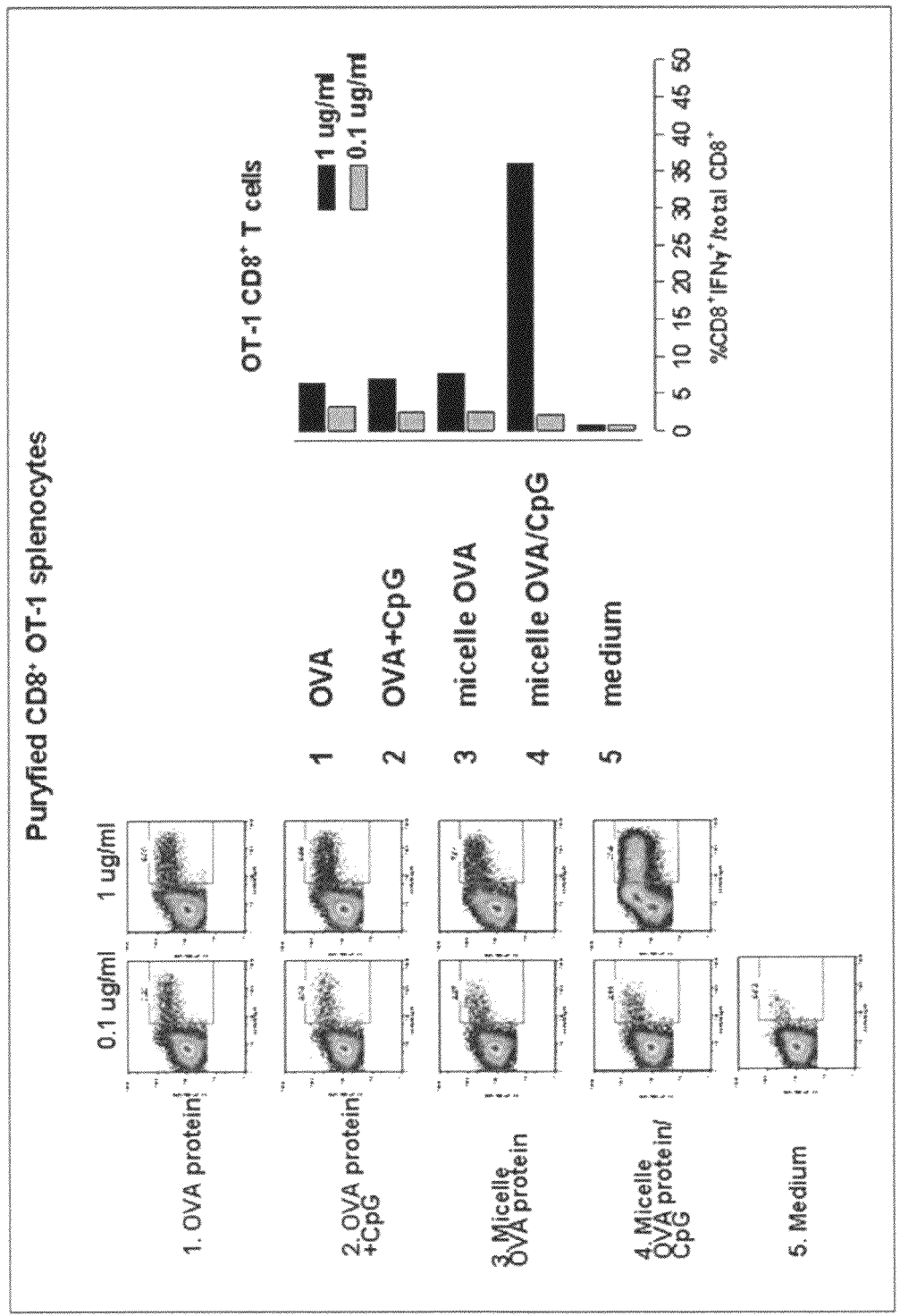
Figure 17C:
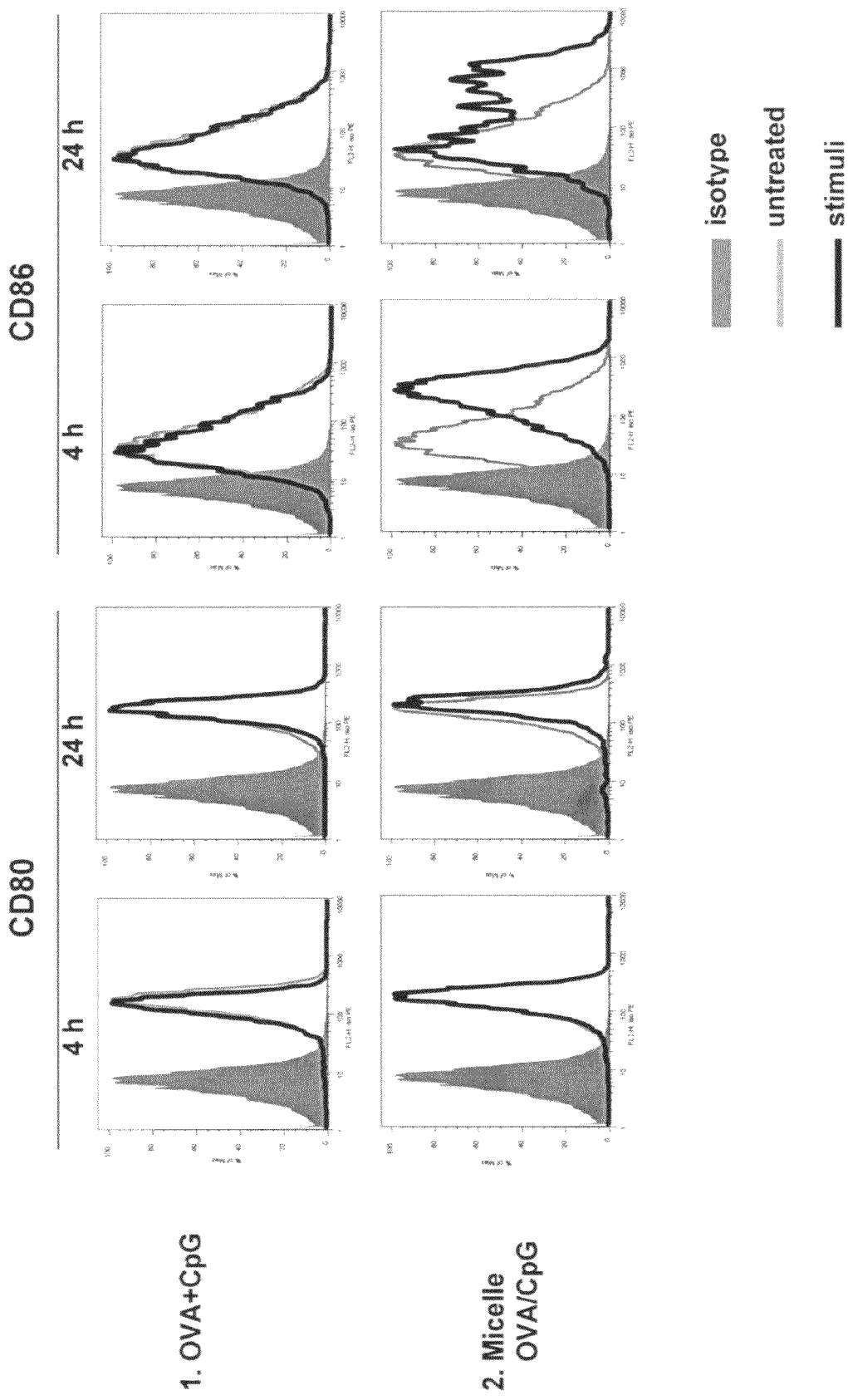
Figure 18A:
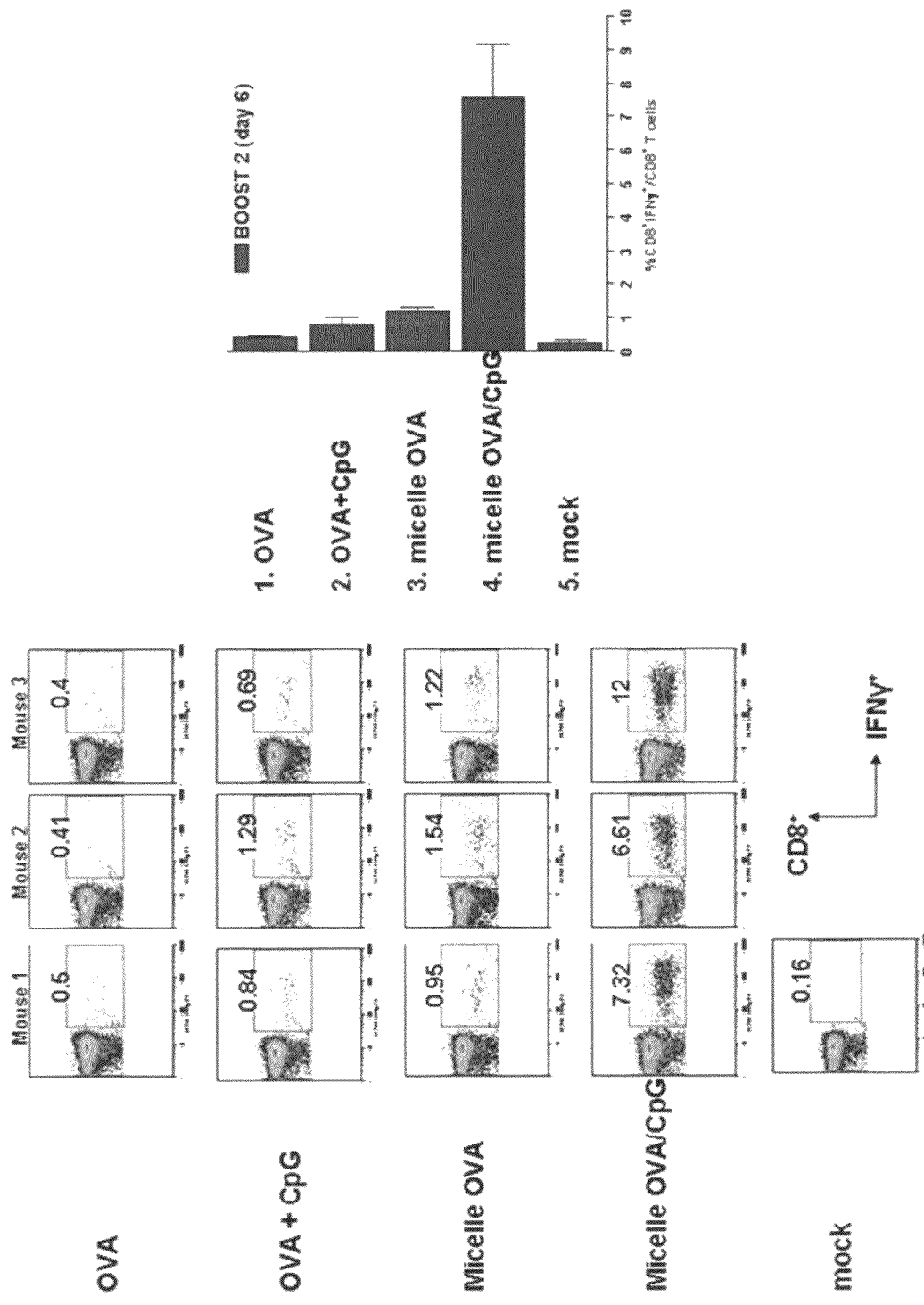
Figure 18C:
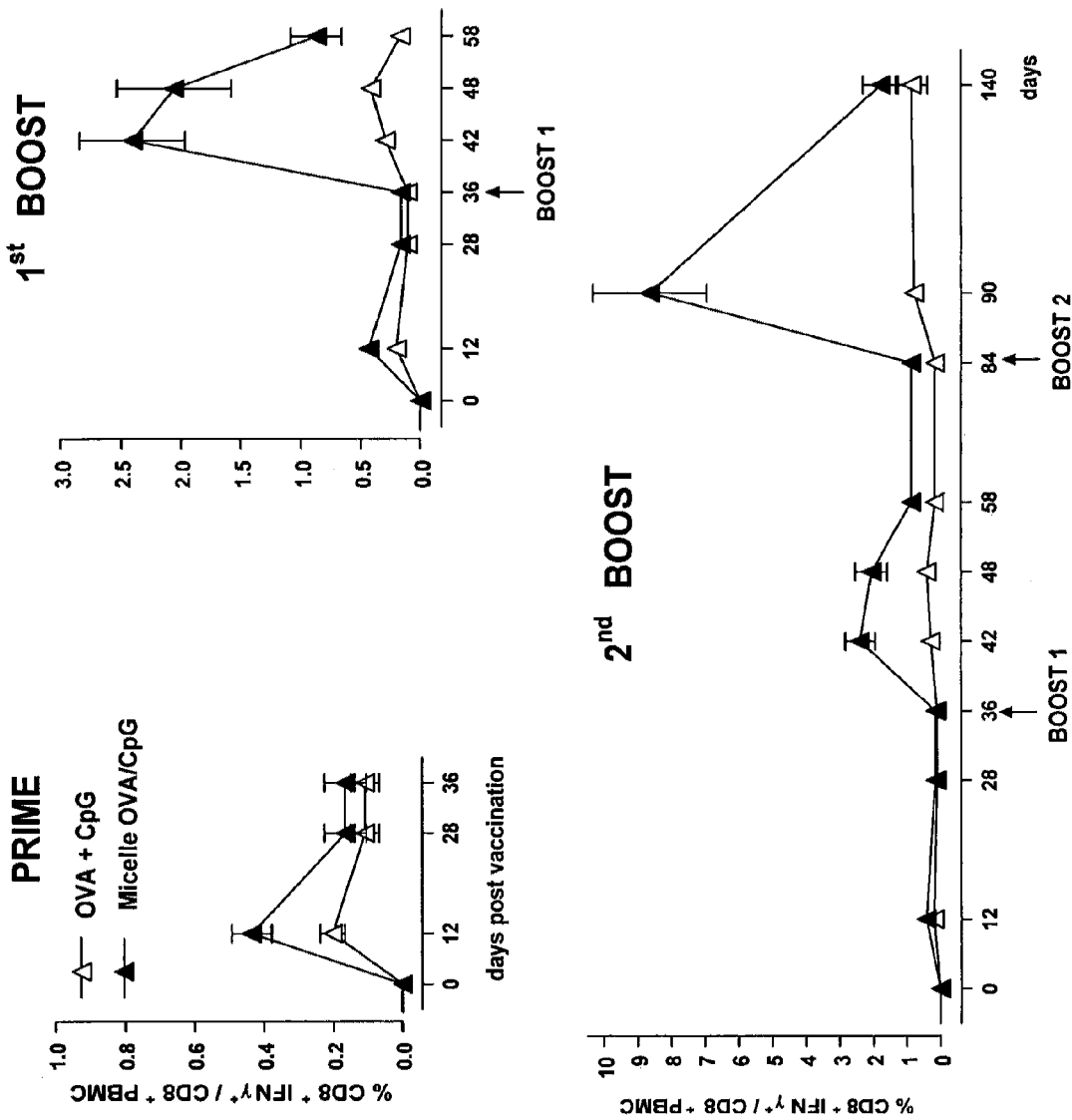
Figure 18D:
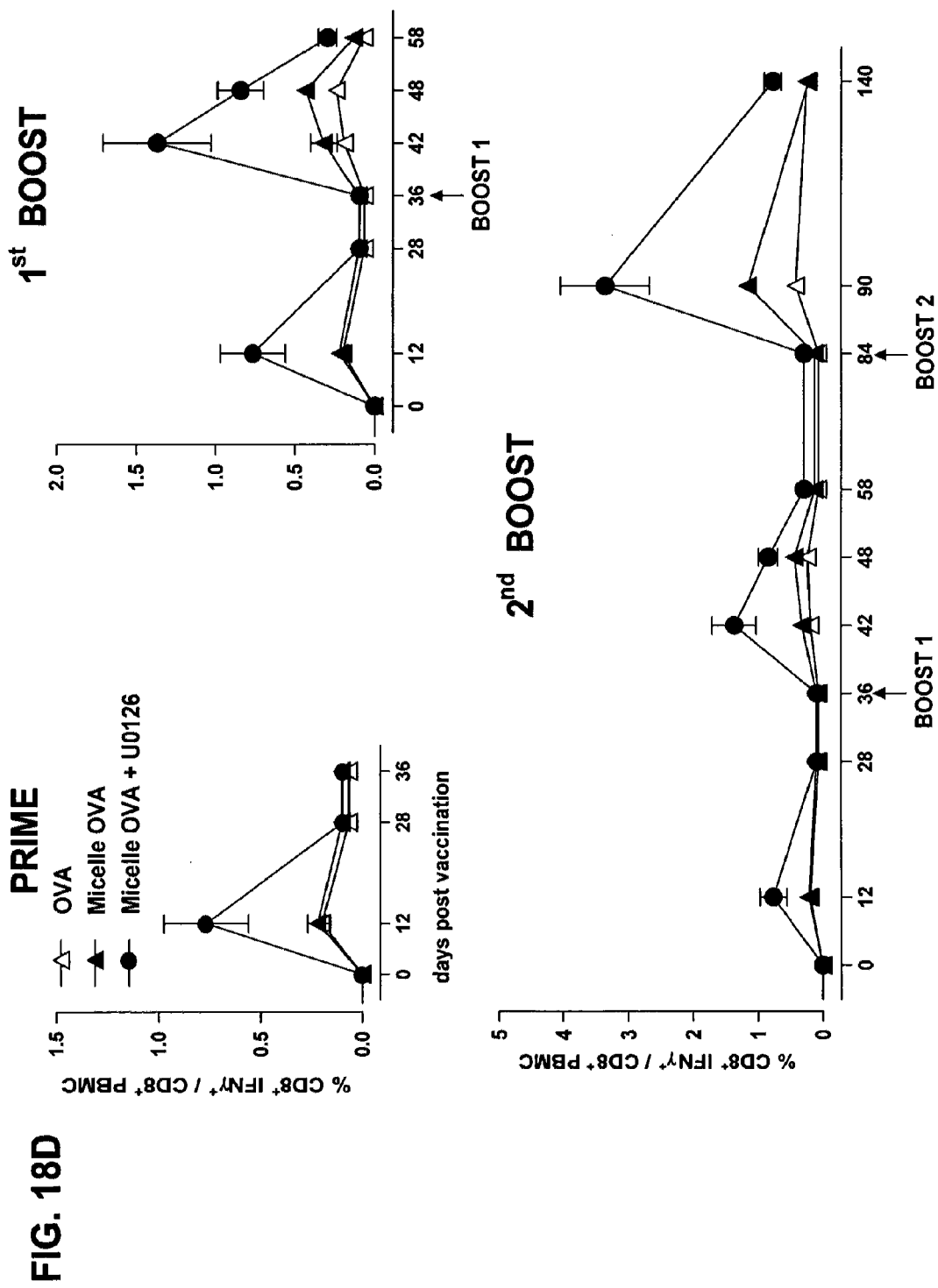
Figure 18E:
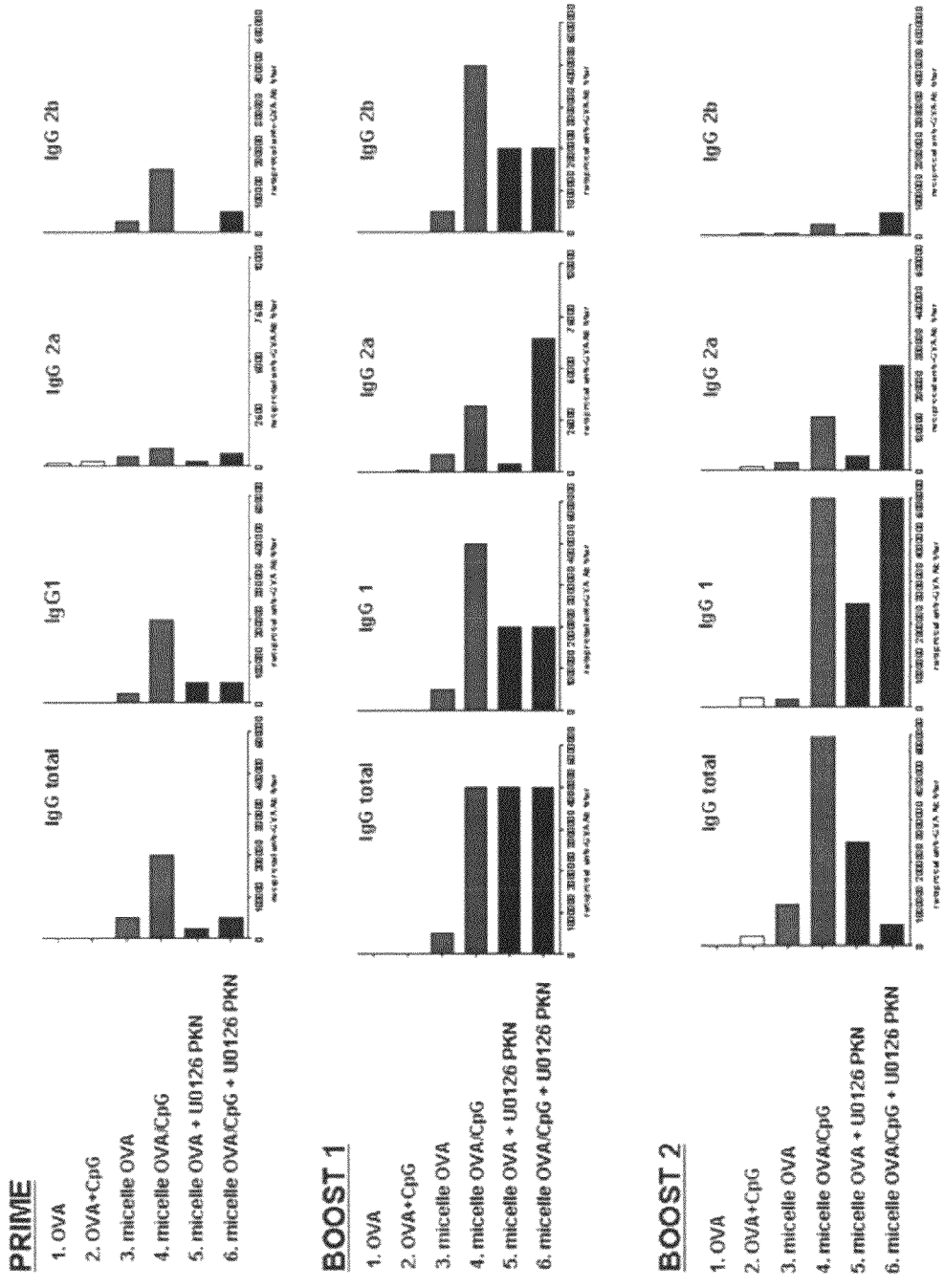
Figure 18F:
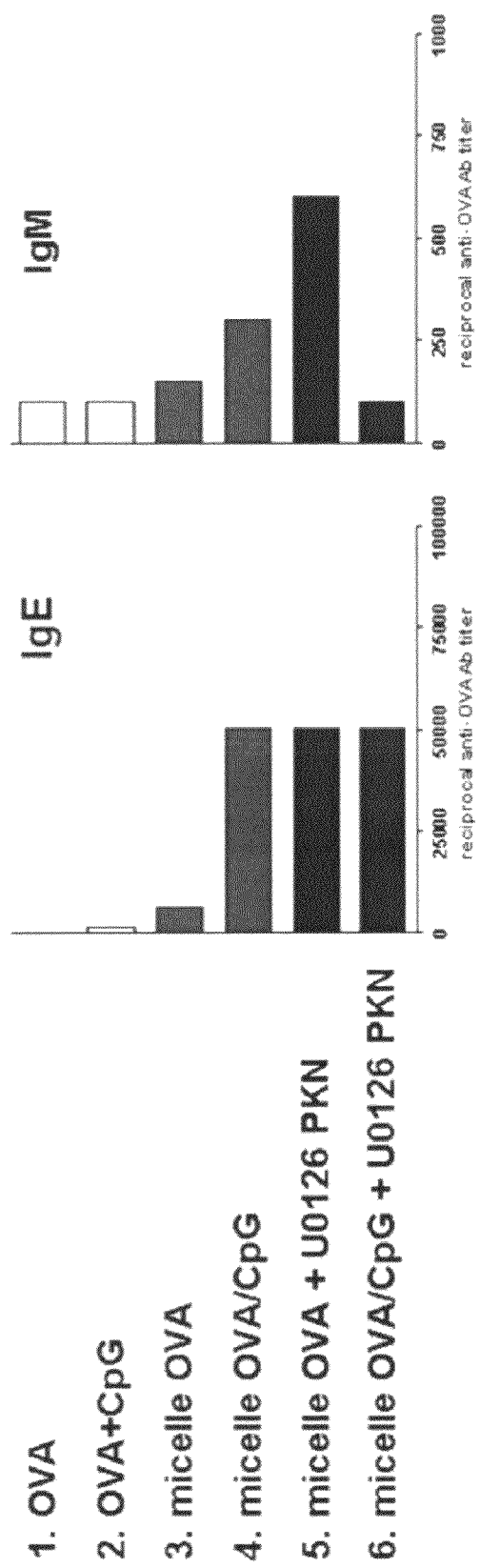

FIG. 17 shows the immunology of micelle. A. Left panel is the flow cytometery analysis and the right panel is the summary showing that splenocytes pulsed with micelle formulated antigen induces potent antigen-specific CD8+ T cell responses in-vitro. B. Left panel is the flow cytometery analysis and the right panel is the summary showing that DCs pulsed with micelle formulated antigens induce potent antigen-specific CD8+ T cell responses in vitro. C. Flow cytometery analysis showing that micelle formulated antigen activate DCs in-vivo. (Example 6, infra)

FIG. 18 shows the immunology of micelle and polyketal particles. A. Left panel is the flow cytometery analysis and the right panel is the summary showing that micelle formulated vaccines induce strong antigen-specific CD8+ IFN-gamma+T cell responses in-vivo. B. Left panel is the flow cytometery analysis and the right panel is the summary showing that micelle formulated vaccines induce strong antigen-specific CD8$^+$ TNFα$^+$ T cell responses in-vivo. C. Line graphs showing the kinetics of specific CD8$^+$/IFNγ$^+$ T cells after OVA/CpG vaccination. D. Line graphs showing the kinetics of specific CD8$^+$/IFNγ$^+$ T cells after OVA+UO126 PKN vaccination. E. Bar graphs showing that micelle formulated vaccines induce strong antigen specific IgG antibody response in-vivo. F. Bar graphs showing that micelle formulated vaccines induce antigen specific IgE and IgM antibody response in-vivo. (Example 6, infra)

FIG. 19 shows polyketals from cyclohexane dimethanol (termed PCADK herein with IUPAC designation poly(cyclohexane-1,4-diyl acetone dimethylene ketal)). A. Chemical representation showing polyketals from cyclohexane dimethanol. B. Line graph showing that PCADK degrades in an acid sensitive manner. (Example 6, infra)

FIG. 20 shows SEM images depicting that particles from PCADK can encapsulate the hydrophobic compounds and drugs such as rhodamine red and ebselen. (Example 6, infra)

Figure 21:
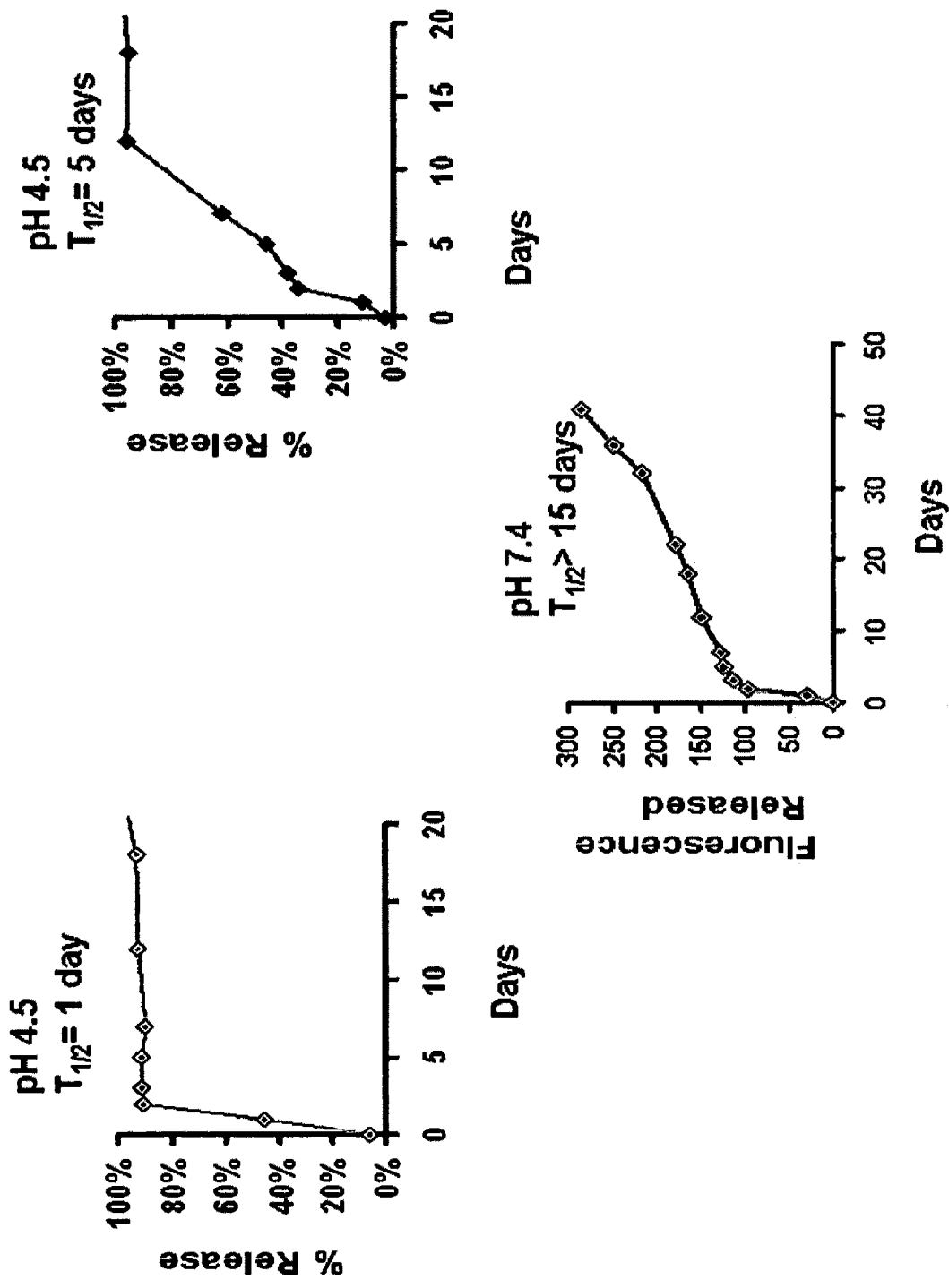

FIG. 21 shows line graphs showing that release of rhodamine red from PCADK is pH sensitive. (Example 6, infra)

Figure 22:
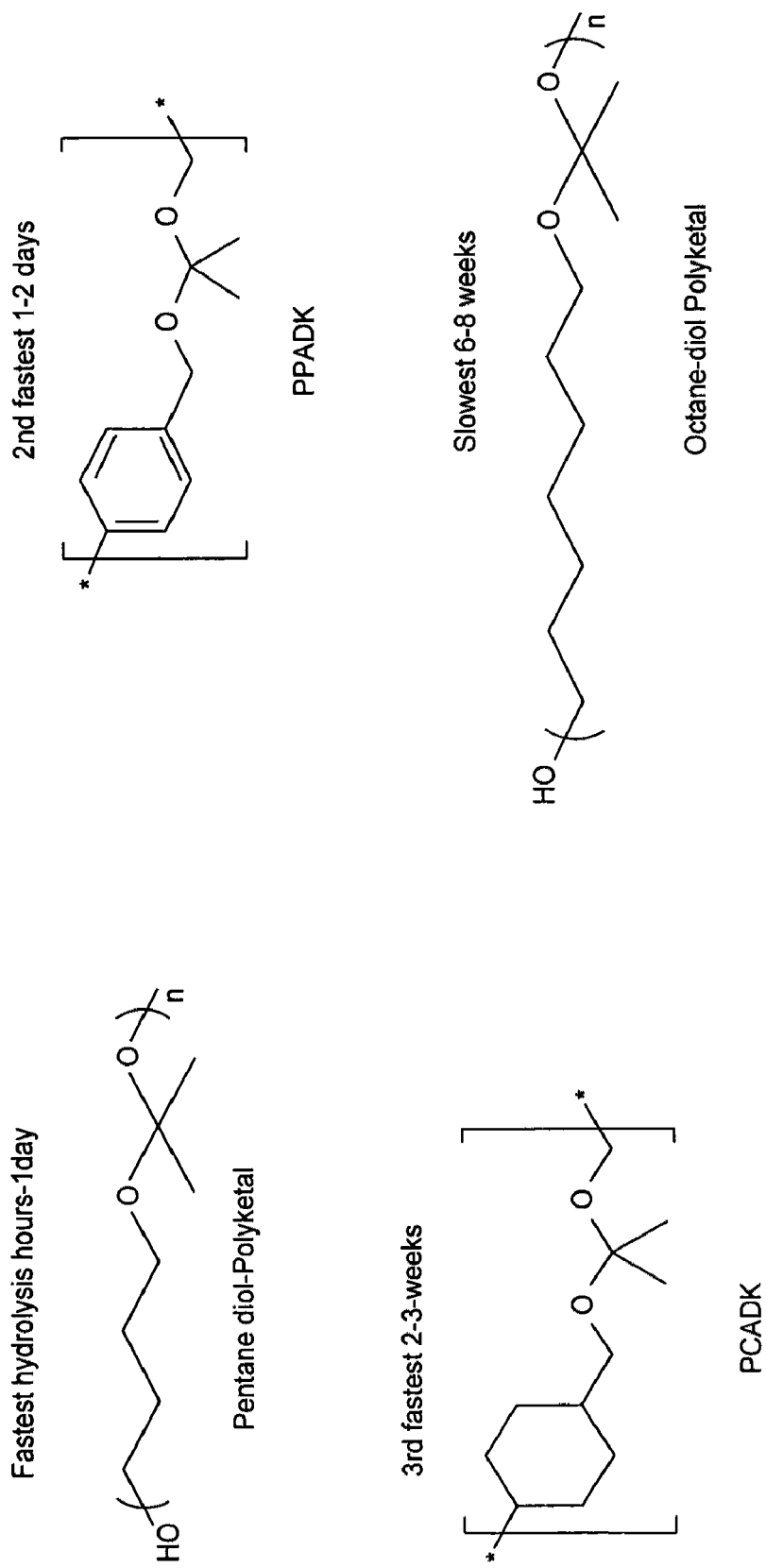

FIG. 22 is a chemical representation showing that polyketals with almost any aliphatic diol can be made. (Example 6, infra)

Figure 23:
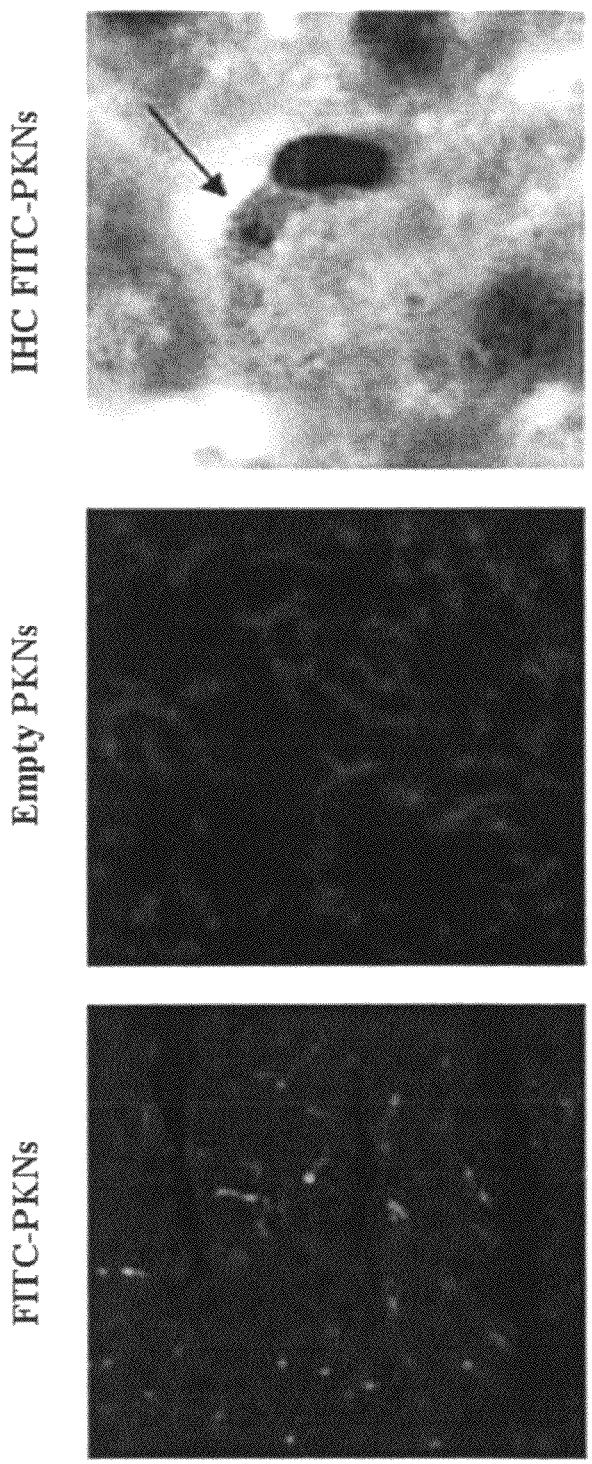

FIG. 23 is a photograph showing that FITC labeled polyketals are phagocytosed by liver macrophages. (Example 6, infra)

Figure 24A:
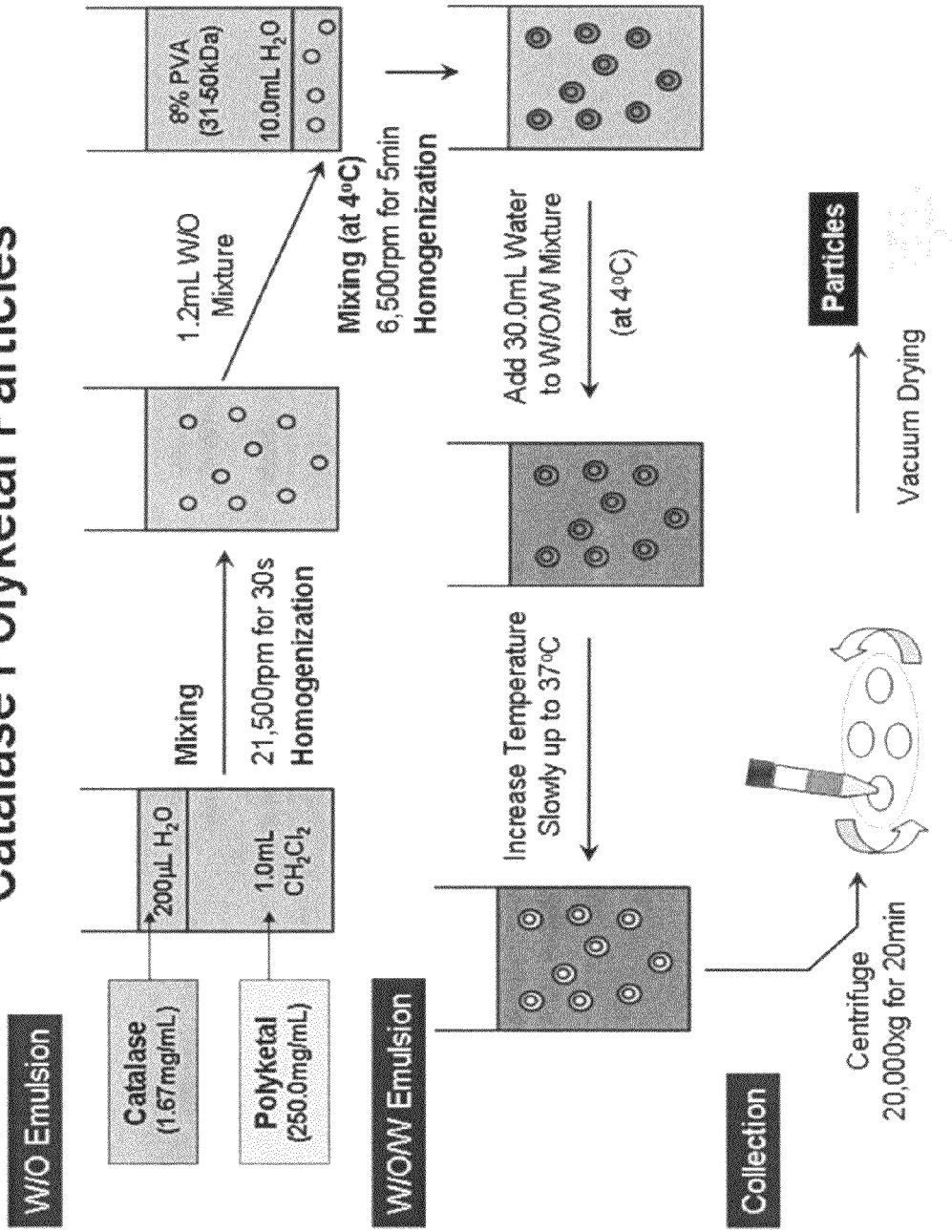

FIG. 24A is a schematic diagram showing double emulsion procedure used to encapsulate catalase and super oxide dismutase in polyketal particles. B is a SEM image of catalase containing particles, and fluorescent microscope images of catalase containing particles. C is a graph showing that catalase particles have enzymatic activity. (Example 6, infra)

Figure 25:
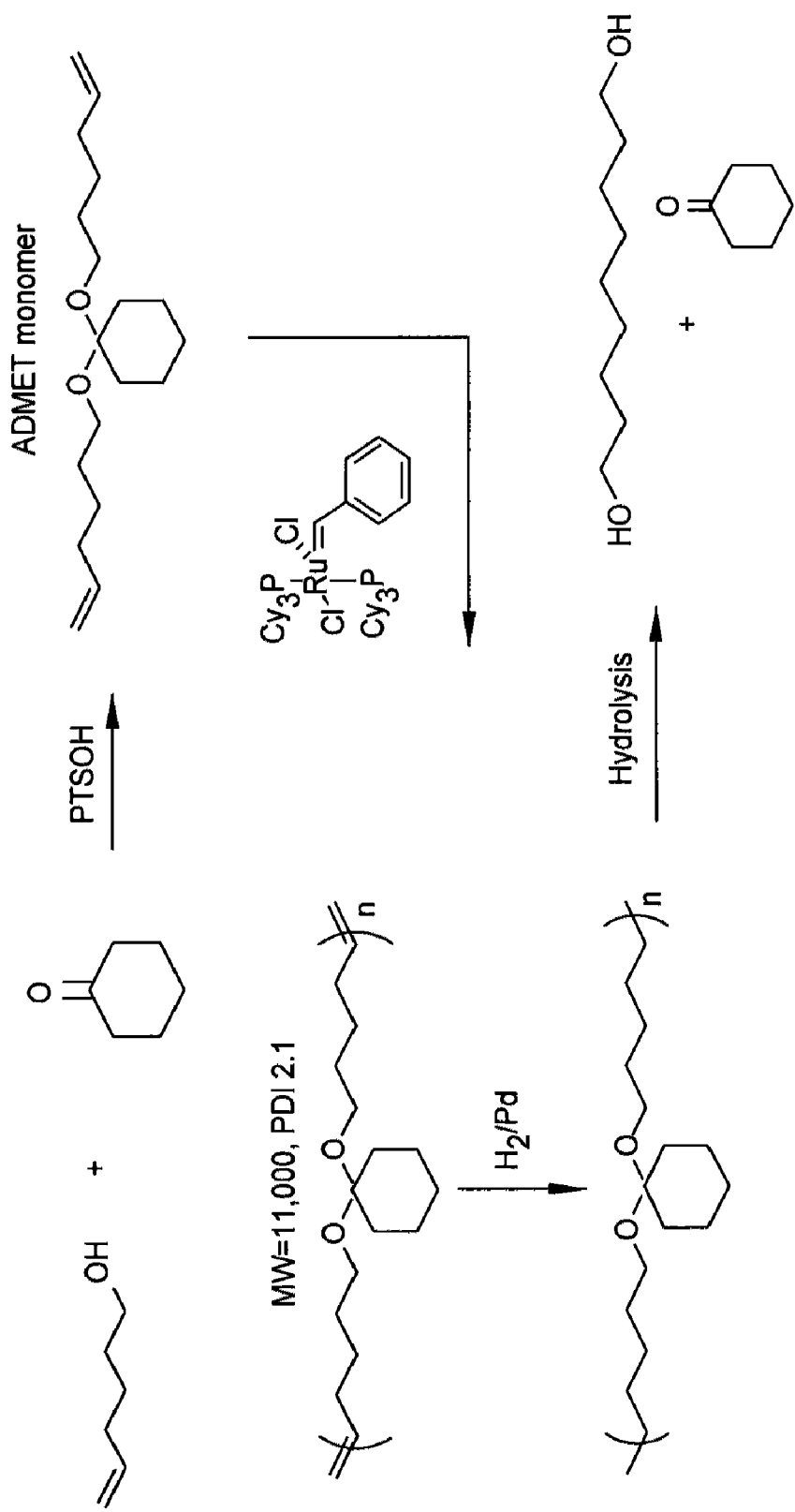

FIG. 25 is a chemical representation showing that polyketals made by acyclic diene metathesis (ADMET).

Figure 26:
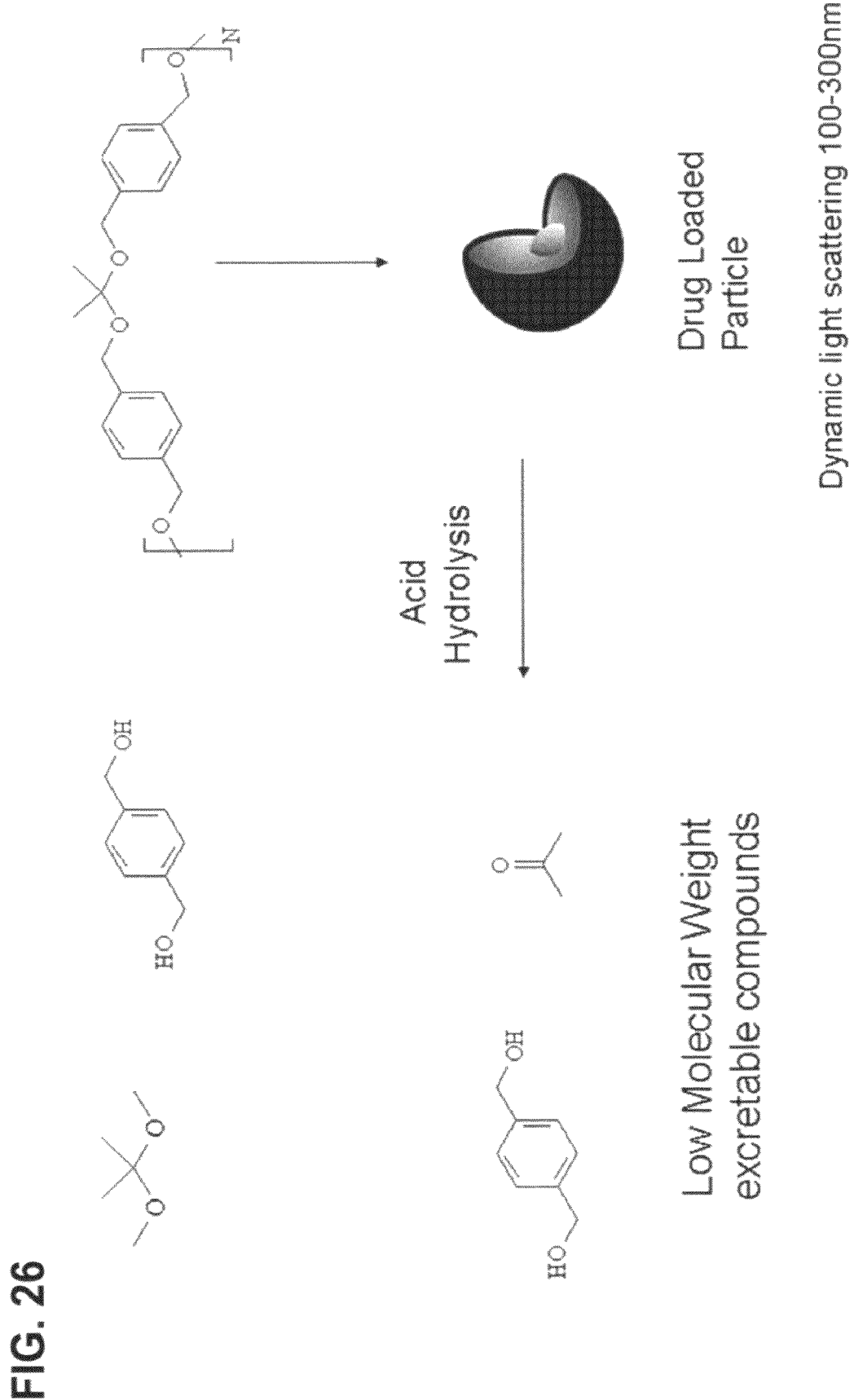

FIG. 26 is a schematic diagram for the synthesis and acid degradation of drug loaded particles.

FIG. 27 is a table showing the conditions used to make different rhodamine containing PCADK particles.

Figure 28:
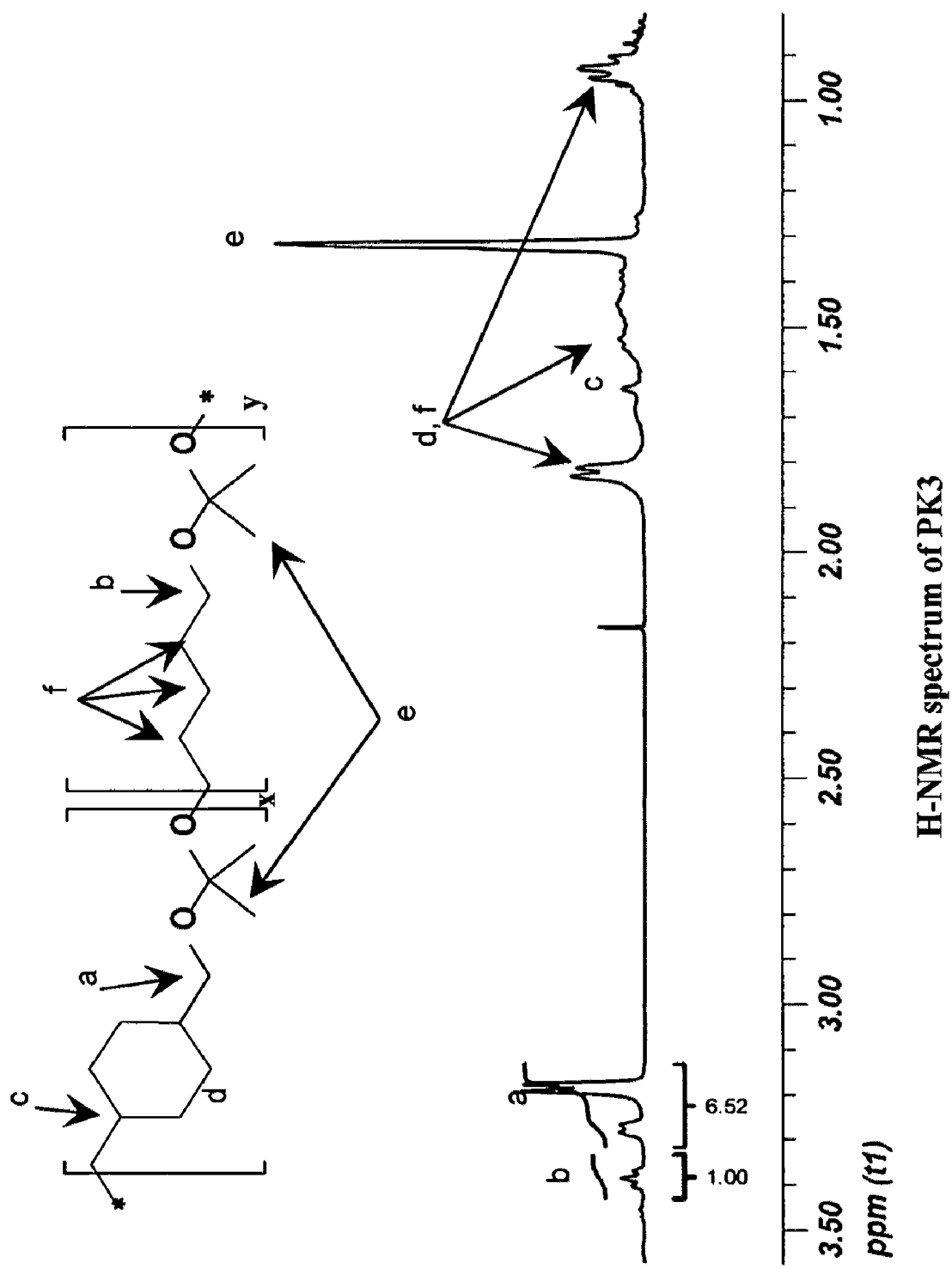

FIG. 28 shows H-NMR analysis of PK-3. The H-NMR spectrum was obtained using a Varian Mercury VX 400 MHz NMR spectrometer (Palo Alto, Calif.) using $CDCl_3$ as the solvent. The molar ratio of 1,5-pentanediol to 1,4-cyclohexanedimethanol was obtained by obtaining the ratio of areas under the peaks a and b, respectively (Example 7, infra).

Figure 29:
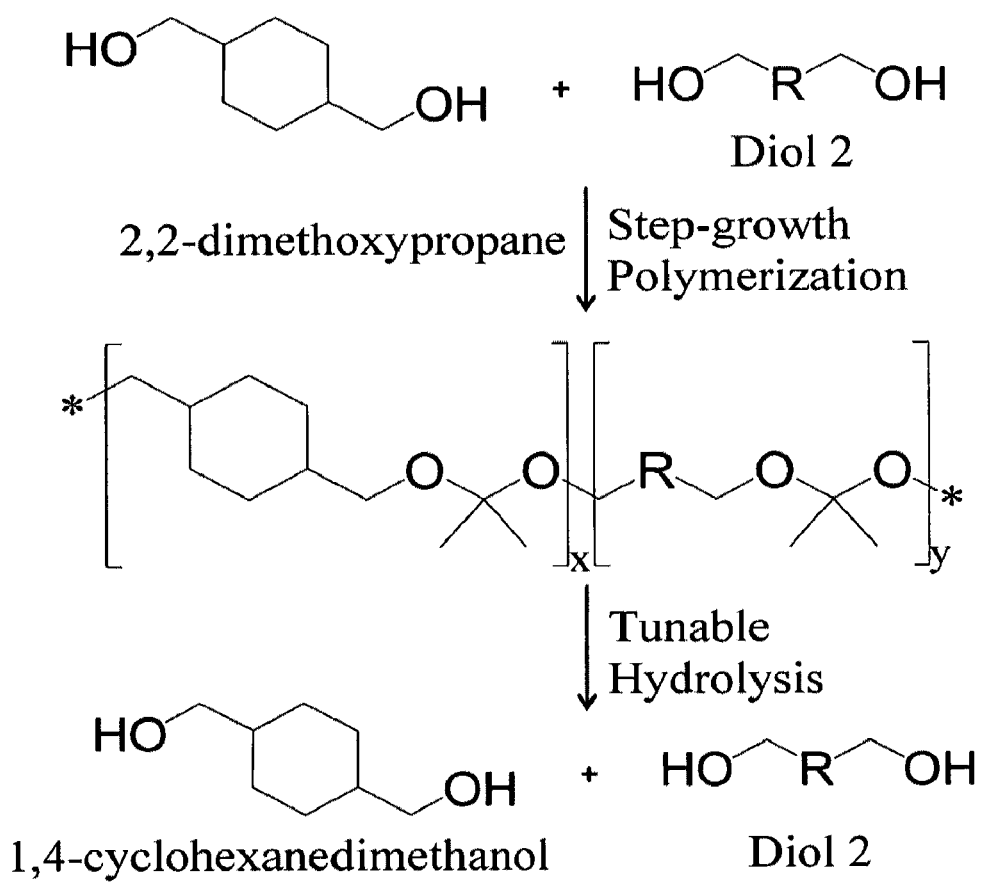

FIG. 29 is a schematic showing synthesis of polyketal copolymers from 1,4-cyclohexanedimethanol, a second diol and 2,2-dimethoxypropane. Hydrolysis kinetics of polyketal copolymers can be controlled by copolymerization (Example 7, infra).

FIG. 30 are graphs showing hydrolysis kinetics of polyketals can be tuned by copolymerization. (A) Hydrolysis profiles of polyketal copolymers PK1 to PK6 in pH 4.5 buffer, and (B) hydrolysis profiles of PK1 to PK6 in pH 7.4 buffer. Data are presented as mean±standard deviation. All experiments were conducted in triplicates at 37° C. (Example 7, infra).

Figure 31:
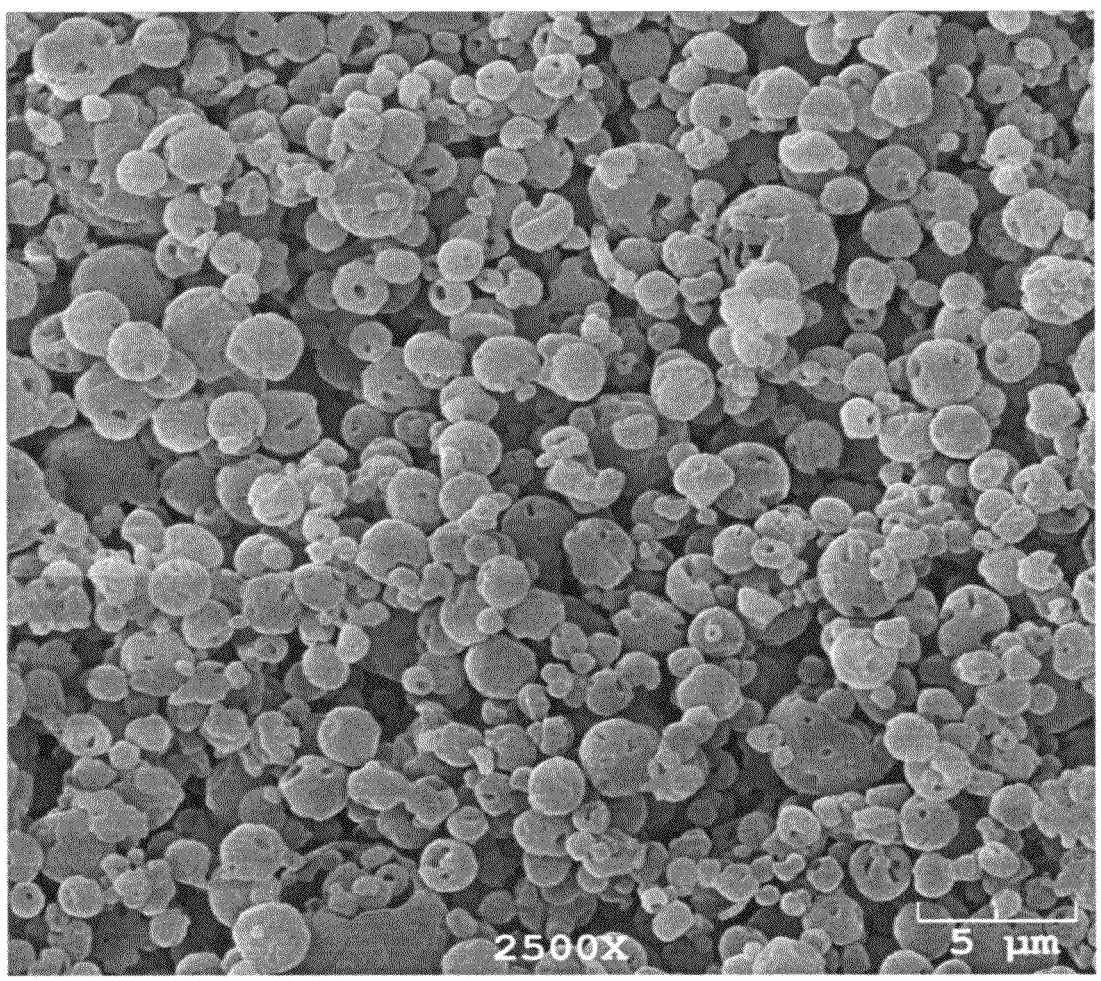

FIG. 31 is a photograph showing SEM images of particles formulated with PK3. SEM image of empty particles formulated via double emulsion procedures (Example 7, infra).

Figure 32:
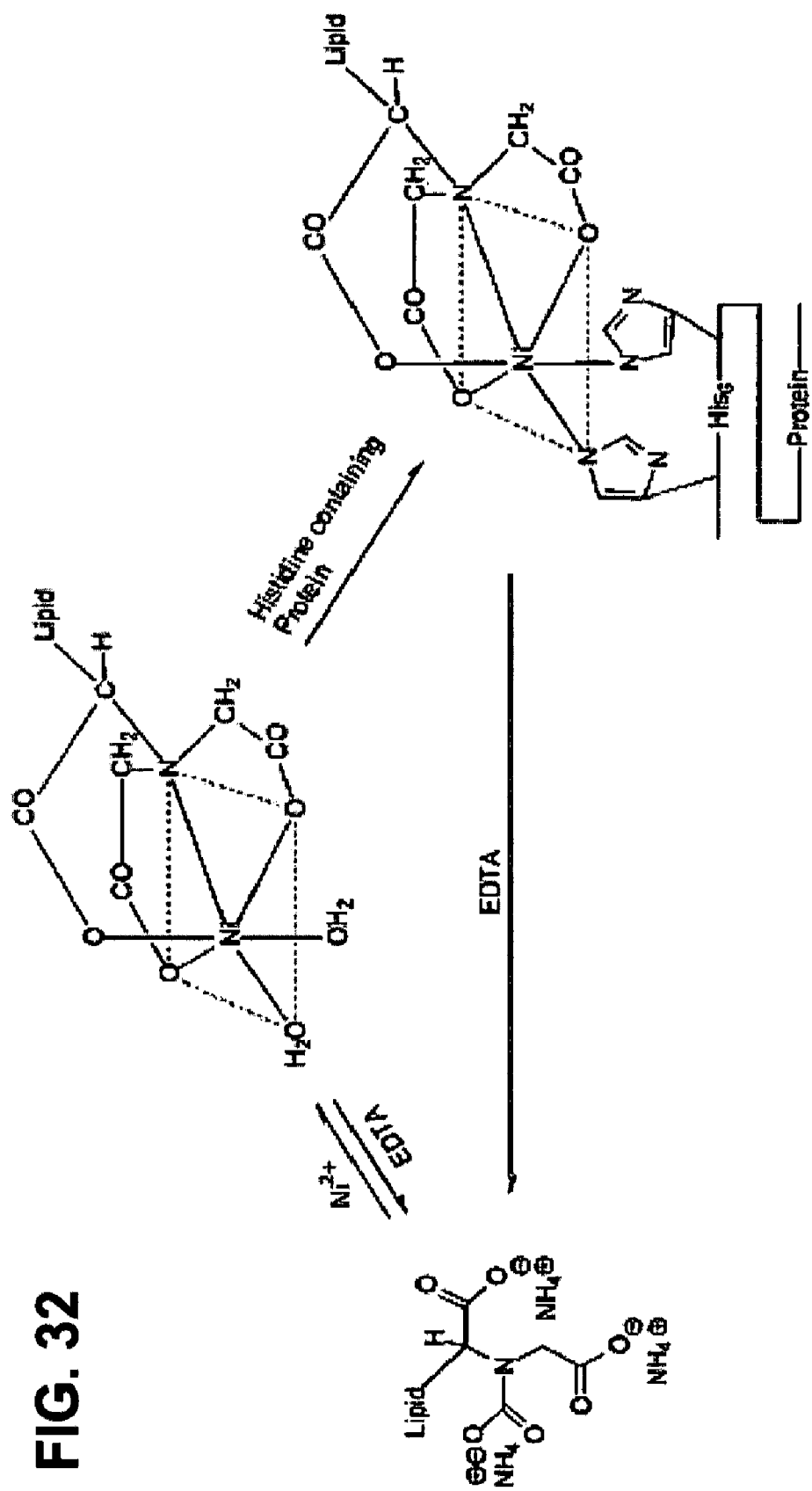

FIG. 32 is a schematic diagram of nitrilotriacetic acid (NTA) which, when loaded with nickel (Ni), binds histidine-tagged proteins (Example 8, infra).

Figure 33A:
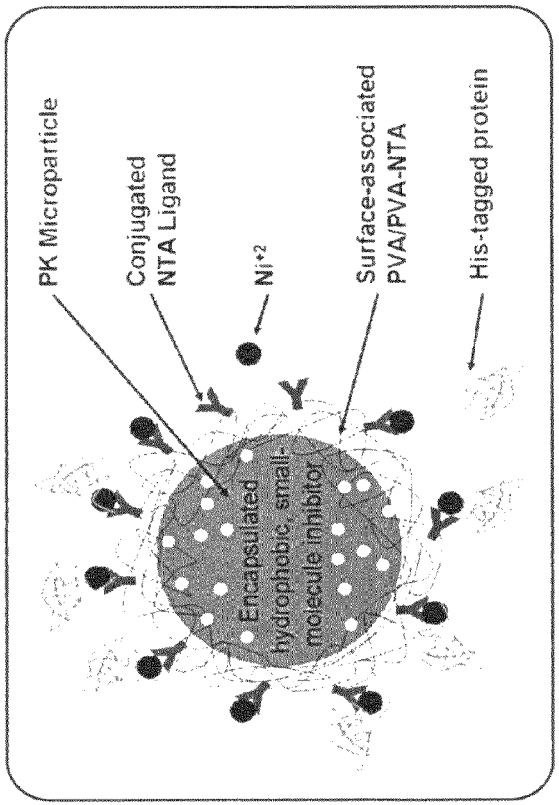
Figure 33B:
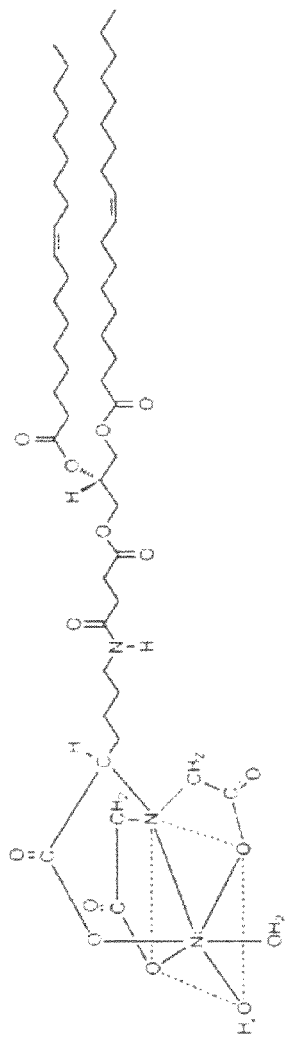

FIG. 33 is a schematic diagram of a polyketal with a NTA linker forming microspheres where active agents are encapsulated by the microsphere and His-tagged proteins are bound to the surface of the microsphere. B. A diagram of DOGS-NTA (Example 8, infra).

Figure 34B:
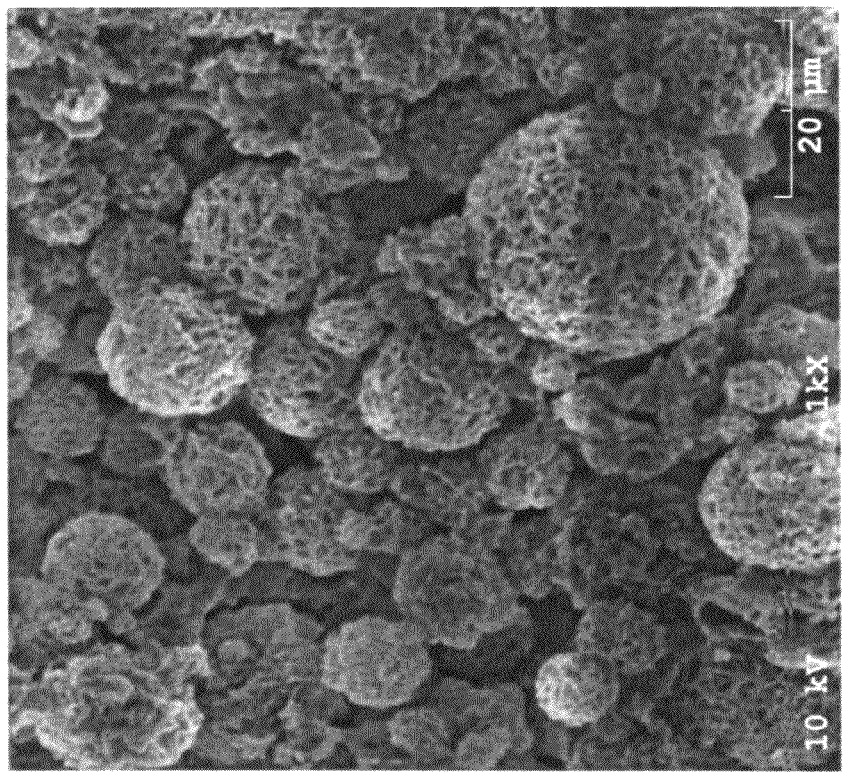
Figure 34A:
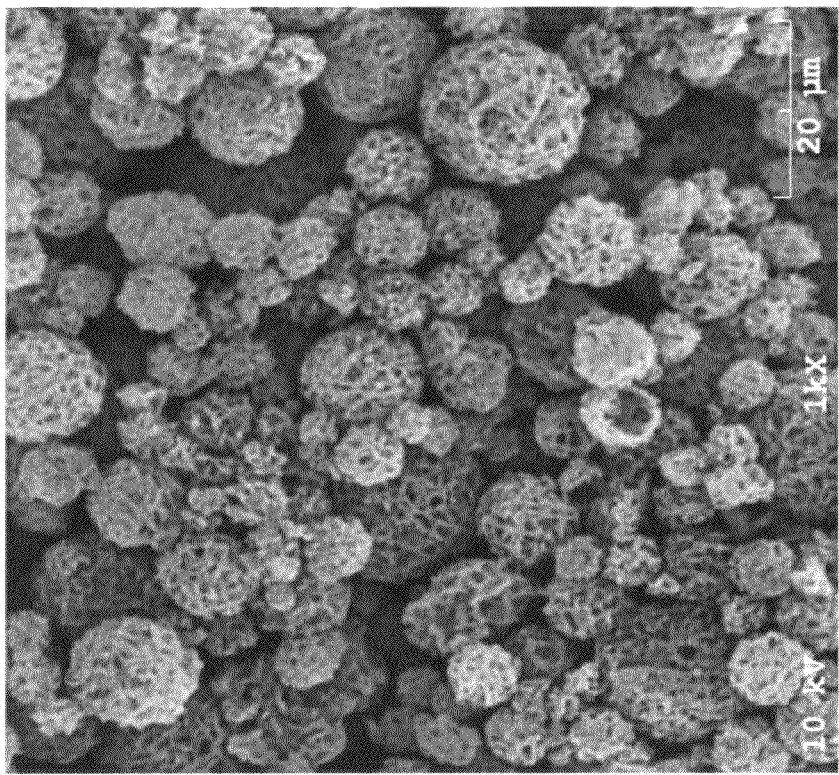

FIG. 34 is a photograph showing SEM micrographs of 10% NTA PCADK microparticles (Example 8, infra).

Figure 35:
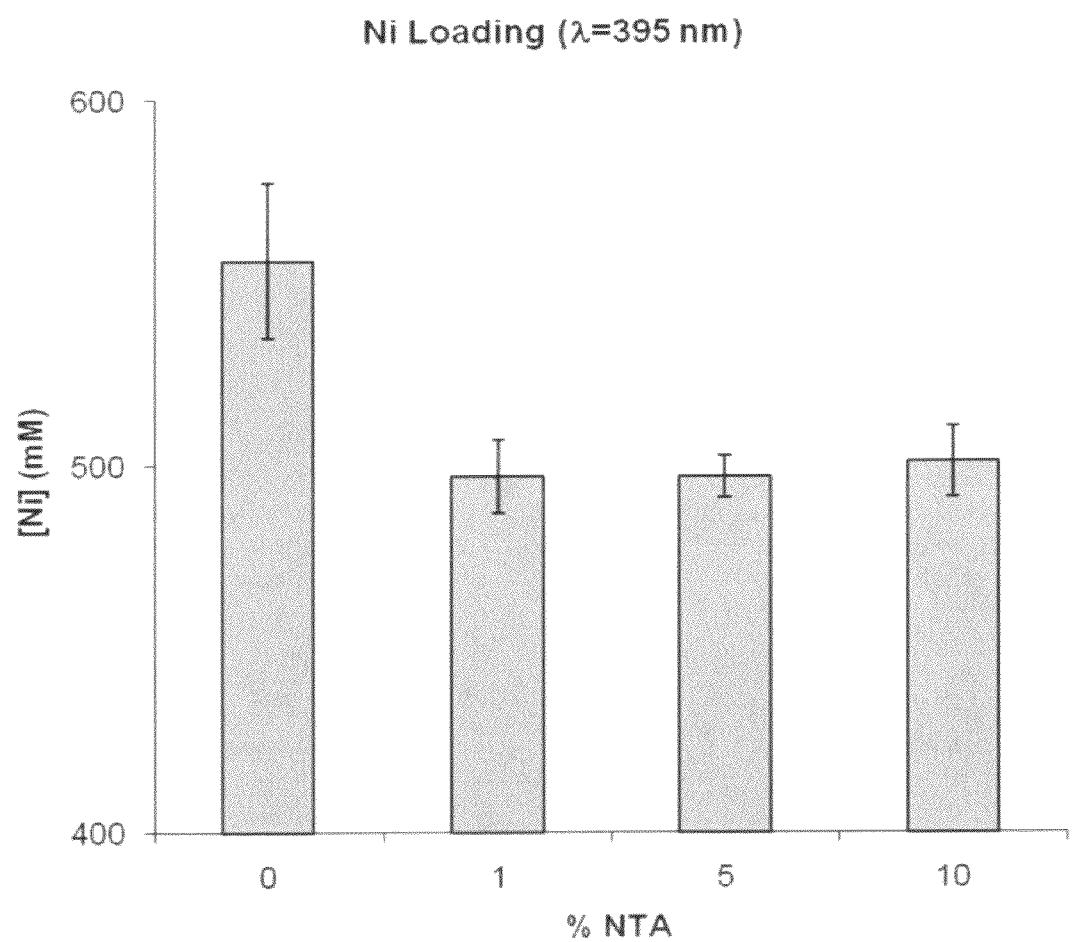

FIG. 35 is a chart showing the spectrophotometric determination of Ni depletion in loading solution. PCADK particle with varying concentrations of NTA-ligand (0%, 1%, 5%, 10%) were loaded in $NiCl_2$ solution. After incubating the particles overnight with agitation, solutions were centrifuged and the supernatants analyzed for Ni content spectrophotometrically. The supernatant particles with no NTA-ligand had a nickel concentration of about 550 mM while 1%, 5%, and 10% NTA particles had approximately 500 mM Ni in their supernants. This data suggests that the surface of the particles is saturated with 1% NTA-ligand inclusion. Further quantative testing is currently underway using atomic absorption spectroscopy (Example 8, infra).

Figure 36B:
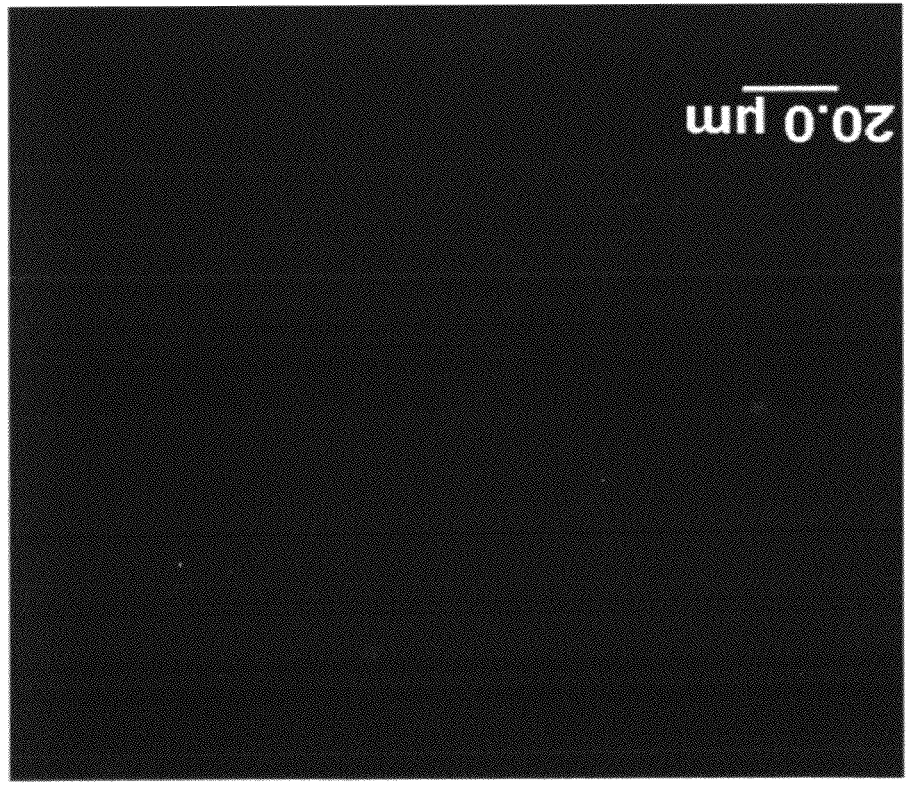
Figure 36A:
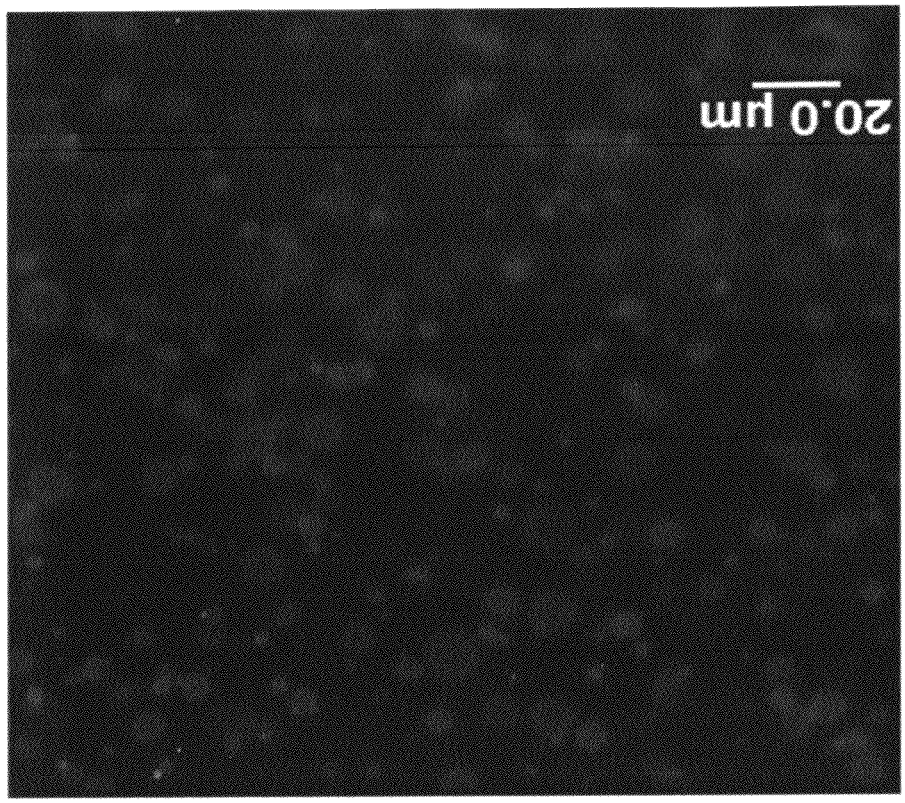

FIG. 36 are photographs showing that His-tagged Green Fluorescent Protein (GFP) is Ni dependent. 10% NTA particles were charged with Ni, washed extensively and then incubated in a 100 nM solution of His-tagged GFP. Particles were washed extensively with PBS and imaged using fluorescent microscopy. (a) PCADK-NTA particles were loaded in PBS instead of $NiCl_2$. Very little fluorescence from GFP is seen. (b) PCADK-NTA particles loaded with $NiCl_2$ show extensive association with GFP (Example 8, infra).

Figure 37:
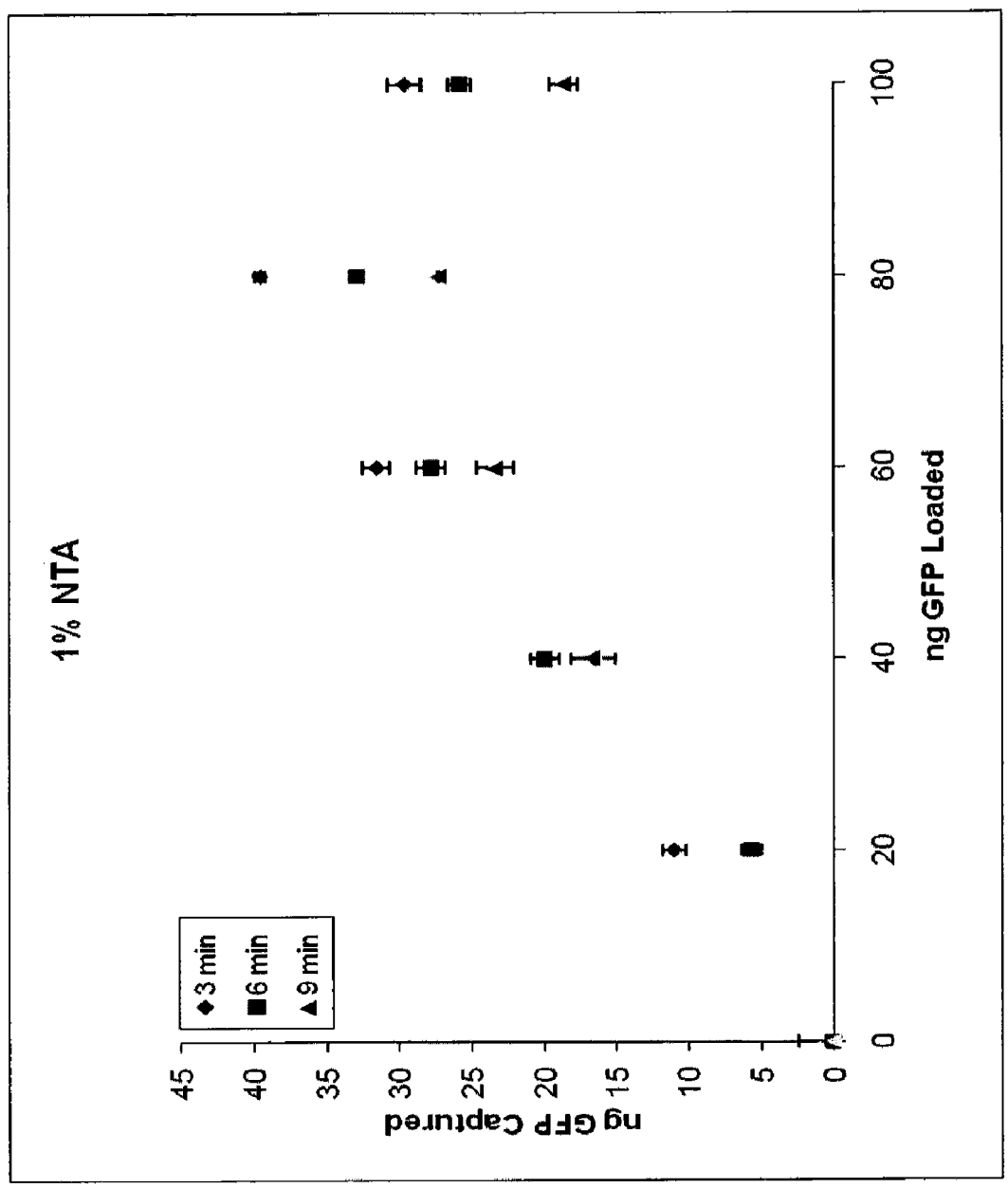

FIG. 37 is a graph of the Specific Binding curve for 1% NTA-PCADK particles (On-particle ELISA). 1% NTA-PCADK particles were charged with Ni and loaded with varying concentrations of His-tagged GFP. After extensive washing after GFP loading, horseradish peroxidase (HRP) conjugated GFP antibody (A-GFP Ab) was incubated with the particles (particles suspended at 1 mg particles/ml of PBS-T with a 1:5000 dilution of α-GFP Ab and 1% goat serum) for 2 h at room temperature. Particles were then washed with 3 volumes of PBS-T. Colorimetric determination of HRP activity was done on a plate reader with different amounts of particle per well. 1-step Slow TMB-ELISA substrate (3,3',5,5'-tetramethylbenzidene, Pierce) was used at a substrate and absorbances measured at 370 nm. Readings from 3, 6, and 9 min were compared and shown above. Specific binding curve suggests that 1% NTA particles saturate with GFP when loaded with 60 ng GFP/mg particle (Example 8, infra)

Figure 38:
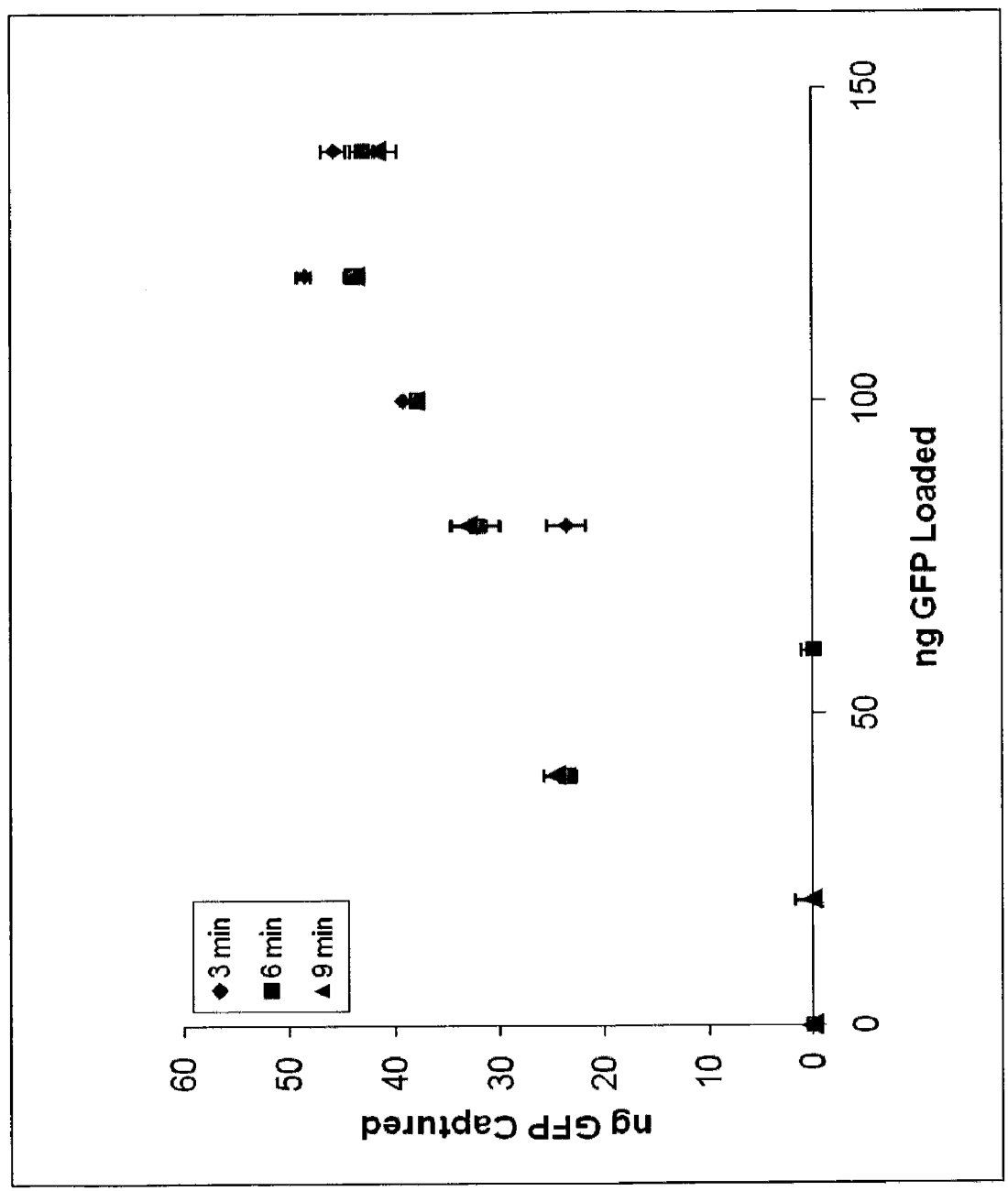

FIG. 38 is a graph of the Specific Binding curve for 10% NTA-PCADK particles (On-particle ELISA). 10% NTA-PCADK particles were charged with Ni and loaded with varying concentrations of His-tagged GFP. After extensive washing after GFP loading, horseradish peroxidase (HRP) conjugated GFP antibody (α-GFP Ab) was incubated with the particles (particles suspended at 1 mg particles/ml of PBS-T with a 1:5000 dilution of α-GFP Ab and 1% goat serum) for 2 h at room temperature. Particles were then washed with 3 volumes of PBS-T. Colorimetric determination of HRP activity was done on a plate reader with different amounts of particle per well. 1-step Slow TMB-ELISA substrate (3,3',5,5'-tetramethylbenzidene, Pierce) was used at a substrate and absorbances measured at 370 nm. Readings from 3, 6, and 9 min were compared and shown above. Specific binding curve suggests that 10% NTA particles saturate with GFP when loaded with 120 ng GFP/mg particle (Example 8, infra).

Figure 39:
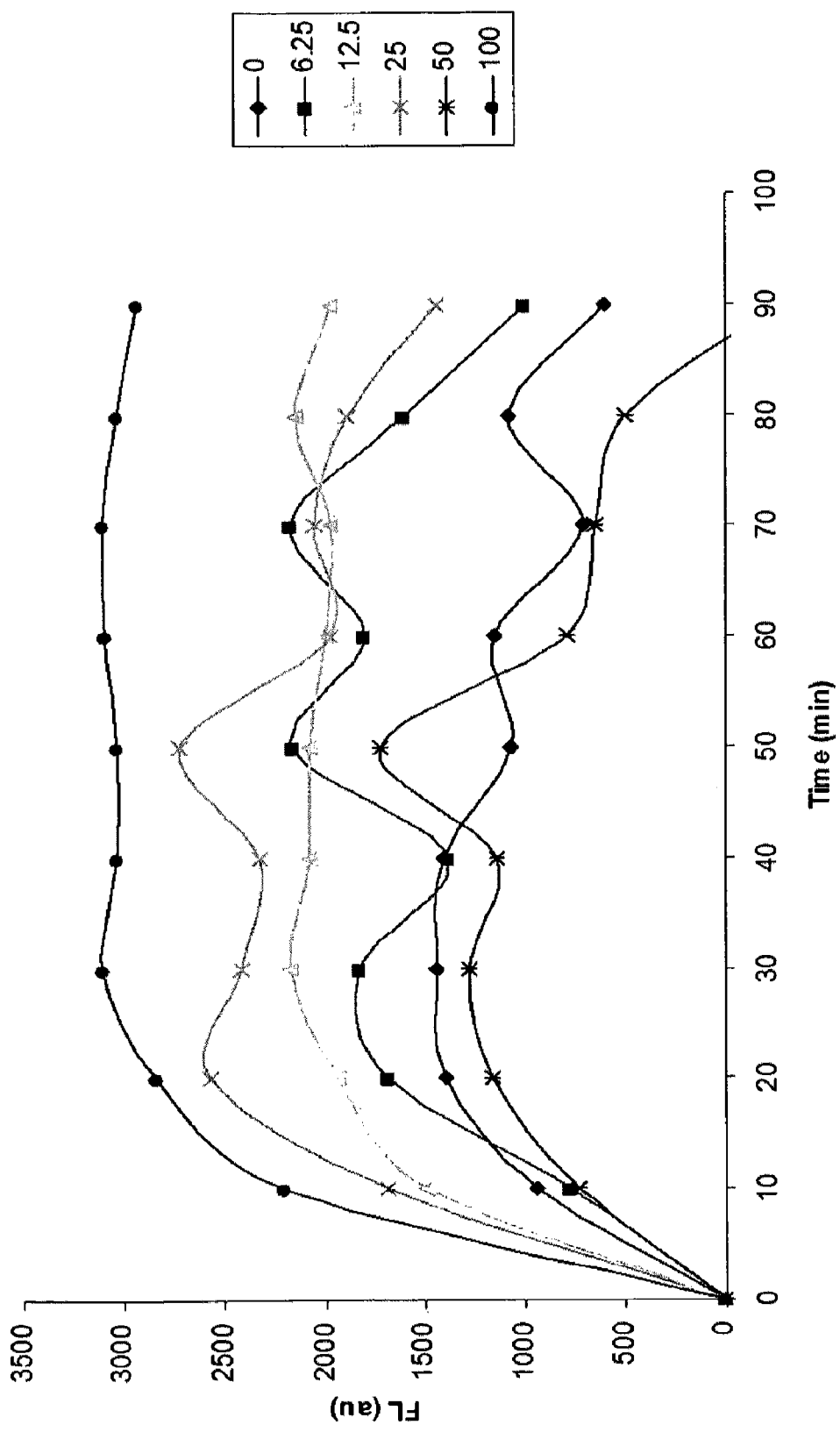

FIG. 39 is a graph showing that GFP Binding is reversible. Particles loaded with GFP were subjected to an spike of imidazole (200 mM final concentration), a competitive binding ligand to the NTA-Ni complex, and the fluorescence intensity of the supernantant measured as a function of time. Data suggests that GFP is maximally dissociated at 30 minutes in the presence of 200 mM imidazole (Example 8, infra).

Figure 40:
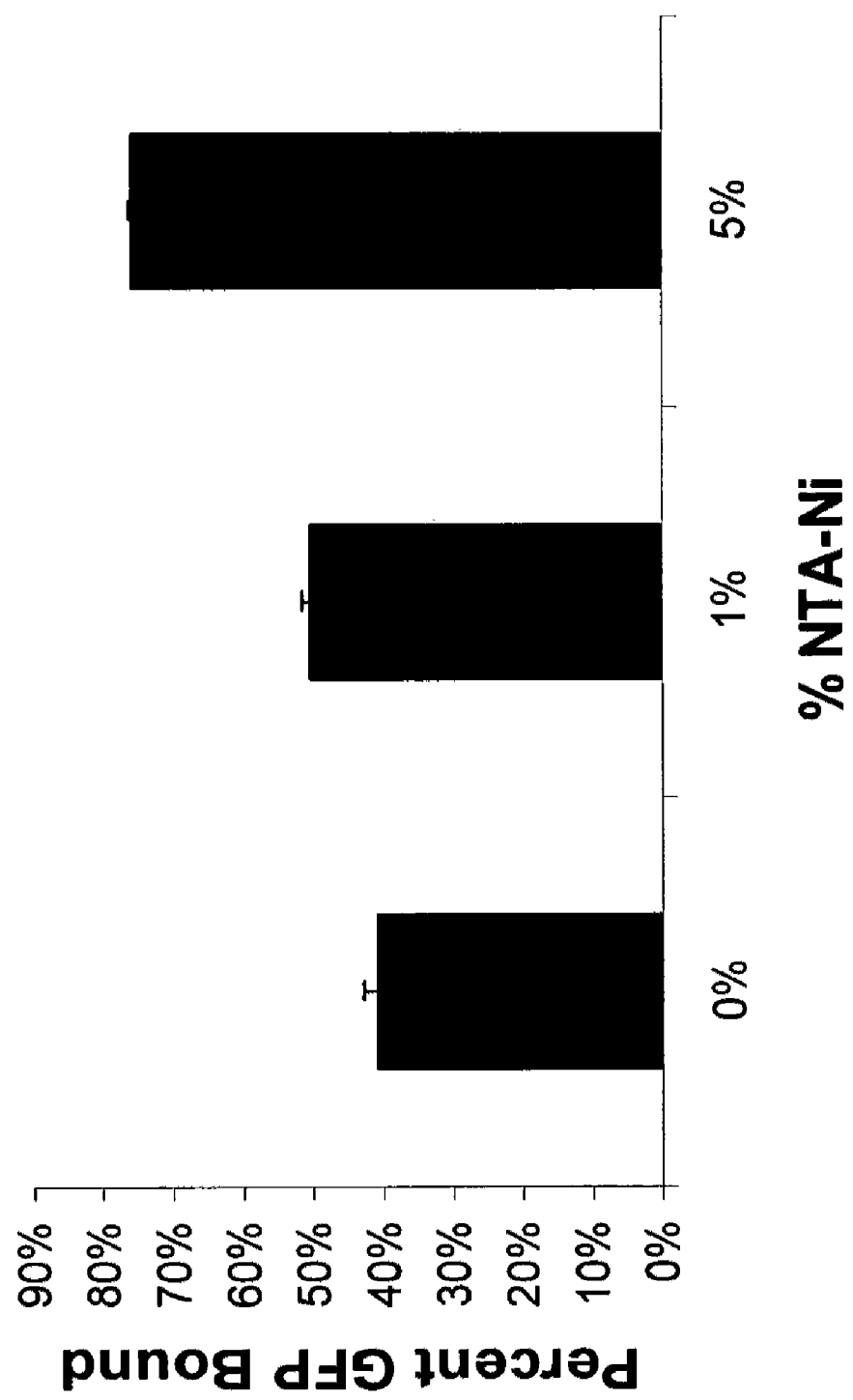

FIG. 40 is a chart showing that GFP binding increases with amount of NTA-Ni (Example 8, infra).

Figure 41:
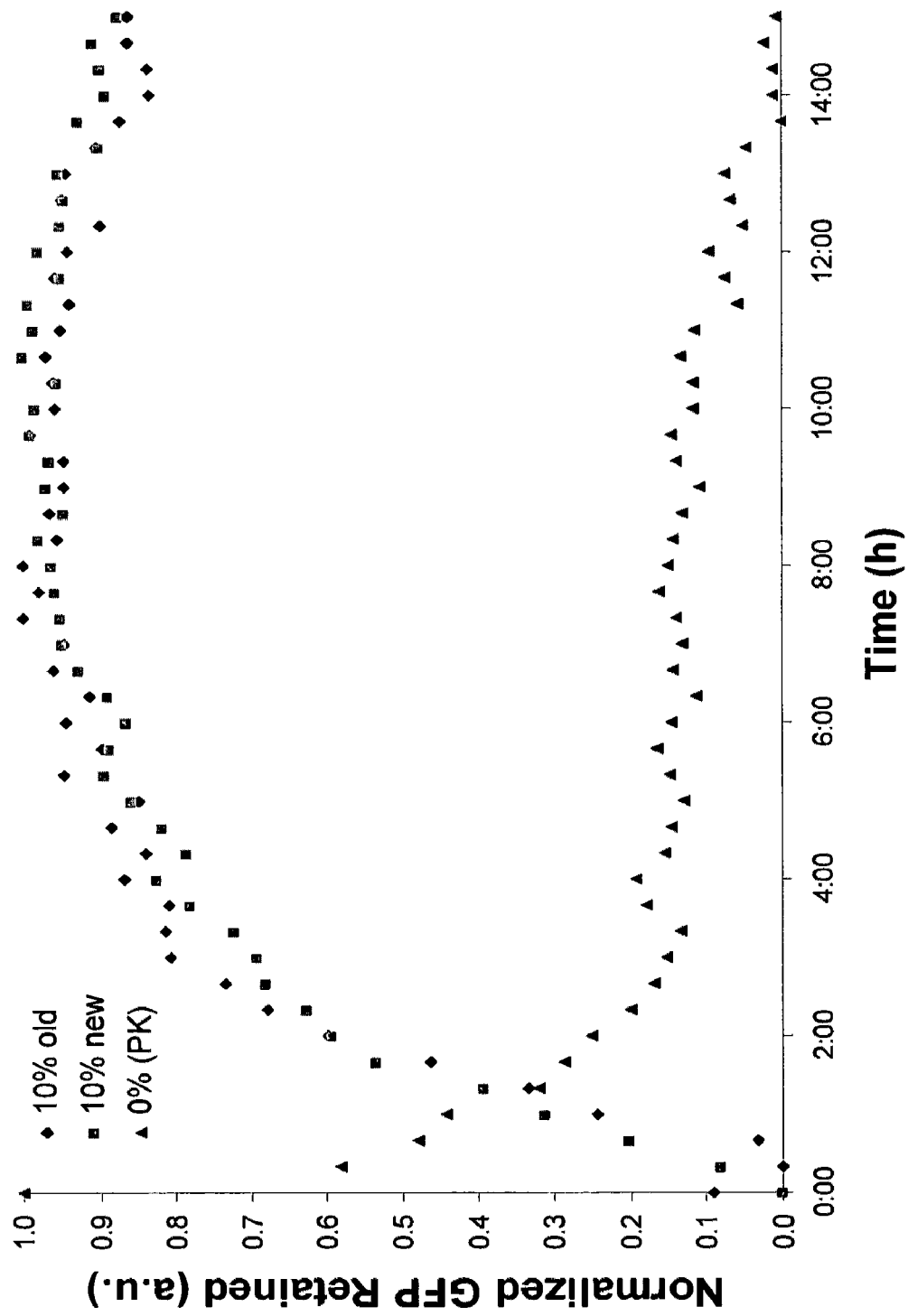

FIG. 41 is a graph showing that His-GFP stably bound to NTA-Ni for at least 15 hours (Example 8, infra).

DETAILED DESCRIPTION OF THE INVENTION

Definitions

All scientific and technical terms used in this application have meanings commonly used in the art unless otherwise specified. As used in this application, the following words or phrases have the meanings specified.

As used herein, the term "micelle" refers to a colloidal aggregate of polymer molecules having at least two different moieties which are linked to different properties in a liquid medium. The difference in the properties can occur due to different hydrophobicity/hydrophilicity, polarity, charge or charge distribution or other parameters which influence the solubility of a molecule. Micelles of the present invention are distinguished from and exclude liposomes which are composed of bilayers.

As used herein, the term "polymer" refers to a covalently linked arrangement of monomeric molecules. The arrangement can be realized in a linear chain or in a branched form. The polymer can be a homopolymer which is composed of only one type of monomeric molecules, or it can be a copolymer wherein two or more different types of monomers are joined in the same polymer chain. When the two different monomers are arranged in an alternating fashion, the polymer is called an alternating copolymer. In a random copolymer, the two different monomers may be arranged in any order. In a block copolymer each type of monomer is grouped together. A block copolymer can be thought of as two or more homopolymers joined together at the ends. When chains of a polymer made of one monomer are grafted onto a polymer chain of a second monomer a graft copolymer is formed.

As used herein, the term "particle" or "three-dimensional particle" refers to e.g., nanoparticles and/or microparticles. According to standard definitions, the term "nanoparticle" covers only particle having at least one dimension smaller than 100 nm.

Larger particles which do not fulfill this requirement are termed "microparticles". The present invention provides three-dimensional particles sized on the nanometer (nm) and micron (μm) scale. The particles of the invention can range in size from about 50 nm to 1000 μm or from about 200 nm to 600 μm.

The terms "ketals" and "diols" as used herein encompass ketals and diols comprising alkyl, cycloalkyl and aryl groups. "Alkyl group" or "aliphatic group" as used herein, is linear or branched chain alkyl group. In one embodiment a linear alkyl group is preferred. Also included within the definition of alkyl are heteroalkyl groups, wherein the heteroatom can be nitrogen, oxygen, phosphorus, sulfur and silicon.

The term "cycloalkyl group" or "cycloaliphatic group", as used herein describes a ring-structured alkyl including at least three carbon atoms in the ring. In one embodiment, a cycloalkyl group having 5 or 6 carbons is preferred. The cycloalkyl group also includes a heterocyclic ring, wherein the heteroatom can be nitrogen, oxygen, phosphorus, sulfur and silicon.

"Aryl group" or "aromatic group" as used herein, is an aromatic aryl ring such as phenyl, heterocyclic aromatic rings such as pyridine, furan, thiophene, pyrrole, indole and purine, and heterocyclic rings with nitrogen, oxygen, sulfur or phosphorus. Included in the definition of alkyl, cycloalkyl and aryl groups are substituted alkyl, cycloalkyl and aryl groups. These groups can carry one or more substitutions. Suitable substitution groups include but are not limited to, halogens, amines, hydroxyl groups, carboxylic acids, nitro groups, carbonyl and other alkyl, cycloalkyl and aryl groups.

In order that the invention herein described may be more fully understood, the following description is set forth.

Compositions of the Invention
Polyketal Polymers of the Invention

The present invention provides biodegradable hydrophobic polyketal polymers comprising multiple ketal groups, each ketal group having two oxygen atoms within the polymer backbone. In one embodiment, the biodegradable hydrophobic polyketal polymer of the invention is in the form of a solid molecule.

Examples of suitable ketal groups include, but are not limited to, 2,2-dioxypropyl group, 2,2-dioxybutyl group, 1,1-dioxycyclohexyl group or dioxyacetophenyl group. Also in the scope of the invention are ketal polymers including aliphatic, cycloaliphatic or aromatic ketals containing one or more hetero-atom, such as nitrogen, sulfur, oxygen and halides.

In one embodiment of the invention, the polymer further comprises a compound comprising alkyl, aryl, and cycloalkyl groups. In this embodiment, the compound may be directly attached to the ketal group.

Examples of suitable alkyl groups include, but are not limited to, methyl, ethyl and butyl groups. Examples of suitable aryl groups include, but are not limited to, substituted or unsubstituted benzyl, phenyl or naphtyl groups, such as, for example, a 1,4-dimethylbenzene. Examples of suitable cycloalkyl groups include, but are not limited to, substituted or unsubstituted cyclohexyl, cyclopropyl, cyclopentyl groups, such as, for example, 1,4-dimethylcyclohexyl group.

In a preferred embodiment, the polymer may be poly(1,4-phenylene-acetone dimethylene ketal). This polymer can be synthesized of 2,2-dimethoxypropane and 1,4-benzene dimethanol. The polymer may also be a poly(1,4-cyclohexane-acetone dimethylene ketal), which can be synthesized of 2,2-dimethoxypropane and 1,4-cyclohexane dimethanol.

In another embodiment, the polymer is poly(cyclohexane-1,4-diyl acetone dimethylene ketal) (PCADK). PCADK is made from cyclohexane dimethanol and degrades in an acid sensitive manner into cyclohexane dimethanol and acetone. The ketal linkages in PCADK hydrolyze on the order of weeks under physiologic pH conditions. At the phagosomal pH of 4.5, the ketal linkages of PCADK are approximately 30% hydrolyzed after 10 days.

In further embodiment of the invention, the polyketal polymer can be any one or more of PK1, PK2, PK3, PK4, PK5 and PK6 copolymers. These six polyketal copolymers exhibit varied hydrolysis kinetics at different pH levels. For example at pH 4.5, PK4 is the fastest out of the six copolymers to hydrolyze with PK3 having the second faster hydrolysis rate. In turn, PK3 has faster hydrolysis kinetics than PK2 or PK5, while PK2 and PK5 have faster hydrolysis kinetics than PK1 or PK6. However, at pH 7.4, PK3 is hydrolyzed faster than PK4. By altering the copolymer percentage of the polyketals of the invention, the hydrolysis kinetics for controllable release of an active agent can be fine tuned.

In one embodiment, PK1 has a structure as shown in Table 1 (Example 7) and is made up of at least 2 different monomers i.e., repeating units such as random repeating units. In one example of PK1, one type of monomer is 1,4,-cyclohexanedimethoxy with an x value (i.e. percent component of the first monomer incorporated into the polymer) of about 98%, and the second type of monomer is 1,5-pentanedioxy with a y value (i.e. percent component of the second monomer incorporated into the polymer) of about 2%. The n value may be 3. In this embodiment, PK1 is synthesized from two types of starting compounds, namely, 1,4-cyclohexanedimethanol and 1,5-pentanediol. An IUPAC designation for PK1 is poly (cyclohexane-1,4-diyl acetone dimethylene ketal-co-1,5-pentane-acetone dimethylene ketal).

In one embodiment, PK2 has a structure as shown in Table 1 (Example 7) and is made up of at least 2 different monomers i.e., repeating units such as random repeating units. In one example of PK2, one type of monomer is 1,4,-cyclohexanedimethoxy with an x value (i.e. percent component of the first monomer incorporated into the polymer) of about 92%, and the second type of monomer is 1,5-pentanedioxy with a y value (i.e. percent component of the second monomer incorporated into the polymer) of about 8%. The n value may be 3. In this embodiment, PK2 is synthesized from two types of starting compounds, namely, 1,4-cyclohexanedimethanol and 1,5-pentanediol. An IUPAC designation for PK2 is poly (cyclohexane-1,4-diyl acetone dimethylene ketal-co-1,5-pentane-acetone dimethylene ketal.

In one embodiment, PK3 has a structure as shown in Table 1 (Example 7) and is made up of at least 2 different monomers i.e., repeating units such as random repeating units. In one example of PK3, one type of monomer is 1,4,-cyclohexanedimethoxy with an x value (i.e. percent component of the first monomer incorporated into the polymer) of about 87%, and the second type of monomer is 1,5-pentanedioxy with a y value (i.e. percent component of the second monomer incorporated into the polymer) of about 13%. The n value may be 3. In this embodiment, PK3 is synthesized from two types of starting compounds, namely, 1,4-cyclohexanedimethanol and 1,5-pentanediol. An IUPAC designation for PK3 is poly (cyclohexane-1,4-diyl acetone dimethylene ketal-co-1,5-pentane-acetone dimethylene ketal.

In one embodiment, PK4 has a structure as shown in Table 1 (Example 7) and is made up of at least 2 different monomers i.e., repeating units such as random repeating units. In one example of PK4, one type of monomer is 1,4,-cyclohexanedimethoxy with an x value (i.e. percent component of the first monomer incorporated into the polymer) of about 97%, and the second type of monomer is 1,4-butanedioxy with a y value (i.e. percent component of the second monomer incorporated into the polymer) of about 3%. The n value may be 2. In this embodiment, PK4 is synthesized from two types of starting compounds, namely, 1,4-cyclohexanedimethanol and 1,4-butanediol. An IUPAC designation for PK4 is poly (cyclohexane-1,4-diyl acetone dimethylene ketal-co-1,4-butane-acetone dimethylene ketal).

In one embodiment, PK5 has a structure as shown in Table 1 (Example 7) and is made up of at least 2 different monomers i.e., repeating units such as random repeating units. In one example of PK5, one type of monomer is 1,4,-cyclohexanedimethoxy with an x value (i.e. percent component of the first monomer incorporated into the polymer) of about 85%, and the second type of monomer is 1,6-hexanedioxy with a y value (i.e. percent component of the second monomer incorporated into the polymer) of about 15%. The n value may be 4. In this embodiment, PK5 is synthesized from two types of starting compounds, namely, 1,4-cyclohexanedimethanol and 1,6-hexanediol. An IUPAC designation for PK5 is poly (cyclohexane-1,4-diyl acetone dimethylene ketal-co-1,6-hexane-acetone dimethylene ketal).

In one embodiment, PK6 has a structure as shown in Table 1 (Example 7) and is made up of at least 2 different monomers i.e., repeating units such as random repeating units. In one example of PK6, one type of monomer is 1,4,-cyclohexanedimethoxy with an x value (i.e. percent component of the first monomer incorporated into the polymer) of about 87%, and the second type of monomer is 1,8-octanedioxy with a y value (i.e. percent component of the second monomer incorporated into the polymer) of about 13%. The n value may be 6. In this embodiment, PK6 is synthesized from two types of starting compounds, namely, 1,4-cyclohexanedimethanol and 1,8-octanediol. An IUPAC designation for PK6 is poly (cyclohexane-1,4-diyl acetone dimethylene ketal-co-1,8-octane-acetone dimethylene ketal).

The PK1-PK6 copolymers may be synthesized using the acetal exchange reaction by copolymerizing 1,4-cyclohexanedimethanol with either butanediol, pentanediol, hexanediol or octanediol. As shown in Table 1 of Example 7, infra, a PK1 was synthesized with monomer A (1,4-cyclohexanedimethanol) plus monomer B (1,5-pentanediol); a PK2 was synthesized with monomer A (1,4-cyclohexanedimethanol) plus monomer B (1,5-pentanediol); a PK3 was synthesized with monomer A (1,4-cyclohexanedimethanol) plus monomer B (1,5-pentanediol); a PK4 was synthesized with monomer A (1,4-cyclohexanedimethanol) plus monomer B (1,4-butanediol); a PK5 was synthesized with monomer A (1,4-cyclohexanedimethanol) plus monomer B (1,6-hexanediol); a PK6 was synthesized with monomer A (1,4-cyclohexanedimethanol) plus monomer B (1,8-octanediol).

In another embodiment of the invention, the PK1, PK2, PK3, PK4, PK5 and PK6 copolymers of the invention can be intermingled to change or fine tune the release rate profile for attached active agents. For example, a polyketal with fast hydrolysis kinetics (e.g., PK4 or PK3) can be mixed with a polyketal with slower hydrolysis kinetics (e.g., PK1 or PK6) and co-administered to a subject. The active agent joined to PK4 or PK3 will be released in a subject quickly to provide the subject with an immediate release (IR) dose of active agent, while the active agent joined to PK1 or PK6 will be released at a slower rate allowing a gradual or extended release (ER) of the active agent in the subject.

In an embodiment of the invention, the biodegradable hydrophobic polyketal polymers comprises (1) multiple ketal groups, each ketal group having two oxygen atoms within the polymer backbone and (1) a linker. The ketal groups may comprise a 2,2-dioxypropyl group.

Biodegradable Polyketal Particles of the Invention

The invention further provides biodegradable particles comprising the polyketal polymers of the invention. The sizes of the particles can vary. For example, biodegradable particles can be made at nanometer (nm) or micron (µm) scale e.g., to form nanoparticles or microparticles. The particles of the invention can range in size from about 50 nm to 1000 µm. In one embodiment, the particles range in size from about 200 nm to 600 µm. In another embodiment, the particles range in size from about 1 µm to 10 µm, 10 µm to 20 µm, 20 µm to 30 µm, 30 µm to 40 µm or 40 µm to 50 µm. In yet another embodiment, the particles range in size from about 1 µm to 50 µm. A preferred particle size is between about 50 and 1000 nm, more preferred between about 200 and 600 nm. Another preferred particle size is about 30 µm.

The preferred size of a suitable polyketal polymer to form the biodegradable particle is between about 0.5 kDa and about 2 MDa, more preferred between 1 and about 150 kDa, most preferred between about 4 and about 6 kDa. In accordance with the invention, the number of the monomers in the polymer can range from about 2 to about 20,000, preferably about 10 to about 1,000, more preferably about 10 to about 50.

Polyketal polymers of the invention hydrolyze in aqueous solutions into low molecular weight, water soluble alcohols and ketones. For example, the degradation of poly(alkyl-acetone dimethylene ketal) is acid sensitive, with a half-life of 102.0 h at pH 7.4 and 35.0 h at pH 5.0. The advantage of a ketal linkage in the backbone is that it degrades under acidic conditions of phagosomes, within 1-2 days at pH 5.0. Polyketals can therefore also be used for targeting the acidic environments of tumors, inflammation and phago-lysosomes. The degradation also does not generate acidic degradation products. Thus, the ketal polymers are suitable for biological use.

In accordance with the practice of the invention, the polyketal polymer particles can further comprise one or more active agents.

In one embodiment of the invention, the biodegradable particle of the invention comprises: (a) a biodegradable hydrophobic polyketal polymers comprising multiple ketal groups, each ketal group having two oxygen atoms within the polymer backbone and (b) a linker. Suitable polymers to form the particles of the invention include PCADK and PK1-PK6.

In one embodiment of the invention, the polyketal polymer particle can further comprise one or more linkers which can bind an active agent. Multiple linkers of the same or different types can be attached to a polymer particle. The linkers are attached to the surfaces of the particles i.e., the linkers are exposed to the solvent or aqueous solution surrounding the particles.

In one embodiment, the biodegradable particle of the invention comprises (a) one or more of PK1, PK2, PK3, PK4, PK5 or PK6 (which can optionally comprise a linker), and (b) an active agent. In another embodiment of the invention, the biodegradable particle of the invention comprises (a) PCADK (which can optionally comprise a linker) and (b) an active agent.

In accord with the practice of the invention, the particles can comprise a single population of polyketals or a mixed population.

Active Agents of the Invention

As used herein, the term "active agent" refers to a protein, peptide, nucleic acid (DNA or RNA) or organic molecule, and other synthetic nucleic acid molecules, siRNA molecules, or antisense molecules. The active agent can be a therapeutic, prophylactic or diagnostic agent. The therapeutic agent can be an immunomodulatory agent such as specific ligands for RIG-I or TLRs, or C-type lectins (such as dectin-1 and DC-SIGN) or caterpillar proteins, or combinations of specific TLR ligands, or synthetic molecules or siRNAs which inhibit regulatory signaling networks with DCs and macrophages. The active agent can further include proteins (e.g. recombinant proteins), peptides, carbohydrates, nucleic acids, small molecules (e.g., kinase inhibitors, phosphatase inhibitor, cytokine inhibitors, small molecule antioxidant mimetics, receptor blockers, cytoskeletal rearrangement inhibitors, small molecule receptor activators.), imaging agents, vaccine antigens, DNA vaccines, or vaccines themselves, such as the influenza vaccine. Finally, an active agent can comprise antibodies that target, stimulate, modulate or inhibit subsets of DCs including Langerhans cells, dermal DCs, myeloid DCs, interstitial DCs, plasmacytoid DCs, or subsets of monocytes, and macrophages. Thus surface of these particles can be modified to contain targeting groups such as, for example, antibodies against subsets of dendritic cells, or proteins which stimulate subsets of dendritic cells, or macrophages such as CD40L, DEC-205, CD11c, langerin, MARCO, 33D1 etc.

Examples of suitable active agents include, but are not limited to: (1) agonists and antagonists of TLRs (e.g., TLR-2, TLR-3, TLR-4, TLR-5, TLR-7, TLR-8, TLR-9, TLR-10, and TLR-11), (2) agonists and antagonists of the receptor(s) activated by schistosome egg antigen (SEA), (3) molecules that stimulate or inhibit the expression or activity of a component of an intracellular signaling pathway that transduces the signal generated by activation of either of these types of receptors, (4) agents that stimulate or inhibit a transcription factor that is induced or stabilized by one or more of these signaling pathways, and (5) inhibitors of a regulatory pathway(s) within dendritic cells, macrophages or antigen-presenting cells.

Examples of agonists include, but are not limited to, peptidoglycans (O. Takeuchi, et al., 1999 Immunity 11:443-451) or zymosans (Dillon et al, 2006 *J. Clin. Invest.* 116(4):916-28). A. Ozinsky, et al., 2000 Proc. Natl. Acad. Sci. USA 97:13766-13771). The agonists also include bacterial lipopeptides (e.g., diacylated and triacylated lipopeptides), lipoteichoic acid, lipoarabinomannan, phenol-soluble modulin, glycoinositolphospholipdis, glycolipids, porins, atypical LPS from *Leptospira* interrogns or *Porphyromonas gingivalis*, or HSP70 (for a review see K Takeda, et al., 2003 Annu. Rev. Immunol. 21:335-376). The agonists can be isolated and/or highly purified molecules. The agonists include whole molecules or fragments thereof, or naturally-occurring or synthetic. Examples include, but are not limited to, a non-toxic form of cholera toxin (Braun et al., *J. Exp. Med.* 189: 541-552, 1999), certain forms of *Candida albicans* (d'Ostiani et al., *J. Exp. Med.* 191:1661-1674, 2000), or *P. gingivalis* LPS (Pulendran et al., *J. Immunol.* 167:5067-5076, 2001).

Examples of bacterial lipopeptides include bacterial cell wall lipopeptides which differ in their fatty acid chain of the N-terminal cysteines, such as diacylated and triacylated lipopeptides. For example, diacylated lipopeptides include Macrophage Activating Lipopeptide 2 kilo-Dalton from *Mycoplasma fermentans* or fragments thereof or synthetic analogues (e.g., MALP2, Pam2CSK4, Pam2CGNNDESNISFKEK, (SEQ ID NO:2), and Pam2CGNNDESNISFKEK-SK4(SEQ ID NO:3)). The triacylated lipopeptides include Pam3cys {S-[2,3-bis (palmitoyloxy)-(2-RS)-propyl]-N-palmitoyl-R-Cys-S-Ser-Lys4-OH)} (Takeuchi, et al., 2001 International Immunology 13:933-940).

In an embodiment, the agonist specifically effects TLR-2 or a receptor(s) bound by SEA (with respect to SEA, see MacDonald et al., *J. Immunol.* 167:1982-1988, 2001). Here too, the agonist can be, but is not limited to, a natural ligand, a biologically active fragment thereof, or a small or synthetic molecule. Other useful agonists may include a non-toxic form of cholera toxin (Braun et al., *J. Exp. Med.* 189:541-552, 1999), certain forms of *Candida albicans* (d'Ostiani et al., *J. Exp. Med.* 191:1661-1674, 2000), or *Porphyromonas gingivalis* LPS (Pulendran et al., *J. Immunol.* 167:5067-5076, 2001). These agents fail to induce IL-12(p70) and stimulate Th2-like responses.

The agonists can be agonists of TLR-4 (which bias the immune response toward the Th response, e.g. TH1) include Taxol, fusion protein from Rous sarcomavirus, envelope proteins from MMTV, Hsp60 from *Chlamydia pneumoniae* or Hsp60 or Hsp70 from the host. Other host factors that agonize TLR-3 include the type III repeat extra domain A of fibronectin, oligosaccharides of hyaluronic acid, polysaccharide fragments of heparan sulfate, and fibrinogen. A number of synthetic compounds serve as agonists of TLR-7 (e.g., imidazoquinolin (imiquimod and R-848), loxoribine, bropirimine, and others that are structurally related to nucleic acids).

Additional examples of suitable active agents include inhibitors of ERK, c-Fos, Foxp3, PI3 kinase, Akt, JNK, p38, NF-Kb, STAT 1, STAT2, IRF3, IRF7, IFN-alpha signaling or combinations thereof. Suitable active agents can further include inhibitors of SOCS1-7 proteins. Such inhibitors can be a small molecule, or a peptide, protein or nucleic acid (e.g., siRNA or antisense).

The agonist can be an exogenous or endogenous ligand, many of which are known in the art. The novel screening methods described below, particularly those that feature detecting TLR binding or activation, can be used to identify other ligands (whether naturally occurring molecules, fragments or derivatives thereof, antibodies, other peptides or protein-containing complexes, or synthetic ligands). For example, exogenous ligands of TLR-2 include LPS (lipopolysaccharide; a component of the outer membrane of Gram-negative bacteria), yeast-particle zymosan, bacterial peptidoglycans, lipoproteins from bacteria and mycoplasmas, and GPI anchor from *Trypanosoma cruzi*; endogenous ligands include heat shock (or "stress") proteins (e.g., an Hsp60 from, for example, a bacterial or mycobacterial pathogen) and surfactant protein-A. Exogenous ligands of TLR-3 include poly(I:C) (viral dsNRA); exogenous ligands of TLR-4 include LPS, and respiratory syncytial virus (endogenous ligands include stress proteins such as an Hsp60 or Hsp70, saturated fatty acids, unsaturated fatty acids, hyaluronic acid and fragments thereof, and surfactant protein-A). Flagellin is an exogenous ligand of TLR-5. CpG (cytosine-guanine repeat) DNA and dsDNA are exogenous and endogenous ligands, respectively, of TLR-9. See Zuany-Amorim et al., Nature Reviews 1:797-807, 2002, and Takeda et al., Ann. Rev. Immunol. 21:355-376, 2003.

Additional examples of suitable active agents include (a) an agent that inhibits the expression or activity of an AP-1 transcription factor in a dendritic cell, (b) a dendritic cell treated in culture with an agent that inhibits the expression or activity of an AP-1 transcription factor, or (c) syngeneic T cells stimulated in culture with dendritic cells treated as described in (b). The transcription factor can include c-fos, fos-B, Foxp3, or c-jun, and the agent that inhibits expression (of the transcription factor or of any component of the pathways described herein (these components are known in the art)) can be an antisense oligonucleotide or an RNAi molecule that specifically inhibits c-fos, fos-B, Foxp3, or c-jun expression (or the expression of a kinase, phosphatase, or other component of the signaling pathways). The inhibitory active agents discussed in the context of the present biodegradable particles can also be antibodies (or variants thereof (e.g., single-chain antibodies or humanized antibodies); preferably the antibodies are monoclonal antibodies).

In another embodiment, the active agent is an antagonist (e.g., inhibitor or suppressor) of an intracellular pathway that impairs TLR2 signaling or activation. The antagonists include gram negative LPS, Taxol, RSV fusion protein, MMTV envelope protein, HSP60, HSP70, Type III repeat extra domain A of fibronectin, oligosaccharides of hyaluronic acid, oligosaccharide fragments of heparan sulfate, fibrinogen and flagellin (for a review see K Takeda, et al., 2003 Annu. Rev. Immunol. 21:335-376).

In an additional embodiment, the active agent is an antagonist of an intracellular pathway that impairs SEA signaling or activation. In one other embodiment, the molecule is an antagonist of a JNK ½ pathway. In another embodiment, the molecule is CpG DNA which activates p38 and ERK (A-KYi, et al., 2002 The Journal of Immunolgy 168:4711-4720).

In another embodiment, the active agent is an inhibitor of ERK ½ which can inhibit maturation of dendritic cells and thus enhancing an IL12 and Th1 response. Examples of the molecule include but are not limited to PD98059 and U0126 (A. Puig-Kroger, et al., 2001 Blood 98:2175-2182).

In another embodiment, the active agent inhibits c-fos signaling thus enhancing an IL12 and Th1 response. Such molecules include a DEF domain mutant of c-fos or any polypeptide having a DEF domain mutation (L. O. Murphy, et al., 2002 Nature Cell Biology 4:556-564 and Supplementary information pages 1-3), including: rat Fra-1, and Fra-2; mouse FosB, JunD, c-Jun, c-Myc, and Egr-1; and human JunB, N-Myc, and mPer1.

Active agents can include nucleic acids such as DNA, RNA, anti-sense oligonucleotide or siRNA. Suitable examples of DNA include therapeutic genes. Examples of therapeutic genes include suicide genes. These are genes sequences, the expression of which produces a protein or agent that inhibits tumor cell growth or tumor cell death. Suicide genes include genes encoding enzymes, oncogenes, tumor suppressor genes, genes encoding toxins, genes encoding cytokines, or a gene encoding oncostatin. The purpose of the therapeutic gene is to inhibit the growth of or kill cancer cell or produce cytokines or other cytotoxic agents which directly or indirectly inhibit the growth of or kill the cancer cell.

Suitable oncogenes and tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), and nm23. Suitable toxins include Pseudomonas exotoxin A and S; diphtheria toxin (DT); E. coli LT toxins, Shiga toxin, Shiga-like toxins (SLT-1, -2), ricin, abrin, supporin, and gelonin.

Active agents can include enzymes. Suitable enzymes include thymidine kinase (TK), xanthine-guanine phosphoribosyltransferase (GPT) gene from E. coli or E. coli cytosine deaminase (CD), or hypoxanthine phosphoribosyl transferase (HPRT).

Active agents can include cytokines. Suitable cytokines include interferons, GM-CSF, interleukins, tumor necrosis factor (TNF) (Wong G, et al., Science 1985; 228:810); WO9323034 (1993); Horisberger M. A., et al., Journal of Virology, 1990 Mar., 64(3):1171-81; Li Y P et al., Journal of Immunology, Feb. 1, 1992, 148(3):788-94; Pizarro T. T., et al. Transplantation, 1993 Aug., 56(2):399-404). (Breviario F., et al., Journal of Biological Chemistry, Nov. 5, 1992, 267(31): 22190-7; Espinoza-Delgado I., et al., Journal of Immunology, Nov. 1, 1992, 149(9):2961-8; Algate P. A., et al., Blood, 1994 May 1, 83(9):2459-68; Cluitmans F. H., et al., Annals of Hematology, 1994 Jun., 68(6):293-8; Martinez O. M., et al., Transplantation, 1993 May, 55(5):1159-66.

Active agents can include Growth factors. Growth factors include Transforming Growth Factor-alpha. (TGF-alpha.) and beta (TGF-beta), cytokine colony stimulating factors (Shimane M., et al., Biochemical and Biophysical Research Communications, Feb. 28, 1994, 199(1):26-32; Kay A. B., et al., Journal of Experimental Medicine, Mar. 1, 1991, 173(3): 775-8; de Wit H, et al., 1994 Feb., 86(2):259-64; Sprecher E., et al., Archives of Virology, 1992, 126(1-4):253-69).

Active agents can further include the proteins catalase, superoxide dismutase, glutathione peroxidase, nitric oxide synthase.

The active agents of the invention can be can be naturally occurring, synthetic, or recombinantly produced, and includes, but are not limited to, any microbial or viral component or derivative thereof, including any component that is part of the structure of, or is produced by, the microbial cell or virus including, but not limited to, a cell wall, a coat protein, an extracellular protein, an intracellular protein, any toxic or non-toxic compound, a carbohydrate, a protein-carbohydrate complex, or any other component of a microbial cell or virus. The microbial cell or virus can be pathological.

Linkers of the Invention

The polyketals of the invention (e.g., in a particle embodiment) may further comprise one or more linkers. The linkers can be of the same type or can include a mixture of different types attached to the polyketal polymers. The linkers can be attached to the surfaces of the polyketal polymers e.g., the linkers can be exposed to the solvent or aqueous solution surrounding the particles.

The linker can range in size from 1-1000 nm or 100-200, 000 Da. In one embodiment of the invention, the linker can range in size from 1-10 nm, 10-50 nm, 50-100 nm, 100-200 nm, 200-300 nm, 300-400 nm, 400-500 nm, 500-600 nm, 600-700 nm, 700-800 nm, 800-900 nm and 900-1000 nm. In another embodiment of the invention, the linker can range in size from 100-10,000 Da, 10,000-50,000 Da, 50,000-100,000 Da, 100,000-150,000 Da and 150,000-200,000 Da. In yet another embodiment of the invention, the linker can be about 200-300 Da, 10,000 Da, 40,000 Da, 64,000 Da or 150,000 Da in size.

The linker can be a protein, polypeptide, nucleic acid or chemical compound. Examples of protein or polypeptide linkers include, but are not limited to, an amino acid sequence such as arginine-aspartic acid-glycine (RDG), hemoglobin, glutathione-S-transferase (GST), streptavidin or an antibody. Examples of nucleic acid linkers include, but are not limited to, RNA, DNA (e.g., ssDNA such as a 4 to 50 nucleic acid long tract of Poly A or Poly T sequence) or synthetic analogues. Examples of chemical compounds that can be used as linkers include, but are not limited to, polycarboxylic acid (e.g., polyacrylic acid) or chelating agents such as nitrilotriacetic acid (NTA) ligand, bipyradol and EDTA. Chelating agents bind to metal ions (e.g., nickel, zinc, copper, etc.) with the metal ions in turn facilitate binding of an active agent to the linker. The linker tethers or joins (e.g., via a noncovalent association) an active agent to the polyketal of the invention.

The linker can bind to active agents including, but not limited to, a protein, peptide, nucleic acid and/or carbohydrate. In one embodiment, the protein, peptide and/or carbohydrate further comprises a histidine tag. The histidine tag can comprise about 2-8 histidines. For example, in one embodiment, the histidine tag comprises about 6 histidines. The protein so bound to the linker can be a therapeutic, prophylactic or diagnostic protein.

In accordance with the practice of the invention, the therapeutic protein can be an immunomodulatory protein. For example, the immunomodulatory protein can include, but is not limited to: (a) a ligand for any of TLR 2, 3, 4, 5, 7, 8, 9, 10 and 11 or combination thereof, (b) an inhibitor of a regulatory pathway within dendritic cells, macrophages or antigen-presenting cells; and (c) a ligand for RIG-1, any C-type lectins including dectin-1 and DC-SIGN, or Caterpillar proteins The inhibitor of a regulatory pathway can include inhibitors of: (a) ERK, c-Fos, Foxp3, PI3 kinase, Akt, JNK, p38, NF-Kb, STAT 1, STAT2, IRF3, IRF7, IFN-alpha signaling; or (b) a SOCS 1, 2, 3, or other SOCS protein.

Additional suitable examples of proteins to bind to the linker include growth factors, cytokines, antioxidant enzymes, antibodies, erythropoietin (EPO), receptor ligand.

In one embodiment, a polyketal of the invention (e.g., PCADK or any of PK1 to PK6) comprises a NTA linker. The NTA linker can be loaded with nickel ions to produce a NTA-Ni linker that binds histidine tagged proteins.

Micelles of the Invention

The present invention further provides a biodegradable crosslinked micelle comprising multiple polymers of the invention. The polymers can be crosslinked by an external crosslinking agent. External crosslinking agents as used herein are agents which are not introduced into the polymer chain. The advantage of using of external agents is the faster crosslinking reaction compared to a reaction wherein only crosslinkable moieties within the polymer are used. The external crosslinking agent also reduces the probability that the encapsulated protein will be destroyed.

In one aspect of the present invention, suitable crosslinking agents are compounds which comprise at least two thiol groups. Examples of suitable crosslinking agents include, but are not limited to, ethylene glycol dithiol, aliphatic dithiols, dithiols which are connected by ketal linkages, and diamine containing molecules. The advantage of thiol groups is the sensitivity to reducing conditions, thus enabling an easy degradation of the micelle. Other crosslinking strategies include, but are not limited to, crosslinking by amines, esters, carbonates, thioesters, Schiff bases, vicinal diols, alkenes and alkynes, ketals, ketals orthoesters, thio-ketals, thio-orthoesters, sily-ketals, phenyl boronic acid-diol complexes, carbon-carbon bonds, sulfones, phosphate containing functional groups, azides, enzyme cleavable linkages, and urethanes, with Schiff bases, thiols and ketones being preferred in one embodiment of the present application (O'Reilly et al., 2005 *Chem. Mater.*, 17(24):5976-5988; Hanker et al., 2005 *Science* 309(5738):1200-05; Le, Z. et al., 2005 *Langmuir* 21(25): 11999-12006; Example 1, FIG. 9).

In another aspect of the present invention, the external crosslinking agent comprises an antigen. Examples of suitable antigens include, but are not limited to, proteins or peptides. The antigens can be naturally occurring, chemically synthesized or recombinantly made. Specific examples of suitable protein or peptide antigens include, but are not limited to, HIV antigens such as gp120 protein (or fragment thereof), TAT protein (or fragment thereof), NEF protein (or fragment thereof), HCV protein (or fragment thereof), and env protein (or fragment thereof). A preferred antigen includes a gp120 peptide antigen chemically synthesized and modified to contain four additional cysteine residues to create therein additional disulfide bonds. Any antigen having crosslinkable groups can be used. Antigens not having or having few crosslinkable groups can be modified (e.g., chemically modified) to comprise crosslinkable thiol groups, azides, alkynes, amines, maleimides, vinyl sulfones, ketones, hydrazines and thioesters.

Polymers to be used for micelle formation can be homopolymers or copolymers, such as block copolymers or graft polymers. Examples of suitable polymers include, but are not limited to, PEG block copolymers, such as PEG-polyamino acids, for example, PEG-polylysine, PEG-polyglutamic acid, PEG-polyaspartic acid or PEG-polyarginine; PEG-polyesters, PEG-polyurethane, PEG-PPO, modified or unmodified, PEG-polyacrylate or PEG-polymethacrylate, synthesized by atom transfer polymerization, where the PEG acts as an initiator. To facilitate polymer crosslinking, the polymer can be modified to include chemical groups including, but not limited to, amines, esters, carbonates, thioesters, Schiff bases, vicinal diols, alkenes and alkynes, ketals, ketals orthoesters, thio-ketals, thio-orthoesters, sily-ketals, phenyl boronic acid-diol complexes, carbon-carbon bonds, sulfones, phosphate containing functional groups, azides, enzyme cleavable linkages, and urethanes, with Schiff bases, thiols and ketones being preferred in one embodiment of the present invention. These groups can be introduced via chemical reactions known in the art, such as, among others, Michael addition or acylation (Example 1, FIG. 9). In one preferred embodiment the modified polymer is PEG-polylysine thiopyridal (FIG. 9).

The polymethacrylate or polyacrylate block can contain modifications to allow for assembly with vaccine components and crosslinking. For example a polyacrylate block can be a block copolymer consisting of polydimethylamino-acryalte-poly-glycidyl acrylate. Homopolymer of random copolymers composed of various acrylate or methacrylate monomers capable of forming micelles with vaccine components are also in the scope of the present invention.

In another aspect of the present invention the micelle can further comprise one or more active agents. Examples of suitable active agents are found herein, supra.

In accordance with the practice of the invention, the interaction between the micelle and the active agent can be electrostatic or hydrophobic or can occur due to hydrogen bond formation or molecular recognition depending on the type of polymer and agent. The surface of this micelle can be modified to contain targeting groups such as, for example, antibodies against dendritic cells, or proteins which stimulate subsets of dendritic cells, or macrophages such as CD40L, DEC-205, CD11c, langerin, MARCO, 33D 1 etc.

In one embodiment, the micelle is designed to deliver peptide antigens and immunomodulatory molecules to antigen-presenting cells (APCs). In this embodiment, the micelle comprises immunomodulatory molecules, peptide antigens and a copolymer. The peptide antigen acts as a crosslinker which allows the peptide antigen to be efficiently encapsulated into the peptide crosslinked micelles (PCMs) and also stabilizes them against degradation by serum components In another embodiment, the micelle can be used to encapsulate peptide or protein antigens together with immunomodulatory agents including multiple TLR ligands, or molecules such as synthetic compounds or siRNA that modulate signaling networks within cells (e.g., dendritic cells or other antigen presenting cells). The micelle targets dendritic cells and macrophages through their nanometer dimensions, as such cells robustly internalize nanometer sized materials, through phagocytosis. The micelles are crosslinked by crosslinking agents comprising disulfide linkages, which should stabilize them against decomposition induced by serum proteins. In the further embodiment of the invention, the micelle has a size of 5 to 50 microns.

In another embodiment, the polymers forming the micelle of the invention further comprise a linker. The linker allows for dual delivery of one or more active agents, via encapsulation of the active agents by the micelle or attachment to the micelle.

After phagocytosis, the biodegradable particles and micelles of the invention will break down, and the encapsulated material such as peptide or antigens, and immune stimulatory agents [e.g: ISS DNA, TLR 7/8, TLR 3 ligands such as ss RNA, TLR 2 ligands, and inhibitors of regulatory pathways such as the ERK, c-Fos or Foxp3 pathway], will be released into the dendritic cell, or macrophage, and the immunomodulatory agent will induce the antigen-presenting cells, to secrete a variety of cytokines. This combination of signals will result in the optimal activation of T cells, and inhibition of regulatory T cells and dendritic cells.

The micelles of the invention can include active agents such as vaccines composed of antigens from the relevant pathogen, together with immune modulatory agents [e.g: ISS DNA, TLR 7/8 ligands such as ss RNA, TLR 2 ligands, and inhibitors of regulatory pathways such as inhibitors of ERK, c-Fos or Foxp3, PI3 kinase, Akt, SOCS 1-7 proteins, or siRNA molecules or antisense molecules that inhibit such regulatory pathways]

The invention also provides methods for reversibly modifying proteins so that they have the appropriate charge to be encapsulated in the micelles. This strategy is based on reacting the amine groups of said protein with a compound, generating additional negative charges for every amine group, and rendering the protein negative. The modified protein will then be encapsulated in the micelle, crosslinked and then the pH will be reduced in order to remove the inserted compound form the protein. In one embodiment of the invention, the compound is amine groups is cis-aconityl. This group adds to negative charges to each amine group and can be released at ph 4.0.

Examples for targeting strategies include synthesizing a heterobifunctional PEG that has a DNA binding domain at one end and another end that can attached to a protein. This PEG chain is then attached to a protein and then assembled into a preformed micelles that contains immunostimulatory DNA. Examples of DNA binding domains include acridine or polyacridines. Examples of targeting ligands include galactose, mannose phosphate, mannose, peptides, and antibodies.

Further Modifications of the Biodegradable Particles and Micelles of the Invention The biodegradable particle or micelles can be further modified to incorporate antibodies or other molecules which target (1) specific receptors on particular subsets of DCs or macrophages or monocytes, including Langerhans cells, dermal DCs, myeloid DCs, plasmacytoid DCs or (2) specific receptors on antigen-presenting cells, such as DEC205, Langerin, DC-SIGN, dectin-1, 33D1, MARCO.

Pharmaceutical Compositions of the Invention

The present invention provides a pharmaceutical composition comprising the polymer (which can optionally comprise a linker) of the invention. In one embodiment, the present invention provides a pharmaceutical composition comprising the particle (which can optionally comprise a linker) of the invention. In another embodiment, the present invention provides a pharmaceutical composition comprising the micelle (which can optionally comprise a linker) of the invention. The polymer of the invention, whether in the form of a particle or micelle, can further comprise an active agent. For example, in one embodiment, the present invention provides a pharmaceutical composition comprising PCADK, PK1, PK2, PK3, PK4, PK5 and/or PK6 particles with a linker bound to an active agent.

Methods of the Invention

Methods of Producing the Particles and Micelles of the Invention

The invention provides methods for producing the particles of the invention. In one embodiment, the method comprises the steps of a) forming a hydrophobic polymer of a ketal and a diol or an unsaturated alcohol; b) forming a polymer particle of the polymer of a) in the presence of one or more active agents and thereby encapsulating the agent(s). Examples of suitable chemistries for forming the hydrophobic polymer of a ketal and a diol or an unsaturated alcohol include acetal exchange reaction using single or double emulsions and acyclic diene metathesis (Heffeman M J and Murthy N., 2005 *Bioconjug. Chem.* 16(6):1340-2; Jain R A., 2000 Biomaterials. 21(23):2475-90; Wagener K. B. and Gomez F. J., "ADMET Polymerization", in Encyclopedia of Materials: Science and Technology, E. J. Kramer and C. Hawker, Editors, Elsevier, Oxford, 5, 48 (2002)).

Suitable examples of ketals for this method include, but are not limited to, 2,2-dimethoxypropane, 2,2-dimethoxybutane, 1,1-dimethoxycyclohexane or dimethoxyacetophenole. Also in the scope of the invention are ketal polymers including aliphatic, cycloaliphatic or aromatic ketals containing one or more hetero-atom, such as nitrogen, sulfur, oxygen and halides.

In accordance with the practice of the invention, the diol can be any of alkyl, aryl and cycloalkyl diols.

Suitable examples of diols include, but are not limited to, 1,4-benzenedimethanol, 1,4-cyclohexanedimethanol, 1,5-pentane diol, 1,4-butane diol or 1,8-octane diol.

In one embodiment, the invention provides a method for producing the particles of the invention comprising the steps of (a) forming PCADK polymer; and (b) forming a particle of PCADK in the presence of one or more active agents, thereby producing the particle of the invention. The PCADK polymer can optionally comprise a linker.

In one embodiment, the invention provides a method for producing the particles of the invention comprising the steps of (a) forming PK1, PK2, PK3, PK4, PK5 and/or PK6 polymer; and (b) forming a particle of one or more of PK1, PK2, PK3, PK4, PK5 and/or PK6 in the presence of one or more active agents, thereby producing the particle of the invention. The PK1-PK6 polymers can optionally comprise a linker.

The micelles can be produced in a two step process. First, the polymers of interest can be contacted with a liquid (polar or nonpolar liquid depending on the polymer to be used) under appropriate conditions so as to form a micelle. After micelle formation, the micelle can be crosslinked with an external crosslinking agent to produce the biodegradable micelle of the invention.

Methods for Using the Compositions of the Invention

The invention further provides methods for delivering the active agents of the invention, via the particles of the invention or the micelles of the invention, to a subject in order to, for example, deliver active agents so as to treat the subject suffering from a disease (e.g. alleviate symptoms associated with the disease) or disorder. The particles (e.g., made of PCADK, PK1, PK2, PK3, PK4, PK5 or PK6 polymer) or micelles may then be degraded or dissolved in the subject so as to release the active agent for delivery to the subject. The particles or micelles of the invention have variable degradation rates at various pH ranges and can be designed to release an active agent according to a desired profile. For example, particles formed from PK3 polymers would degrade and release an active agent faster than particles formed from PK6 polymers.

In one embodiment of the invention, the particles or micelles of the invention used for delivering active agents further comprise a linker. In a further embodiment, a particle formed of the PCADK polymer further comprises a linker (e.g., NTA) bound to an active agent is used for delivery of the active agent to a subject.

The disease or disorder suffered by the subject can be any of HIV, malaria, TB, SARS, anthrax, Ebola, influenza, avian influenza and HCV. Further disease or disorder can be any of an infectious disease, autoimmune disease, allergic disease, disorder or complications associated with transplantation, diabetes and cancer. Examples of autoimmune disease include lupus, rheumatoid arthritis, psoriasis, asthma and COPD.

The active agents are delivered through the particles of the invention by various administration means including, but not limited to, intravenous, subcutaneous, intramuscular, oral and inhalation means. The most effective mode of administration and dosage regimen for the compositions of the present invention depends upon the exact location of the disease or disorder being treated, the severity and course of the disease or disorder, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. Cancer Chemother., Rep. 50 (4):219-244 (1966). Adjustments in the dosage regimen maybe made to optimize the tumor cell growth inhibiting and killing response, e.g., doses may be divided and administered on a daily basis or the dose reduced proportionally depending upon the situation (e.g., several divided dose may be administered daily or proportionally reduced depending on the specific therapeutic situation). It would be clear that the dose of the compositions of the invention required to achieve treatment may be further reduced with schedule optimization.

As used herein, the term "subject" may include a human, any animal such as equine, porcine, bovine, murine, canine, feline, and avian subject, a cell or a cell tissue. In accordance with the practice of the invention the active agents can be delivered or administered to the subject (using the compositions of the invention) before, after, or during the onset of the disease or disorder.

The invention provides methods for regulating an immune response by administering active agents via the particles or micelles of the invention. In one embodiment of the invention, the particles or micelles used in the methods of the invention further comprise a linker. For example, in the methods of the invention, an immune response can be biased towards a Th immune response in a TLR-dependent manner by delivering or administering to a subject a particle or micelle of the invention containing a desired active agent. In one embodiment, a TLR-expressing cell is contacted with an agent (delivered by the particle or micelle of the invention) that effects a bias towards a Th immune response (e.g., a Th0, Th2 or T regulatory cell immune response). For example, the agent (e.g., a natural ligand, a biologically active fragment thereof, or a small or synthetic molecule) that activates TLR-2, ERK ½, or c-fos.

As noted above, the immune response can be regulated or modulated (e.g., increase biasing or decrease biasing toward a Th immune response) at a point in the signaling pathway downstream from receptor activation (e.g., downstream from TLR binding or downstream from TLR activation or recognition). Thus, the patient can also be treated with an active agent or combination of active agents (delivered using the compositions of the invention) that bias the immune response by acting intracellularly on the elements of the downstream signaling pathway.

The present invention provides methods for biasing towards a Th2 immune response by inducing cell signaling (e.g., activation) of any of the MAP kinase pathways, including an ERK ½ pathway using a desired active agent delivered using the compositions of the invention. An induced MAP kinase pathway can be characterized by an increase in the amount and/or duration of phosphorylated components of the MAP kinase pathways, including ERK ½.

In another embodiment of the methods of the invention, an active agent can be delivered, via the compositions of the invention, which modulates an ERK ½ MAP kinase pathway so as to regulate a TH2 immune response. In this embodiment, as an example, an agonist of a TLR (e.g., TLR-2) induces phosphorylation of ERK ½ so as to enhance a TH2 immune response. In yet another embodiment of the methods of the invention, an active agent can be delivered via the compositions of the invention so as to modulate a c-FOS pathway in the cell thereby regulating a TH2 immune response. In this embodiment, as an example, an agonist of a c-fos pathway induces expression of c-fos and/or phosphorylation of c-fos so as to enhance a TH2 immune response. Additionally, in yet a further embodiment of the methods of the invention, an active agent can be delivered via the compositions of the invention, so as to modulate a Th2 immune response by affecting TLR2 or its downstream signaling pathway elements such as ERK ½ MAP kinase pathway and a c-FOS pathway. For example, the active agent, delivered via the compositions of the invention, can be used to modulate production or activity of IL-10 (for example increase production or upregulate of IL-10).

In one embodiment, the methods for biasing towards a Th2 immune response includes decreasing or inhibiting signaling of p38 and/or JNK pathway(s) which mediate (e.g., inhibit) IL12 production and thus biasing against a Th1 response by administering an active agent delivered via the compositions of the invention. In another embodiment, the methods for biasing towards a Th2 immune response includes decreasing or inhibiting the amount of phosphorylated p38 and/or JNK, or decreasing or inhibiting the duration of phosphorylation of p38 and/or JNK which mediate (e.g., inhibit) IL12 production and thus biasing against a Th1 response by administering micelles or particles of the invention containing a desired active agent (or combination thereof).

The present invention also provides methods for biasing towards a Th1 immune response by inducing cell signaling (e.g., activation) of any of the MAP kinase pathways, including a p38 and/or JNK pathway by administering an active agent delivered via the compositions of the invention. An induced p38 and/or JNK pathway can be characterized by an increase in the amount and/or duration of phosphorylated components of the MAP kinase pathways, including p38, and/or JNK.

In one embodiment, the methods for biasing towards a Th1 immune response includes decreasing or inhibiting signaling of ERK ½ and/or c-fos pathway(s) by administering an active agent delivered via the compositions of the invention. In another embodiment, the methods for biasing towards a Th1 immune response includes decreasing or inhibiting the amount of phosphorylated ERK ½ and/or c-fos, or decreasing or inhibiting the duration of phosphorylation of ERK ½ and/or c-fos by administering an active agent delivered via the compositions of the invention.

Additionally, the invention provides methods for regulating a TH2 immune response which comprises contacting a T cell (e.g., a naïve T cell) with a TLR-positive cell (such as a DC) treated in culture with a TLR agonist (e.g., TLR-2 agonist), delivered via the compositions of the invention, which activates an ERK ½ pathway and/or which activates c-fos or c-fos pathway.

Additionally, the invention provides methods for regulating a TH1 immune response which comprises contacting a T cell (e.g., a naïve T cell) with a TLR-positive cell treated in culture with a TLR agonist (e.g., TLR-4 agonist), delivered via the compositions of the invention, which activates a p38 pathway and/or a JNK pathway.

The present invention provides methods for treating a subject having an immune-related condition or disease (e.g., allergies, autoimmune disease, and other immune-related conditions including cancer), comprising administering to the subject any of the agents of the invention, delivered via the compositions of the invention, in an amount effective to bias towards or against a Th1, Th2 or Th0 immune response. The subject can be bovine, porcine, murine, equine, canine, feline, simian, human, ovine, piscine or avian.

In one embodiment, a subject having a condition or disease associated with an exhuberant Th2 response is treated with an agent of the invention, delivered via the compositions of the invention, that activates cell signaling in the subject so as to bias towards a Th1 immune response. Disease characterized by exhuberant Th2 response include, but are not limited to allergy, asthma, and chronic obstructive pulmonary disease (COPD (e.g., emphysema or chronic bronchitis).

In another embodiment, a subject having a condition or disease associated with an exhuberant Th2 response is treated with a molecule that inhibits biasing towards a Th2 immune response, delivered via the compositions of the invention.

In one embodiment, a subject having a condition or disease associated with an exuberant Th1 response is treated with a agents of the invention, delivered via the compositions of the invention, that activates cell signaling in the subject so as to bias towards a Th2 immune response. Disease characterized by exhuberant Th1 response include, but are not limited to diabetes, rheumatoid arthritis, multiple sclerosis, psoriasis, and systemic lupus erythematosis.

In another embodiment, a subject having a condition or disease associated with an exuberant Th1 response is treated with an active agent, delivered via the compositions of the invention, that inhibits biasing towards a Th1 immune response.

The following examples are presented to illustrate the present invention and to assist one of ordinary skill in making and using the same. The examples are not intended in any way to otherwise limit the scope of the invention.

Advantages of the Invention

Polyketal particles of the invention comprise, or are capable of encapsulating, a wide range of active agents, from small inhibitors to large proteins, and can be used to delivery the active agents to a subject suffering from a disease or condition or as a preventative measure.

In one embodiment, the active agents joined to or encapsulated by the polyketals can retain activity for several weeks in a subject. Additionally, the polyketals with the active agents can be freeze-dried, and are capable of being stored for months without degradation. The polyketals have a controllable degradation profile at various pH ranges, and if necessary can be fine tuned for precision release of active agents.

The polyketal polymer of the invention should overcome problems associated with administering active agents into a subject. For example, after administration of the active agent by injection, the blood supply in areas surrounding the injection site makes it highly likely that active agents will be immediately carried away following injection. The larger, micron-scale polyketals of the invention should overcome this obstacle and allow the polyketals comprising or encapsulating active agents to remain in the local microenvironment.

The polyketals of the invention have several unique properties that make them ideal as a delivery vehicle of active agents for the treatment of a disorder or disease (e.g., myocardial treatment) or as a preventative measure: (1) they can degrade on a time scale that can be easily manipulated from 1-2 days to weeks at a variety of pH values; (2) they can hydrolyze into neutral excretable compounds, and should therefore cause less degradation and denaturation of proteins than polyester-based microparticles; (3) the polyketals can be solid particles and may be stable for extended periods after formulation; and (4) the properties of polyketals can be easily manipulated to alter particle size, shape and porosity.

In one embodiment of the invention, altering the copolymer percentage of the polyketals can change or fine tune the hydrolysis kinetics of the polyketals in order to provide controllable release of active agents joined to or encapsulated by polyketals. For example, the monomer composition of PK4 provides for faster hydrolysis kinetics than PK3 at pH 4.5. In turn, PK3 has faster hydrolysis kinetics than PK2 or PK5, while PK2 and PK5 have faster hydrolysis kinetics than PK1 or PK6. Thus, active agents joined to PK4 will be released faster than active agents joined to PK3; active agents joined to PK3 will be released faster than active agents joined to PK2 or PK5; and active agents joined to PK2 or PK5 will be released faster than active agents joined to PK1 or PK6.

In another embodiment of the invention, the polyketals of the invention can be mixed in order to change or fine tune the release rate for active agents joined to or encapsulated by polyketals. For example, a polyketal with fast hydrolysis kinetics (e.g., PK4 or PK3) can be mixed with a polyketal with slower hydrolysis kinetics (e.g., PK1 or PK6) and co-administered to a subject. The active ingredient joined to PK4 or PK3 will be released in a subject quickly to provide the subject with an immediate release (IR) dose of active agent, while the active agent joined to PK1 or PK6 will be released at a slower rate allowing a gradual or extended release (ER) of the active agent in the subject.

Another advantage of the invention is that in one embodiment, a linker can be attached to the polyketal polymer. The polyketal polymers may then be used to form particles or micelles with linkers. Particles or micelles with linkers allow dual delivery of one or more active agents to a subject, namely, via encapsulation of the active agents by the particle or micelle and attachment of the active agent to the particle or micelle to the linker. In one embodiment, this dual mode of delivery for active agents provides for dual release times for the active agents, with the linker bound active agents released faster than the encapsulated active agents.

The following examples are presented to illustrate the present invention and to assist one of ordinary skill in making and using the same. The examples are not intended in any way to otherwise limit the scope of the invention.

EXAMPLES

Example 1

Synthesis of Antigen Containing Crosslinked Micelles

Crosslinked micelles that contain the protein antigen Ovalbumin and immunostimulatory DNA were synthesized in a two step process. First, micelles were formed between the cationic block copolymer, PEG-polylysine-thiopyridal and negatively charged FITC-Ovalbumin (FITC-OVA) and immunostimulatory DNA (ISS-DNA). These micelles contained a 10 mg/ml concentration of PEG-polylysine-thiopyridal, a 0.5 mg/ml concentration of FITC-OVA and a 0.5 mg/ml concentration of ISS-DNA. The micelles were allowed to form for one hour and were then crosslinked with 0.4 mg/ml of dithio-ethylene glycol. The crosslinking reaction was monitored by U.V. activity (342 nm), and indicated that the thiopyridal groups had been quantitatively reacted after 1 hour at room temperature. The encapsulation efficiency of FITC-OVA in the micelles was determined by centrifuging the micelles through a 100 kD spin-filter (centricon) and analyzing the recovered solution for FITC fluorescence (excitation 494 nm, emission 510 nm). This indicated that over 95% of the FITC-OVA was encapsulated in the micelles.

Example 2

Synthesis of Polyketal Particles (Single Emulsion Method for Delivery of Hydrophobic Drugs)

Particles were synthesized with, poly(1,4-phenylene-acetone dimethylene ketal) using an oil-in-water emulsion method. Briefly, 10 mg of 2, 1 mg of the ERK inhibitor UO126 and 0.1 g of chloro-methyl fluorescein diacetate (CM-FDA), were dissolved in 0.5 mL of $CHCl_3$ (with 0.1% triethylamine). This solution was then added to 5 mL of pH 9 buffer (10 mM $NaHCO_3$) containing 2 mg/ml polyvinyl alcohol (PVA, 31-50 kDa, Aldrich). The oil-water mixture was shaken briefly and then sonicated for 2 to 3 min at 40 watts (Branson Sonifier 250) to form a fine oil/water emulsion. The emulsion was stirred under $N_2$ flow for at least 3 h to evaporate the solvent and produce a particle suspension. Particle sizes were analyzed by dynamic light scattering (DLS) and indicated that the average diameter was 282 nm.

Example 3

Synthesis of Polyketal Particles Encapsulating Ovalbumin (Double Emulsion Method for Synthesis of Hydrophilic Drugs)

Polyketal particles (PKNs) containing FITC-ovalbumin were fabricated using a double emulsion method. First, 20 mg of poly(1,4-phenylene acetone dimethylene ketal) (PPADK) dissolved in 500 μL of chloroform was added to 100 μL of FITC-Ova solution (~0.7 mg). This mixture was sonicated at 40 watts for 1 minute to form the primary emulsion. Next, 5 mL of 0.2% w/v polyvinyl alcohol (PVA, Aldrich) in 10 mM pH 9 sodium phosphate buffer was added, and this mixture was sonicated at 40 watts for at least 1 minute to form the secondary emulsion. The emulsion was mixed under nitrogen ventilation for 4 hours, after which the volume was made up to 5 mL with buffer. Two batches of PKNs containing FITC-Ova were prepared in this manner, as well as two batches of plain PKNs (without FITC-Ova). The PKN suspensions were stored at 4° C.

Particle sizing was determined by dynamic light scattering (DLS). The two batches of FITC-Ovalbumin-loaded PKNs had effective diameters of 426 nm and 462 nm, and the empty PKN batches were 321 nm and 347 nm.

Labeling of FITC-Ova

Chicken egg albumin (ovalbumin) was labeled with fluorescein as follows. Ovalbumin was dissolved at 10 mg/mL in 200 mM pH 9 $NaHCO_3$ buffer. Fluorescein isothiocyanate (FITC) was dissolved at 10 mg/mL in DMSO. Next, 2.5 mL of ovalbumin solution (25 mg, 0.56 mmol) was mixed with 50 μL of FITC/DMSO (0.5 mg, 1.28 mmol) for at least 1 hour at 30° C. The product was filtered in a Sephadex PD-10 column to remove the free dye; the column was loaded with 2.5 mL of product and was eluted with 2.5 mL water. The resulting ovalbumin concentration was approximately 7 mg/mL. The degree of labeling was calculated to be 1.09 by measuring the absorbance of FITC at 497 nm and using the estimated concentration of ovalbumin.

Determination of FITC-Ova encapsulation in PKNs

Figure 1:
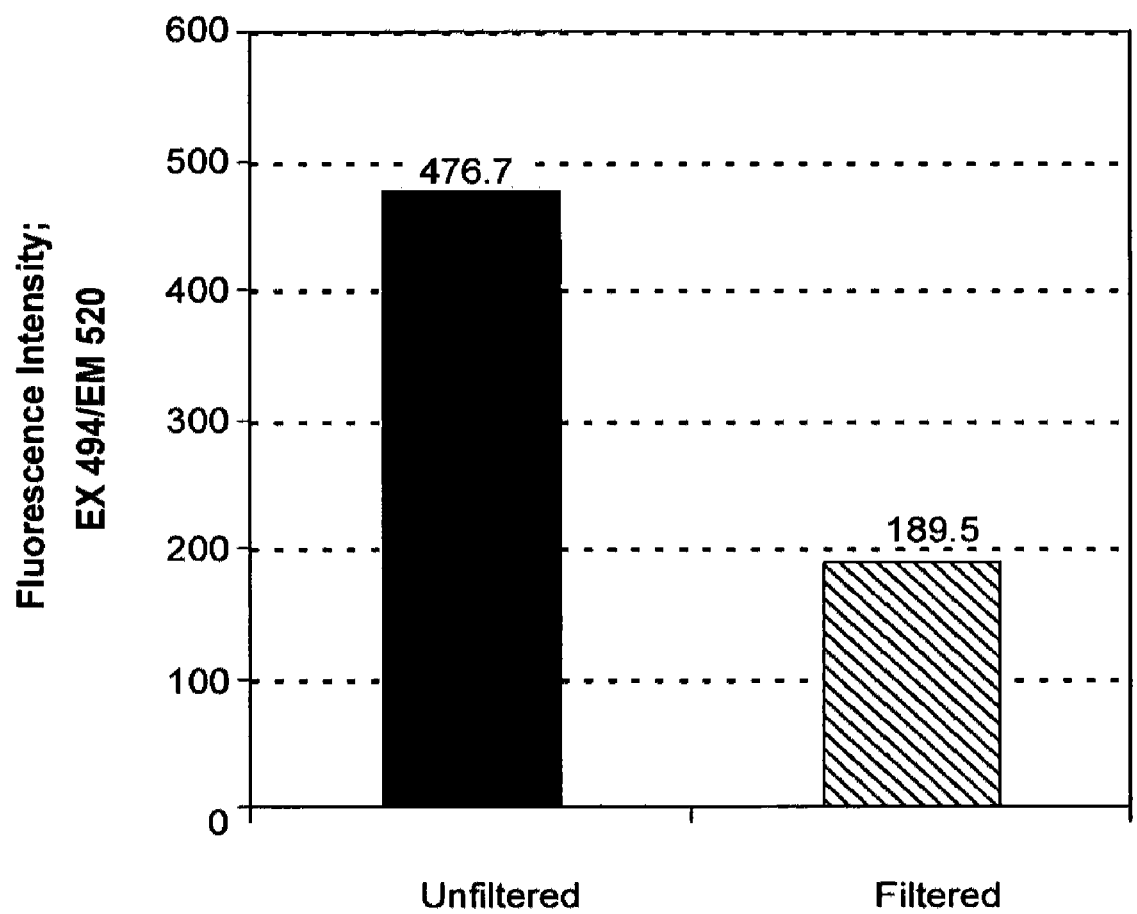
FIG. 1 is a bar graph showing the fluorescence intensity of filtered and unfiltered PKNs with FITC-Ova (excitation 494 nm, emission 520 nm). The data shown is the average of two samples. The FITC-Ova encapsulation efficiency is 60% (Example 3, infra).

The two FITC-Ova PKN batches were diluted by 5-fold in water, and a portion of each diluted sample was filtered through a 0.1 μm Supor syringe filter (Pall Acrodisc). The filtered and unfiltered samples were further diluted by 10-fold into pH 9 sodium phosphate buffer, and the fluorescence was measured with 494 nm excitation wavelength and 520 nm emission wavelength. (FIG. 1)

The encapsulation efficiency was calculated using the fluorescence intensity of the filtered and unfiltered samples, as follows:

$$EncapsulationEfficiency = \left(1 - \frac{Filtered}{Unfiltered}\right) \times 100\% = \left(1 - \frac{189.5}{476.7}\right) \times 100\% = 60\%$$

Example 4

Synthesis and Degradation of Ketal-Backbone Polymer (Polyketal)

FIG. 2 shows: (A) Ketal exchange reaction between 1,4-benzenedimethanol and 2,2-dimethoxypropane to produce the ketal intermediate 1. (B) Stepwise polymerization of 1 to produce polyketal 2. Reaction steps A and B are driven forward by distilling off the methanol byproduct. (C) Formation of drug-loaded particles by the solvent evaporation method. Particles exhibit pH-sensitive degradation into low molecular weight excretable compounds.

Synthesis

The Polyketals are synthesized via a new polymerization strategy based on the ketal exchange reaction (14). This reaction is generally used to introduce protecting groups onto low molecular weight alcohols and has not been used previously to synthesize polymers. However, we demonstrate here that the ketal exchange reaction can be used to synthesize an acid sensitive polymer by simply reacting 2,2-dimethoxypropane (DMP) with a diol. We propose that the polymerization occurs through the reaction mechanism in FIG. 2. The ketal exchange reaction is an equilibrium reaction involving protonation of DMP followed by nucleophilic attack by the alcohol. This equilibrium is shifted toward formation of the ketal intermediate 1 by distilling off the methanol byproduct. As the reaction proceeds, molecules of 1 combine in a stepwise manner to form polyketal 2.

A representative polymerization of DMP and 1,4-benzenedimethanol (BDM) gave the polyketal 2 with a 48% yield. The polymerization was carried out in a 25 mL two-necked flask connected to a short-path distilling head. BDM (1.0 g, 7.3 mmol, Aldrich) dissolved in 10 mL warm ethyl acetate was added to 10 mL distilled benzene kept at 100° C. Recrystallized p-toluene sulfonic acid (5.5 mg, 0.029 mmol, Aldrich) dissolved in 550 µL ethyl acetate was then added. After allowing the ethyl acetate to distill off, distilled DMP (900 µL, 7.4 mmol, Aldrich) was added to initiate the reaction. Additional doses of DMP were added via a metering funnel, with each dose consisting of 2 mL benzene plus 300 to 500 µL DMP. Each dose was added over a 30 to 40 min period with a 30 min interval in between. The total duration of the reaction was 7 h. The reaction was stopped with the addition of 100 µL triethylamine and was precipitated in cold hexanes. The crude product was vacuum filtered, rinsed with ether and hexanes, and vacuum dried to yield 600 mg of white solid product (48% yield). The recovered polymer was analyzed by GPC and $^1$H NMR.

FIG. 3A shows the GPC trace from one batch in which $M_w$=4000 was obtained, corresponding to a degree of polymerization of 22.5 repeating units, with a polydispersity index of 1.54. The $^1$H NMR spectrum (FIG. 3B) confirms that the repeating unit of 2 contains a dimethyl ketal group ('6a'). Together, the GPC and $^1$H NMR data provide evidence for the successful synthesis of polyketal 2.

Hydrolysis

The hydrolysis kinetics of 2 were measured at pH values corresponding to lysosomes (pH 5.0) and the bloodstream (pH 7.4). The hydrolysis rates were measured by grinding polyketal 2 into a fine powder and adding it to deuterated solutions at pH 7.4 (phosphate buffer), pH 5.0 (acetate buffer), and pH 1.0 (DCl). The suspensions were stirred at 37° C. and data points were taken at 3 h, 24 h, 48 h, and 72 h. Each suspension was centrifuged for 4 min at 1800 g, and the supernatant was analyzed by $^1$H NMR. The spectra contained peaks for BDM (7.24 and 4.47 ppm) and acetone (2.05 ppm). The average of the two BDM peak integrals was used to determine the relative degree of hydrolysis. The percent hydrolysis was calculated as the BDM peak average of the pH 7.4 or 5.0 sample divided by the BDM peak average of the pH 1.0 control batch.

Exponential decay half-lives were calculated to be 102 h at pH 7.4 and 35 h at pH 5.0, representing a 3-fold rate increase from pH 7.4 to 5.0 (FIG. 4). The pH sensitivity of 2 is significantly less than that reported by Kwon, et al. (Kwon, Y. J.; Standley, S. M.; Goodwin, A. P.; Gillies, E. R.; Fréchet, J. M. J. Mol. Pharm. 2005, 2, 83-91) for a water-soluble ketal. We hypothesize that the lower pH sensitivity of 2 is due to its water insolubility, which limits the diffusion of water and creates another rate limiting step that is insensitive to pH. The diffusion kinetics of water into materials made of 2 will be dependent on the size of the particles and we would expect smaller particles to have greater pH sensitivity than ground particles.

Example 5

Synthesis of Micron Sized Particles

Compound 2 (from Example 4, supra) was also used to synthesize micron sized particles. An oil-in-water emulsion method (Panyam, J.; Williams, D.; Dash, A.; Leslie-Pelecky, D.; Labhasetwar, V. J. Pharm. Sci. 2004, 93, 1804-1814) was used to form the particles.

Briefly, 50 mg of 2 dissolved in 1 mL $CHCl_3$ (with 0.1% triethylamine) was added to 5 mL of 10 mM $NaHCO_3$ pH 9 buffer containing various amounts of polyvinyl alcohol (PVA, 31-50 kDa, Aldrich) as the emulsifier. The oil-water mixture was shaken briefly and then sonicated for 2 to 3 min at 40 watts (Branson Sonifier 250) to form a fine oil/water emulsion. The emulsion was stirred under $N_2$ flow for at least 3 h to evaporate the solvent and produce a particle suspension.

Particle sizes were analyzed by dynamic light scattering (DLS) and SEM. DLS samples were prepared by diluting the particle suspension in 10 mL pH 9 buffer and allowing the larger particles to settle out. An aliquot from the liquid portion of each vial was then diluted for DLS particle sizing (Brookhaven 90Plus particle sizer). An SEM sample was made with the 0.2:1 ratio of PVA:polyketal by centrifuging the particle suspension for 10 min (5000 g, 4° C.), washing with distilled water, and lyophilizing the recovered pellet.

As expected, the particle size was sensitive to the ratio of PVA to polyketal. The DLS particle diameters were 520 nm, 290 nm, and 280 nm for samples containing 0.2:1, 0.8:1, and 2:1 ratios of PVA:polyketal, respectively. The SEM images of the 0.2:1 batch (FIGS. 5A and 5B) confirm that the polyketal does form micron sized particles, with particle size distribution ranging from 0.5 to 30 µm in diameter.

Example 6

Synthesis and Characterization of Micelles and Polyketal Particles

Materials and Methods
Encapsulation of Dexamethasone in Polyketal Particle

The anti-inflammatory drug dexamethasone (Dex, Sigma) was encapsulated into particles made with polyketal 2. Dex-loaded particles were formulated using the same procedure as that described above, except that the oil phase contained a 5 mg/ml concentration of Dex and a 1:1 ratio of PVA:polyketal was used. SEM images of these particles demonstrate that they are 200-600 nm in diameter (FIG. 5C). Particle sizing by DLS indicated an effective diameter of 250 nm for the Dex-loaded particle batches. The Dex encapsulation efficiency ranged between 43-53%. Control batches were prepared with polyketal/PVA only and Dex only. To measure Dex encapsulation, each particle batch was re-suspended in pH 9 buffer, and an aliquot was then further diluted. A portion was filtered through a 0.1 □m Supor membrane Acrodisc syringe filter (Pall Corp.), and the 242 nm absorbance of the filtrate was recorded with a Shimadzu UV-1700 spectrophotometer. The encapsulation efficiency was calculated as $(A_{Dex}-A_{DexPoly})/(A_{Dex}-A_{Poly})$, where A is the absorbance at 242 nm and the subscripts 'Poly', 'Dex', and 'DexPoly' refer to the 'Polyketal only', 'Dex only', and 'Dex+Polyketal' samples, respectively. These calculations resulted in a Dex encapsulation efficiency of 43% to 53% for various samples.

Micelle Formation

FIG. 8 is a schematic representation showing peptide crosslinked micelle design and synthesis. Step 1: ISS DNA and I are mixed to form micelles (uncrosslinked micelle). Step 2: These micelles are then crosslinked with the antigenic peptide (II) to generate a delivery system that can encapsulate both immunostimulatory molecules and peptide antigens. After phagocytosis by APCs, the peptide-crosslinked micelles release their components.

An HIV peptide vaccine was synthesized using the PCM strategy with the peptide CGCRIQRGPGRAFVTIGKCGCG (II)(SEQ ID NO:4). The peptide II comes from the GP-120 protein and contains the sequence RIQRGPGRAFVTIGK (SEQ ID NO:5), which is both a class I and II antigen. First, micelles were formed between I and ISS-DNA by mixing 0.5 mg of I with 0.1 mg of ISS DNA (5-TCCATGACGTTCCT-GACGTT-3)(SEQ ID NO:6)(charge ratio was 1 to 15 (−/+)) in 0.5 ml of 50 mM PBS. Dynamic light scattering of these micelles using the Cumulants method indicated that they had an average diameter of 57.0 nm. These micelles were then crosslinked by adding 0.1 mg of II to the micelles (equal molar ratio of cysteines on II to thiopyridal groups on I). The peptide II was incorporated into the micelles through a disulfide exchange reaction.

FIG. 9 shows synthesis and characterization of PEG-polylysine thiopyridal. A. Synthesis of PEG-polylysine thiopyridal (I). 44 μmole of PEG-Poly-1-lysine (with PEG=5 kd and Poly-1-lysine=5,000) was dissolved in 1 ml of DMF, in a 5 ml round bottom flask, fitted with a stir bar (overnight stirring at room temperature was required to completely dissolve the polymer). 415 μmole of hydroxyl-ethyl thiopyridal acrylate and 58 μl of triethylamine were then added to the PEG-poly-1-lysine solution and the reaction was allowed to run for 24 hours at room temperature. The product was isolated by precipitating the reaction solution into 15 ml of ice cold diethyl ether. The yield was 88.2%. B. $^1$H-NMR spectrum of PEG-PLL-thiopyridal in $D_2O$. The product of A) was analyzed by $^1$H NMR in $D_2O$. The percentage of amines alkylated was determined by comparing the peak intensity ratio of pyridine protons (—NC$_5$H$_4$: δ=7.101 ppm, 7.629 ppm, 8.187 ppm) versus α, β, γ-methylene protons of poly-1-lysine (—CH$_2$CH$_2$CH$_2$: δ=1.122 ppm, 1.285 ppm, 1.553 ppm), this indicated that a 100% of the amines had been reacted. C./D. Dynamic light scattering analysis of PCMs uncross-linked (C) and peptide cross-linked (D). A 50 mM PBS buffer solution, at pH 7.4, containing 0.06 mg/ml of PEG-polylysine thiopyridal and 20 μg/ml of ISS DNA was made and filtered through a 200 nm syringe filter. This solution was then analyzed by dynamic light scattering (Zetasizer Nano ZS, Malvern Instruments), using the Cumulant method (C). This solution was then crosslinked by adding 0.12 mg of peptide antigen (II), after 3 hours of reaction the solution was analyzed by DLS as described above, the size and the size distribution of the crosslinked micelles are shown in D). E. Crosslinking reaction of cysteines on peptide anigen (II). F. UV analysis of crosslinking reaction between peptide anigen (II) and block copolymer micelles. Block copolymer micelles were formed between I and ISS DNA by mixing 0.5 mg of I with 0.1 mg of ISS DNA (representing a 15/1 amine to phosphate ratio), in 0.5 ml of 50 mM NaH$_2$PO$_4$ buffer (pH 7.4), in an eppendeorf tube. After incubation for 2 hours at room temperature, 0.1 mg of II (representing a 1:1 cysteine to thiopyridal ratio) was added to the micelles. The crosslinking reaction between the cysteines on II with the thiopyridal groups in the micelles was determined by UV analysis at 342 nm (representing the released thiopyridone). The percent of cysteine groups reacted was determined by the following formula:

$$\text{reacted peptide}(\%) = \frac{ABS_1 - ABS_2}{ABS_o} \times 100\%$$

where: $ABS_1$=UV absorption at 342 nm for the peptide-crosslinked micelles reaction (filled circles); $ABS_2$=UV absorption at 342 nm for the uncrosslinked micelles, without peptide (empty squares); $ABS_o$=UV absorption at 342 nm when all of the thiopyridone groups have been reacted (by addition of DTT) (empty circles).

FIG. 10 shows the effects of GSH on release of peptides and DNA. A. GSH sensitive peptide release. The stimuli responsive release of peptides from the PCMs due to the presence of GSH was investigated to determine if the PCMs will release peptide antigens after phagocytosis. The PCMs were incubated with different concentrations of GSH, for 24 hours in 50 mM pH 7.4 PBS buffer, and then analyzed by HPLC to determine the release of peptides. This figure demonstrates that the release of peptides is triggered by the presence of GSH. Incubation of the PCMs with 10 mM GSH (intracellular levels) induces the release of 71% of peptide, whereas incubation of the PCMs with just buffer causes the release of only 10% of peptides. B. GSH sensitive DNA release. The ability of the PCMs to protect encapsulated ISS-DNA from degradation by serum nucleases was investigated. PCMs were synthesized (as described above) and incubated with 10% serum for 12 hours, these PCMs were then examined by gel electrophoresis to determine the stability of the encapsulated ISS-DNA. As a control, ISS-DNA by itself was incubated with serum. This figure demonstrates that ISS-DNA, by itself, is completely hydrolyzed in 10% serum (Lane 2), in contrast ISS-DNA encapsulated in the PCMs is protected from serum nucleases, presumably because of the effects of the crosslinking (Lane 3), which should prevent nucleases from entering the micelle. C. ISS-DNA is protected from serum nucleases in the PCMs. A key advantage of the PCM strategy is that it generates a crosslinked delivery system. This crosslinking should stabilize the PCMs in vivo. The stability of the PCMs to decomposition was investigated by mixing the negatively charged polymer, poly(vinyl sulfate) (PVS) with the PCMs, this mixture was then analyzed by gel electrophoresis to determine the quantity of ISS-DNA displaced by the PVS. As a control, PVS was also incubated with uncrosslinked micelles that were just composed of II and ISS-DNA. Figure A, lane 4, demonstrates that PVS can disrupt uncrosslinked micelles that are just composed of ISS-DNA and II. In contrast, A, lane 5 demonstrates that PVS cannot displace ISS-DNA from the PCMs, presumably because the peptide crosslinking prevents the PVS from diffusing into the micelles and displacing the ISS-DNA. Importantly, after incubation of the PCMs with intracellular concentrations of GSH, the PCMs release encapsulated ISS-DNA, in the presence of PVS, demonstrating that the micelles should release their contents after phagocytosis. (lanes 2 and 3 in b)). Charge ratio of ISS-DNA to I is 1 to 15 (−/+); 1 μg of DNA was loaded in each lane; GSH (100 μM) was added to lane 3 to induce release of encapsulated ISS-DNA. All samples were incubated with 10% serum at room temperature for 12 h.

FIG. 11 depicts block copolymer micelles: A. Chemical structure of PEG-poly(Lysine-Thio-Pyridyl). PEG chain gives stability to the micelles, Polylysine segment is used for electrostatic interactions with proteins and DNA or RNA. Thiopyridal group is for subsequent crosslinking via a disulfide bond. B. Step 1: Mix PEG-poly(Lysine-thio-pyridal) with DNA and protein, form micelles, with PEG on the outside. C. Step 11: Crosslink micelles with a di-thiol containing molecule, such as di-thioethylene glycol. D. Crosslinked micelles are reduced by Glutathione, which has a much higher concentration in the cell than in the blood.

FIG. 12 shows the immunology of micelles. A. Uptake of SIINFEKL-CFSE (SEQ ID NO:1) micelles by human monocyte derived DCs. Human PBMC derived DCs (day 6 of culture) were pulsed with SIINFEKL/CFSE (SEQ ID NO:1) micelles for 4h in 37° C. at the concentration of 10 μg/ml, 5×10*5 cell/well, 96-U wells, RPMI/10% FCS. Cells were washed, fixed on the figures and prepared for confocal microscope imaging. B. Efficient uptake of micelle encapsulated SIINFEKL peptide (SEQ ID NO:1) by human monocyte derived DCs. Human PBMC derived DCs (day 6 of culture) were pulsed with SIINFEKL/CFSE (SEQ ID NO:1) plain (1) or micelle formulated (2,3) for 4h in 37° C. at the concentration of 10 μg/ml, 5×10*5 cell/well, 96-U wells, RPMI/10% FCS. Cells were washed, stained for CD11c and HLADR. Cells were gated for CD11c+, HLADR+ cells and analysed for CFSE fluorescence. C. Efficient uptake of micelle encapsulated SIINFEKL peptide (SEQ ID NO:1) by mouse DCs and Macrophages. Total mouse C57B1/6J FLT3-L splenocytes were pulsed with 1 or 10 μg/ml of CFSE labeled plain SIINFEKL (SEQ ID NO:1)(1) or micelle formulated peptide (2,3) for 4 hours (blue line), or remained untreated (red line) at 37° C. at the concentration 1×10*6 cell/well, 96-U wells, RPMI/10% FCS. Cells were stained for CD11c and CD11b and analyzed for CFSE positive fluorescence.

FIG. 13 is a bar graph showing that micelle formulated SIINFEKL peptide (SEQ ID NO:1) induces potent T cell responses in-vitro. Purified CD11c$^+$ cells from a syngeneic C57B1/6J H-2$^b$ FLT3-L treated mouse were pulsed for 4 hours with indicated concentrations and combinations of plain or micelle formulated SIINFEKL peptide (SEQID NO:1). Cells were washed and cocultured with total OT-1 splenocytes for 20h (left panel) or 96h (right panel). Cells were stained for CD8 and intracellular IFNγ and analyzed on a flow cytometer. Graphs represent: micelle SIINFEKL (SEQ ID NO:1)213.3 (black bar), micelle SIINFEKL (SEQ ID NO:1) 213.2 (grey bar), plain SIINFEKL (SEQ ID NO:1) (empty bar), medium (dotted bar) stimulated CD11c+DCs.

FIG. 14 shows the immunology of micelles. A. Efficient uptake of micelle encapsulated OVA protein by mouse DCs and Macrophages. Total mouse C57B1/6J FLT3-L splenocytes were pulsed with 1 or 10 μg/ml of FITC labeled plain ovalbumin (1) or micelle formulated protein (2) for 1 hour (black line), 5 hours (dotted line) or remained untreated (shaded). 37° C. at the concentration 1×10*6 cell/well, 96-U wells, RPMI/10% FCS. Cells were stained for CD11c and CD11b and analyzed for FITC positive fluorescence. B. Micelle encapsulated OVA/CpG activates DCs in-vitro. Total mouse C57B1/6J FLT3-L splenocytes were pulsed with 1 μg/ml of plain OVA (1) plain OVA+1 ug of CpG (2) or micelle formulated OVA (3) or micelle OVA+1 ug of CpG (4) for 24 hours. CD11c+ cells were analysed for and CD80 or CD86 markers. Data represent isotype control (shaded), untreated (grey line) or stimuli treated (black line) cells.

FIG. 15 is a graph depicting the immunology of polyketal particles. Uptake of polyketal particle (PKN) encapsulated U0126 by mouse DCs and Macrophages in-vitro. Total mouse C57B1/6J FLT3-L splenocytes were pulsed with 1 or 10 μg/ml of CMFDA labeled Polyketal Particle carrying U0126 ERK inhibitor for 5 hours at 37° C., 1×10*6 cell/well, 96-U wells, RPMI/10% FCS. Cells were stained for CD11c and CD11b and analyzed for CMFDA positive fluorescence. Data represent medium treated cells (shaded line) or 5 hours uptake (black line).

FIG. 16 is a schematic diagram showing the experimental outline for T cell stimulation in-vitro using OVA-OT/1 transgenic model.

FIG. 17 shows the immunology of micelles. A. Micelle formulated antigen induces potent T cell responses in-vitro. Purified CD11c$^+$ cells from a syngeneic C57B1/6J H-2$^b$ mouse were pulsed for 4 hours with indicated concentrations and combinations of ovalbumin and CpG plain or micelle formulated. Cells were washed and 1×10*5 of CD11c+ were cocultured with 1×10*6 of total OT-1 (SIINFEKL (SEQ ID NO:1)specific) splenocytes for 5 days. After 5 days cells were restimulated with a SIINFEKL peptide (SEQ ID NO:1)(1 ug/ml) with BFA (5 ug/ml) for 6 hours and stained for CD8 and intracellular IFNγ. Left panel represents the Flow Cytometer analysis; right panel shows the summary of the data. B. Micelle formulated antigens overcome CD4+ dependent mechanisms of CD8+ T cells induction. Purified CD11c$^+$ cells from a syngeneic C57B1/6J H-2$^b$ mouse were pulsed for 4 hours with indicated concentrations and combinations of ovalbumin and CpG plain or micelle formulated. Cells were washed and 1×10*5 of CD11c were cocultured with 5×10*5 of CD8+ MACS purified OT-1 splenocytes (purity of ~90%) for 5 days. After 5 days cells were restimulated with a SIINFEKL peptide (SEQ ID NO:1)(1 ug/ml) with BFA (5 ug/ml) for 6 hours and stained for CD8 and intracellular IFNγ. Left panel represents the Flow Cytometer analysis; right panel shows the summary of the data. C. Micelle formulated antigen activate DCs in-vivo. C57B1/6J mice (2/group) were injected i.v. with 5 μg/mouse of ovalbumin/CpG as plain or micelle formulated in 500 ul PBS. Spleens were harvested at 4 and 24 hours post injection, treated with collagenase (30 min/37 C), homogenized, and treated with erythrocyte lysis buffer. CD11c+ cells were stained for CD80 or CD86 markers and analyzed with a flow cytometer. Data represent isotype control (shaded), nontreated mouse (grey line) or antigen injected mouse (black line).

FIG. 18 shows the immunology of micelles and polyketal particles. A. Micelle formulated vaccines induce strong T cell responses in-vivo—CD8$^+$ IFNγ$^+$. Cohorts of 4 C57B1/6J mice were vaccinated s.c. with 5 μg/mouse of OVA (1) or OVA+CpG (2), micelle OVA (3), micelle OVA/CpG (4). Animals were boosted at day 36 (BOOST 1) and 84 (BOOST 2) using the same antigen formulations. Blood was harvested at days 6 post BOOST 2 and PBMCs were isolated using Histopaque gradient method, and restimulated with SIINFEKL peptide (SEQ ID NO:1) (1 ug/ml) and BFA (5 ug/ml) for 6 hours and stained for CD8 and intracellular IFNγ. Left panel represents the Flow Cytometry analysis and gating strategy for selected mice; right panel shows the summary of the data as a % of CD8$^+$ IFNγ$^+$ cells of total CD8$^+$ T cells. B. Micelle formulated vaccines induce strong T cell responses in-vivo— CD8$^+$ TNFα$^+$. Cohorts of 4 C57B1/6J mice were vaccinated s.c. with 5 μg/mouse of OVA (1) or OVA+CpG (2), micelle OVA (3), micelle OVA/CpG (4) micelle. Animals were boosted at day 36 (BOOST 1) and 84 (BOOST 2) using the same antigen formulations. Blood was harvested at days 6 post BOOST 2 and PBMCs were isolated using Histopaque gradient method. PBMCs from 4 mice were pooled and restimulated with SIINFEKL peptide (SEQ ID NO:1)(1 ug/ml) and BFA (5 ug/ml) for 6 hours and stained for CD8 and intracellular TNFα and IL-10. Left panel represents the Flow Cytometer analysis and gating strategy for selected mice; right panel shows the summary of the data as a % of CD8$^+$ TNFα⁺ cells of total CD8⁺ T cells. C. Kinetics of specific CD8⁺/IFNγ⁺ T cells after OVA/CpG vaccination. Cohorts of 4 C57B1/6J mice were vaccinated s.c. with 5 µg/mouse of OVA+CpG (grey line) and micelle OVA/CpG (blue line). Animals were primed at day 0 and boosted at day 36 (BOOST 1) and 84 (BOOST 2) using the same antigen formulations. Blood was harvested at distinct days post priming and boosts and PBMCs were isolated using Histopaque gradient method. PBMCs from 4 mice were restimulated with SIINFEKL peptide (SEQ ID NO:1)(1 ug/ml) and BFA (5 ug/ml) for 6 hours and stained for CD8 and intracellular IFNγ. Panels represent the summary of the data as % of CD8⁺ IFNγ⁺ cells of total CD8⁺ T cells including SEM error bars. D. Kinetics of specific CD8⁺/IFNγ⁺ T cells after OVA+U0126 PKN vaccination. Cohorts of 4 C57B1/6J mice were vaccinated s.c. with 5 µg/mouse of OVA (grey line) micelle OVA (blue line) and micelle OVA+10 ug U0126 PKN(red line). Animals were primed at day 0 and boosted at day 36 (BOOST 1) and 84 (BOOST 2) using the same antigen formulations. Blood was harvested at distinct days post priming and boosts and PBMCs were isolated using Histopaque gradient method. PBMCs from 4 mice were restimulated with SIINFEKL peptide (SEQ ID NO:1)(1 ug/ml) and BFA (5 ug/ml) for 6 hours and stained for CD8 and intracellular IFNγ. Panels represent the summary of the data as % of CD8⁺ IFNγ⁺ cells of total CD8⁺ T cells including SEM error bars. E. Micelle formulated vaccines induce strong antigen specific IgG antibody response in-vivo. Cohorts of 4 C57B1/6J mice were vaccinated s.c. with 5 µg/mouse of OVA (1) or OVA+CpG (2), micelle OVA (3), micelle OVA/CpG (4) micelle OVA+10 ug of PKN U0126 (5) or micelle OVA/CpG+10 ug of PKN U0126 (6). Animals were boosted at days 36 and 84 using the same antigen formulations. Bleedings were performed at week 4 post priming (PRIME), week 6 post 1$^{st}$ boost (BOOST 1) and week 7 post 2$^{nd}$ boost (BOOST 2). Sera from individual mice were pooled and tested for OVA specific IgG total, IgG1, IgG2a and IgG2b antibody reactivity using plate ELISA. Antibody reactivity was measured in 450 nm absorbance of serum serial dilution. Data are represented as a reciprocal of specific anti-OVA antibody. F. Micelle formulated vaccines induce antigen specific IgE and IgM antibody response in-vivo. Cohorts of 4 C57B1/6J mice were vaccinated s.c. with 5 µg/mouse of OVA (1) or OVA+CpG (2), micelle OVA (3), micelle OVA/CpG (4) micelle OVA+10 ug of PKN U0126 (5) or micelle OVA/CpG+10 ug of PKN U0126 (6). Animals were boosted at days 36 and 84 using the same antigen formulations. Bleeding was performed and week 7 post 2$^{nd}$ boost. Sera from individual mice were pooled and tested for OVA specific IgE and IgM antibody reactivity using plate ELISA. Antibody reactivity was measured in 450 nm absorbance of serum serial dilution. Data are represented as a reciprocal of specific anti-OVA antibody.

Polyketal PCADK Characterization

FIG. 19 shows polyketals from cyclohexane dimethanol A. Polyketals from cyclohexane dimethanol (termed PCADK) degrade into cyclohexane dimethanol and acetone, both have FDA approval for human use. B. PCADK degrades in an acid sensitive manner. The ketal linkages in PCADK hydrolyze on the order of weeks under physiologic pH conditions. The hydrolysis of the ketal linkages in PCADK were measured by H-NMR at the pHs of 4.5 and 7.4. At the phagosomal pH of 4.5, the ketal linkages of PCADK are approximately 30% hydrolyzed after 10 days. Based on this result, we anticipate that CAT-PKNs should be completely hydrolyzed, within 4-5 weeks after phagocytosis by macrophages.

FIG. 20 shows SEM images depicting that particles from PCADK can encapsulate the hydrophobic compounds and drugs such as rhodhamine red and ebselen.

FIG. 21 shows line graphs showing that release of rhodhamine red from PCADK is pH sensitive.

Synthesis and Characterization of Polyketals and Particles Thereof

FIG. 6 is a schematic representation showing the steps of particle formation. A. Step 1: Dissolve polyketal and drug into chloroform; dissolve polyvinyl alcohol in water. B. Step 2: Add chloroform solution to water and sonicate, generate micron sized droplets. Step 3: Let chloroform evaoporate, generates particles. P FIG. 7 shows polyketal particles loaded with Fluorescein are taken up in the liver. Murine liver tissue slice showing release of fluorescein from PKNs following intravenous injection.

FIG. 22 is a chemical representation showing that polyketals with almost any aliphatic diol can be made. The hydrophobicity of the polyketal determines its hydrolysis kinetics.

FIG. 23 is a photograph showing that FITC labeled polyketals are phagocytosed by liver macrophages. Phagocytosis of PKNs in vivo by Kupffer cells. Mice were injected with either FITC-PKNs or Empty PKNs. The livers of these mice were analyzed by histology. Left: FITC-PKNs are abundantly present in Kupffer cells, as evidenced by the punctate green fluorescence (100× magnification). Middle: empty PKNs generate very little background green fluorescence (100× magnification). Right: immunohistochemistry (IHC) for FITC (red) confirms uptake by Kupffer cells (400× magnification).

Figure 24B:
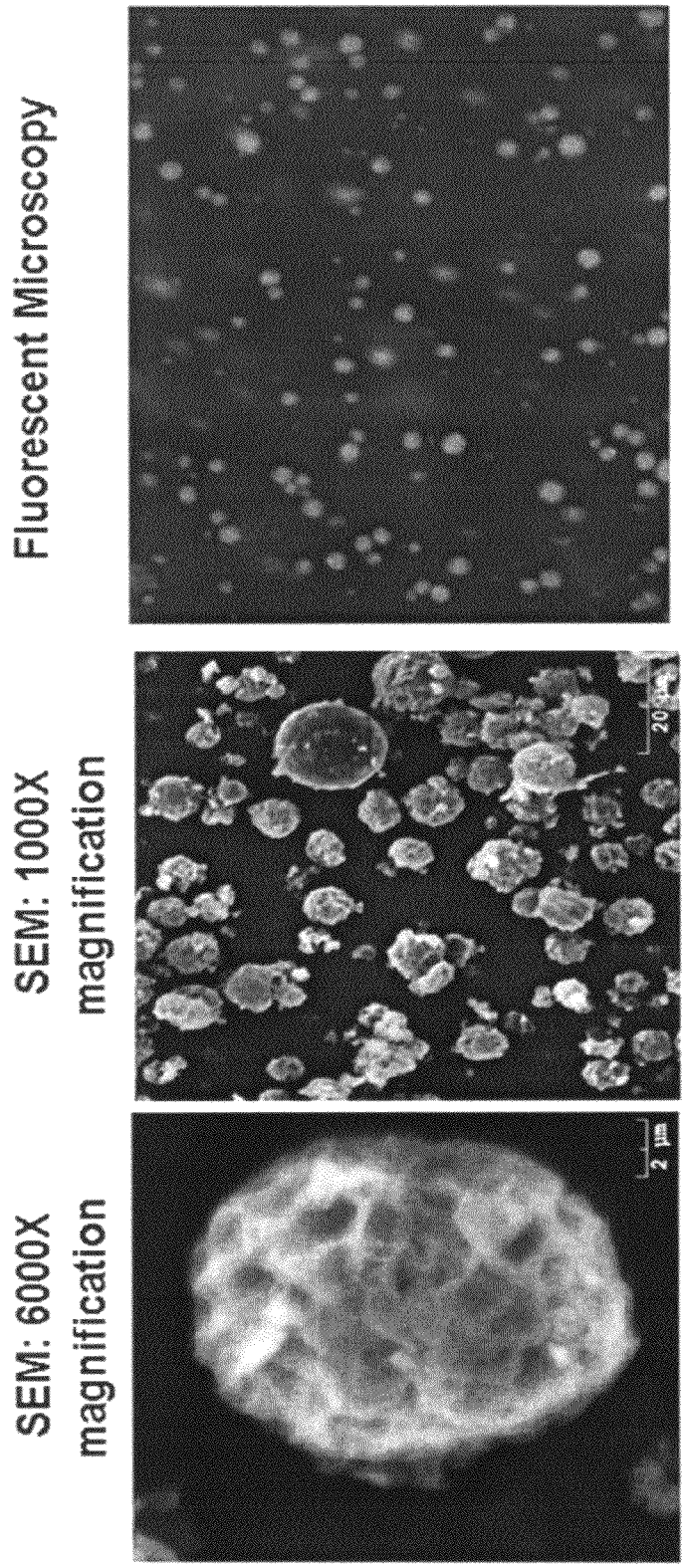
Figure 24C:
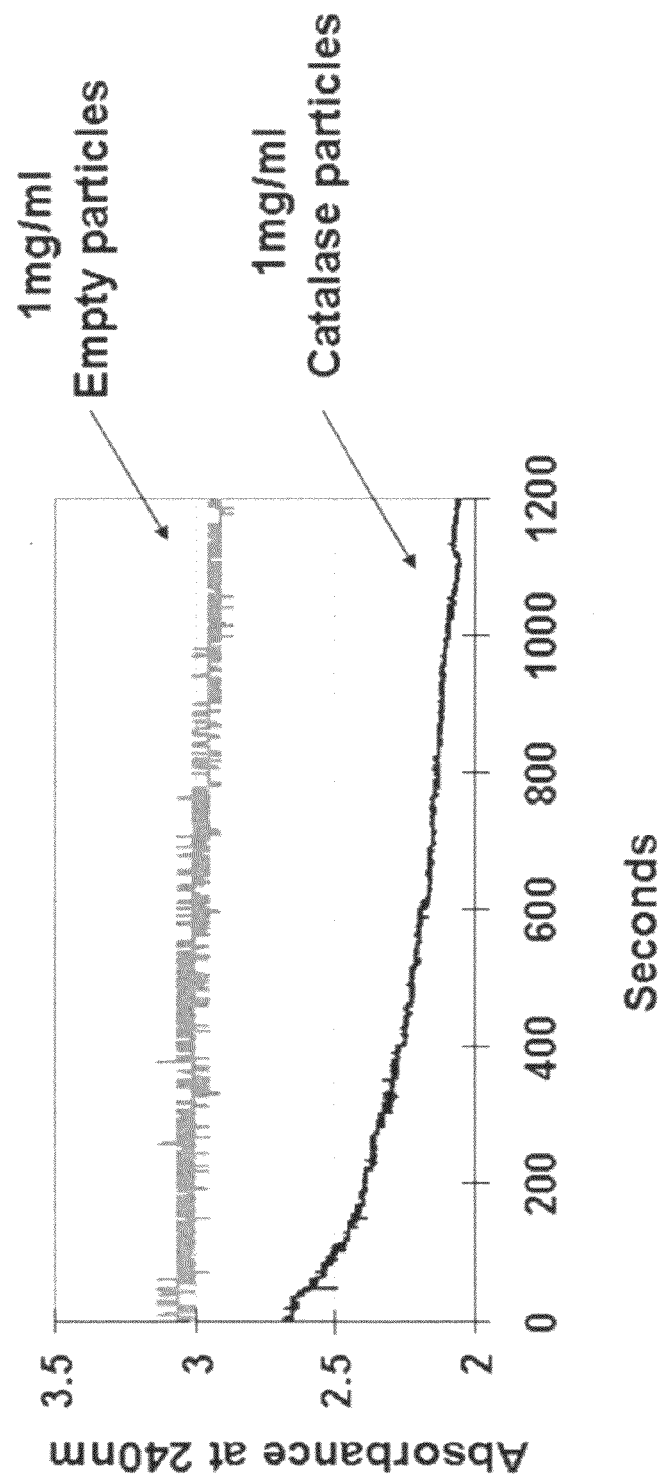

FIG. 24. A. Double emulsion procedure used to encapsulate catalase and super oxide dismutase in polyketal particles. A 50 µL aqueous solution of catalase (1 mg/ml) was dispersed into an organic phase, consisting of 75 mg of PCADK, dissolved in 1 mL of dichloromethane, using a homogenizer, generating a water in oil (w/o) emulsion. This w/o emulsion was then dripped into 25 mL of a 4% PVA solution, which was mechanically stirred with a homogenizer. The resulting w/o/w emulsion was then poured into 225 mL of a 4% PVA solution and mechanically stirred for several hours until the methylene chloride evaporated. The resulting particles were isolated by centrifugation, freeze-dried and examined by SEM (B) The protein encapsulation efficiency was 35%. The CAT-PKNs have an average diameter of approximately 8 microns. B. SEM image of catalase containing particles, and fluorescent microscope images of catalase containing particles. C. Catalase particles have enzymatic activity, as evidenced by their ability to decrease the absorbance at 240 nm of hydrogen peroxide.

REFERENCES FOR EXAMPLES 4-6

Ahsan, F.; Rivas, I. P.; Khan, M. A.; Torres-Suárez, A. I. *J. Controlled Release* 2002, 79, 29-40.

Prior, S.; Gander, B.; Blarer, N.; Merkle, H. P.; Subirá, M. L.; Irache, J. M.; Gamazo, C. *Eur. J. Pharm. Sci.* 2002, 15, 197-207.

Hahn, S. K.; Jelacic, S.; Maier, R. V.; Stayton, P. S.; Hoffman, A. S. *J. Biomater. Sci. Polymer Edn.* 2004, 15, 1111-1119.

Walter, E.; Dreher, D.; Kok, M.; Thiele, L.; Kiama, S. G.; Gehr, P.; Merkle, H. P. *J. Controlled Release* 2001, 76, 149-168.

van Apeldoorn, A. A.; van Manen, H.-J.; Bezemer, J. M.; de Bruijn, J. D.; van Blitterswijk, C. A.; Otto, C. *J. Am. Chem. Soc.* 2004, 126, 13226-13227.

Fu, K.; Pack, D. W.; Klibanov, A. M.; Langer, R. *Pharm. Res.* 2000, 17, 100-106.

Shenderova, A.; Burke, T. G.; Schwendeman, S. P. *Pharm. Res.* 1999, 16, 241-248.
Fife, T. H.; Jao, L. K. *J. Org. Chem.* 1965, 30, 1492-1495.
Kwon, Y. J.; Standley, S. M.; Goodwin, A. P.; Gillies, E. R.; Frechet, J. M. *J. Mol. Pharm.* 2005, 2, 83-91.
Murthy, N.; Campbell, J.; Fausto, N.; Hoffman, A. S.; Stayton, P. S. *Bioconjugate Chem.* 2003, 14, 412-419.
Murthy, N.; Xu, M.; Schuck, S.; Kunisawa, J.; Shastri, N.; Frechet, J. M. J. *Proc. Natl. Acad. Sci. U.S.A.* 2003, 100, 4995-5000.
Standley, S. M.; Kwon, Y. J.; Murthy, N.; Kunisawa, J.; Shastri, N.; Guillaudeu, S. J.; Lau, L.; Frechet, J. M. J. *Bioconjugate Chem.* 2004, 15, 1281-1288.
Gillies, E. R.; Goodwin, A. P.; Frechet, J. M. J. *Bioconjugate Chem.* 2004, 15, 1254-1263.
Lorette, N. B.; Howard, W. L. *J. Org. Chem.* 1960, 25, 521-525.
Panyam, J.; Williams, D.; Dash, A.; Leslie-Pelecky, D.; Labhasetwar, V. *J. Pharm. Sci.* 2004, 93, 1804-1814.

Example 7

Synthesis of Polyketal Copolymers and Formation of Particles

In this example a strategy is presented for manipulating the hydrolysis kinetics of poly(cyclohexane-1,4-diyl acetone dimethylene ketal) (PCADK) by controlling its hydrophilicity through copolymerization with other diols, of varying hydrophilicity. Six polyketal copolymers PK1 to PK6, based on PCADK, were synthesized.

Materials and Methods

Polyketal copolymers were synthesized in a 25 mL two-necked flask, connected to a short-path distilling head. The diols, 1,4-cyclohexanedimethanol (1.04 g, 7.25 mmol) and, either 1,4-butanediol, 1,5-pentanediol, 1,6-hexanediol, or 1,8-octanediol were dissolved in 20 mL of distilled benzene and kept at 100° C. Re-crystallized p-toluenesulfonic acid (5.5 mg, 0.029 mmol), dissolved in 550 μL of ethyl acetate, was added to the benzene solution. The ethyl acetate was distilled off, and distilled 2,2-dimethoxypropane (equal molar quantity as the two diols combined) was added to initiate the reaction. Additional doses of 2,2-dimethoxypropane (500 μL) and benzene (2 mL) were subsequently added to the reaction, every hour for 6 hours, via a metering funnel, to compensate for 2,2-dimethoxypropane and benzene that had distilled off. After 24 hours, the reaction was stopped by adding 100 μL of triethylamine. The polymer was isolated by precipitation into cold hexanes and analyzed by $^1$H-NMR and GPC, in general the resulting polymers had number average molecular weights between 2000 to 4000 Da. Table 1 lists the compositions and molecular weights of the polyketal copolymers synthesized. $^1$H NMR spectra were obtained using a Varian Mercury VX 400 MHz NMR spectrometer (Palo Alto, Calif.) using $CDCl_3$ as the solvent, the H-NMR spectra of the polyketal copolymers are summarized below, as a representative example, the $^1$H-NMR of PK3 is shown in FIG. 28. The molar ratio of 1,5-pentanediol to 1,4-cyclohexanedimethanol was obtained by obtaining the ratio of areas under the peaks a and b, respectively.

PK1. $^1$H NMR ($CDCl_3$) δ=3.4-3.18 (m, 4H), 1.66 (s, 1.9H), 1.85-0.93 (m, 8H), and 1.32 (s, 6H).
PK2. $^1$H NMR ($CDCl_3$) δ=3.4-3.18 (m, 4H), 1.66 (s, 1.8H), 1.85-0.93 (m. 8H), and 1.32 (s, 6H).
PK3. $^1$H NMR ($CDCl_3$) δ=3.4-3.18 (m, 4H), 1.64 (s, 1.7H), 1.85-0.93 (m, 8.2H), and 1.32 (s, 6H).
PK4. $^1$H NMR ($CDCl_3$) δ=3.4-3.18 (m, 4H), 1.68 (s, 2H), 1.85-0.93 (m, 8H), and 1.32 (s, 6H).
PK5. $^1$H NMR ($CDCl_3$) δ=3.4-3.18 (m, 4H), 1.67 (s, 1.8H), 1.85-0.93 (m, 8H), and 1.32 (s, 6H).
PK6. $^1$H NMR ($CDCl_3$) δ=3.4-3.18 (m, 4H), 1.68 (s, 1.8H), 1.85-0.93 (m, 8H), and 1.32 (s, 6H).

The molecular weight of the polyketal copolymers was determined by gel permeation chromatography (GPC) using a Shimadzu system (Kyoto, Japan) equipped with a UV detector. THF was used as the mobile phase at a flow rate of 1 mL/min. Polystyrene standards (Peak Mw=1060, 2970, and 10680) from Polymer Laboratories (Amherst, Mass.) were used to establish a molecular weight calibration curve. The hydrolysis of the polyketal copolymers was measured in buffered water at pH values of 1.0 (0.1M HCL), 4.5 (100 mM AcOH) and 7.4 (100 mM) at 37° C. Briefly, 20 mg of the polymer samples were placed in a 5 ml vial, 1 mL of buffer solution was added to each vial, and mixed with a magnetic stir bar. At specific time points, 1 mL of $CDCl_3$ was added to each vial and shaken vigorously, the $CDCl_3$ phase was isolated and analyzed by $^1$H NMR, to determine the percent hydrolysis the of ketal linkages in polyketal copolymer.

Results and Discussion

Six polyketal copolymers PK1-PK6 (Table 1, infra), based on PCADK, were synthesized using the acetal exchange reaction. The copolymers of PCADK were synthesized by copolymerizing 1,4-cyclohexanedimethanol with either butanediol, pentanediol, hexanediol, and octanediol. The hydrophilicity of these diols are different from that of 1,4-cyclohexanedimethanol (log P=1.46), as evidenced by their respective log P values (Table 2, infra). FIG. 29 shows a synthetic scheme of the acetal-exchange reaction used to make the polyketals and the degradation products generated from their hydrolysis. The synthesis of all the polyketal copolymers was accomplished in one step, on a multi-gram scale, and with yields of 50-60%. In general, the introduction of diols other than CDM did not cause any complications in the synthesis, and procedures developed for the synthesis of PCADK were suitable for the synthesis of the copolymers. Importantly, all the copolyketals synthesized were crystalline, and therefore have the potential for formulation into microparticles.

TABLE 1

Compositions and molecular weight of polyketal copolymers synthesized.

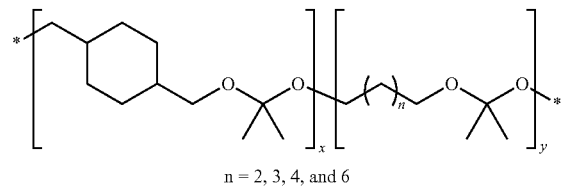

n = 2, 3, 4, and 6

| Polymer ID | Polymer composition | | $M_n$ | DPI |
|---|---|---|---|---|
| | Monomer A | Monomer B | | |
| PK1 | 1,4-cyclohexanedimethanol (x = 98.03%) | 1,5-pentanediol (y = 1.93%) | 2149 | 1.742 |
| PK2 | 1,4-cyclohexanedimethanol (x = 92.46%) | 1,5-pentanediol (y = 7.56%) | 2530 | 1.629 |
| PK3 | 1,4-cyclohexanedimethanol (x = 86.70%) | 1,5-pentanediol (y = 13.30%) | 2596 | 1.432 |
| PK4 | 1,4-cyclohexanedimethanol (x = 96.75%) | 1,4-butanediol (y = 3.25%) | 2637 | 1.553 |
| PK5 | 1,4-cyclohexanedimethanol (x = 85.32%) | 1,6-hexanediol (y = 14.68%) | 2122 | 1.538 |

TABLE 1-continued

Compositions and molecular weight of polyketal copolymers synthesized.

[structure shown with n = 2, 3, 4, and 6]

| Polymer | Polymer composition | | $M_n$ | DPI |
|---|---|---|---|---|
| ID | Monomer A | Monomer B | | |
| PK6 | 1,4-cyclohexanedimethanol (x = 87.31%) | 1,8-octanediol (y = 12.69%) | 2181 | 1.786 |

Figure 30B:
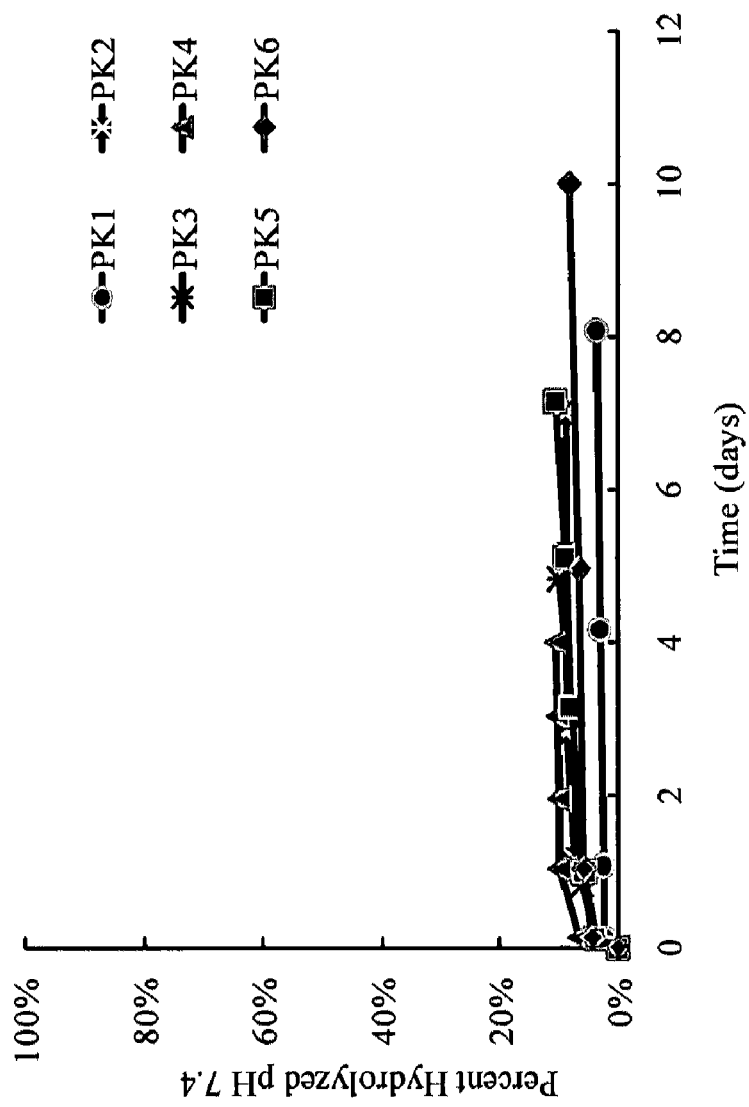

The hydrolysis kinetics of PK1 to PK6 was measured at the pH values of 4.5 and 7.4 to determine their behavior in the acidic environment of phagosomes and in the blood. FIG. 30 demonstrates that all polyketal copolymers undergo acid-catalyzed hydrolysis and that their hydrolysis kinetics scale inversely with their hydrophobicity. PK1, PK2, and PK3 were copolymers synthesized from 1,4-cyclohexanedimethanol and 1,5-pentanediol. Their hydrophilicity scales with their 1,5-pentanediol content, due to the large difference in hydrophobicity between 1,5-pentanediol and 1,4-cyclohexanedimethanol, their respective Log P values are 0.27 and 1.46. FIG. 30A demonstrates that 1,5-pentanediol dramatically accelerates the pH 4.5 hydrolysis kinetics of 1,4-cyclohexanedimethanol based polyketals. For example, only 30% of PK1, a copolymer containing 2% pentanediol, was hydrolyzed after 10 days at pH 4.5. On the other hand, at the same pH condition PK2, which contains 7.5% pentanediol, was 75% hydrolyzed after 7 days, and PK3, containing 13% pentanediol, was 50% hydrolyzed after 2 days and completely hydrolyzed after 5 days. For all three polyketals, less than 15% of the polymers were hydrolyzed in pH 7.4 within the duration of the experiments (FIG. 30B).

To determine if this was a broader phenomenon, extending beyond copolymers of pentane diol, polyketal copolymers PK4, PK5, and PK6 were also synthesized from butanediol, hexanediol, and octanediol, which have differing hydrophobicity from pentanediol, and their hydrolysis kinetics were investigated. Table 2 demonstrates that this set of copolymers also has an inverse relationship between hydrophobicity and hydrolysis kinetics. For example, PK4, a copolymer synthesized using 1,4-cyclohexanedimethanol and 1,4-butanediol, has the faster hydrolysis kinetics of all the copolyketals synthesized, having a hydrolysis half-life of 1 day at pH 4.5, which is predicted based on the hig hydrophilicity of butanediol in comparison to the other diols. On the other hand, PK6, synthesized using 1,4-cyclohexanedimethanol and a more hydrophobic monomer, 1,8-octanediol, had a pH 4.5 hydrolysis half-life of 18.6 days. In summary, these data demonstrate that the hydrolysis kinetics of polyketals can be tuned by varying their hydrophobicity and suggests that diffusion of water into the polyketals is the rate determining step governing hydrolysis. Importantly, the hydrolysis kinetics of all the polyketal copolymers was pH sensitive; in general they hydrolyzed at least one order of magnitude faster at pH 4.5 than at pH 7.4.

One of the polyketal copolymers synthesized (termed PK3 in Table 1), consisting of cyclohexane-dimethanol and pentane diol, had a hydrolysis half life of 2 days at pH 4.5 but several weeks at pH 7.4. This polyketal may be useful for delivering therapeutic drugs to a subject because it should hydrolyze rapidly after phagocytosis; however it is relatively stable at physiological pH. Additionally, PK3 may be suitable for microparticle drug delivery because of its rapid hydrolysis kinetics and biocompatible degradation products, which are 1,5-pentanediol, 1,4-cyclohexanedimethanol, and acetone.

To further the study of using PK3 for delivery of drug therapies, microparticles were formulated from PK3 using a solvent evaporation procedure. FIG. 31 demonstrates that microparticles can be formed with PK3, and that the particles have a size between 1-5 microns, which suitable for phagocytosis by macrophages. Thus, therapeutic drugs may be encapsulated into PK3 microparticles (for example by using

TABLE 2

Hydrolysis half-lives of polyketal copolymers at pH 4.5 and pH 7.4, at 37° C.

| PK ID | Polymer composition | | | | Half life at pH 4.5 | Estimated half life at pH 7.4 | Log P of diol B |
|---|---|---|---|---|---|---|---|
| | Diol A | Percent diol A | Diol B | Percent diol B | | | |
| PK4 | | 96.75% | 1,4-butanediol | 3.25% | 1.0 day | 54 days | −0.83 |
| PK3 | 1,4-cyclohexane dimethanol | 86.70 | 1,5-pentanediol | 13.30% | 1.8 days | 39 days | 0.27 |
| PK5 | | 85.32% | 1,6-hexanediol | 14.68% | 4.4 days | 53 days | 0.76 |
| PK6 | | 87.31% | 1,8-octanediol | 12.69% | 18.6 days | 360 days | 1.75 | a water/oil/water double emulsion procedure or other method) for administration into a subject.

Microparticles loaded with active agents will be formulated from the polyketal copolymers using a modified water/oil/water emulsion method (Ando et al., *Journal of Pharmaceutical Sciences* 1999, 88, 126-130). For example, PK3 (100 mg) will be dissolved in 1 mL of dichloromethane, in a separate vial, 40 mg of the active agent will be dissolved in 400 µL of D.I. water. The aqueous solution of the active agent will be mixed with the PK3 solution, and sonicated for 60 seconds (Misonix Incorporated, Farmigdale, N.Y.). The sonicated mixture will then immersed in liquid nitrogen for 15 sec, and 12 mL of a 5% w/w PVA solution (pH 7.45) will be added to it. This mixture will be homogenized for 120 seconds with a Powergen 500 homogenizer (Fisher Scientific, Waltham, Mass.), and then transferred to a beaker containing 40 mL of 1% w/w PVA (pH 7.45). This solution will then be stirred for 3 hours with a magnetic stir bar to evaporate the organic solvent. The particles will be isolated by centrifuging at 10,000 rmp for 15 min, washed twice with 15 mL of PBS buffer and freeze dried.

REFERENCES FOR EXAMPLE 7

Cordes, E. H.; Bull, H. *Chemical Reviews* 1974, 74, 581.
Gopferich, A. *Biomaterials* 1996, 17, 103.
Gopferich, A.; Tessmar, J. *Advanced Drug Delivery Reviews* 2002, 54, 911.
Kumar, N.; Langer, R. S.; Domb, A. *J. Advanced Drug Delivery Reviews* 2002, 54, 889.

Example 8

Formation of Particles with Linkers

In this example, a polyketal molecule of the invention was modified with a linker that can bind an active agent. Specifically, a nitrilotriacetic acid (NTA) linker was added to PCADK. The NTA linker, when loaded with nickel (Ni) allowed the binding of histidine-tagged proteins (FIG. 32). The modified PCADK then formed microspheres ideal for rapid delivery of active agents (e.g. growth factors) (FIG. 33).

Materials and Methods
Synthesis of PCADK Particles with NTA Linker

PCADK was synthesized as previously described above (see also Lee S et al. Polyketal microparticles: a new delivery vehicle for superoxide dismutase. Bioconjug Chem. 2007 January-February; 18(1):4-7 and Heffeman M J and Murthy N. Polyketal nanoparticles: a new pH-sensitive biodegradable drug delivery vehicle. Bioconjug Chem. 2005 November-December; 16(6):1340-2, herein incorporated by reference).

After synthesis of the polyketal, 90 mg of PCADK was dissolved in 1 mL of a 10 mg/mL solution of DOGS-NTA (Avanti Polar Lipids) in dichloromethane (final concentration of 10% DOGS-NTA). To ensure solubility, the mixture was sonicated for several seconds/minutes in a water bath sonicator. The polymer solution was then poured into a vial containing 5 mL of PVA (2%) and homogenized for 60 seconds. The resulting solution was stirred over 40 mL of 0.5% PVA for 4-6 hours. The particles were then spun down and washed several times in deionized water and frozen in liquid nitrogen for lyophilization. The resulting freeze-dried particles were imaged using SEM and shown in FIG. 34.

Nickel loading of PCADK-NTA

In order to get particles capable of binding to His-tagged proteins, particles needed to be loaded with nickel. Thus, particles were incubated with 50 mM $NiCl_2$ at 10 mg/mL and agitated for 2 hours at room temperature. To determine nickel uptake, we incubated the particles overnight with $NiCl_2$, spun down the particles, and measured the unbound nickel in the supernatant spectrophotometrically. As the data in FIG. 35 demonstrate, at varying NTA loading there was a decrease in free nickel in the solution, indicating the particles had been loaded with nickel.

Binding of His-Tagged Proteins to PCADK-NiNTA

To determine if NiNTA on particles was capable of binding His-tagged proteins, varying concentrations of His-GFP were incubated with PCADK-NiNTA (1% solution w/v) overnight at 4 degrees Celsius. Particles were centrifuged out and washed several times in PBS before resuspension for analysis. FIG. 36 is a representative fluorescent stain for GFP that was converted to grayscale for presentation. As the image shows, the particles retained GFP on their surface. To further quantify the amount of His-GFP bound, particles were loaded with increasing amounts of His-GFP, washed several times, and ELISA was run on the particles to determine levels of binding. As the data in FIGS. 37 (1% NTA) and 38 (10% NTA) show, PCADK-NiNTA dose-dependently bound the His-tagged protein. At 1% NTA, the particles saturated binding at a loading of 60 ng His-GFP, while at 10% NTA, saturation was reached at 120 ng His-GFP loading. At most points in the linear range, binding was roughly 50% efficient. The data in FIG. 40 shows that the percent binding of His-GFP increases with the amount of NTA. FIG. 41 shows that His-GFP binding to NTA is stable for at least 15 hours.

To determine if the binding was reversible, various NTA concentration His-GFP-loaded particles were incubated with imidazole (200 mM), a competitive agent for the Ni-NTA complex. Supernatants were collected at various time points and assayed for GFP fluorescence. As the data in FIG. 39 demonstrate, the His-GFP was released from the particles rather rapidly, with most of the protein released at 30 minutes. This suggests that the protein is not irreversibly bound to the particle and should have good bioavailability.

What is claimed is:
1. A biodegradable hydrophobic polyketal polymer comprising ketal groups, wherein each ketal group of the polymer has two oxygen atoms within the polymer backbone, wherein the polyketal polymer is selected from a group consisting of:
   a. a polyketal polymer comprising 1,4,-cyclohexanedimethoxy and 1,5-pentanedioxy, wherein the polyketal polymer comprising 1,4,-cyclohexanedimethoxy and 1,5-pentanedioxy is a poly(cyclohexane-1,4-diyl acetone dimethylene ketal-co-1,5-pentane-acetone dimethylene ketal);
   b. a polyketal polymer comprising 1,4,-cyclohexanedimethoxy and 1,4-butanedioxy, wherein the polyketal polymer comprising 1,4,-cyclohexanedimethoxy and 1,4-butanedioxy is a poly(cyclohexane-1,4-diyl acetone dimethylene ketal-co-1,4-butane-acetone dimethylene ketal);
   c. a polyketal polymer comprising 1,4,-cyclohexanedimethoxy and 1,6-hexanedioxy, wherein the polyketal polymer comprising 1,4,-cyclohexanedimethoxy and 1,6-hexanedioxy is a poly(cyclohexane-1,4-diyl acetone dimethylene ketal-co-1,6-hexane-acetone dimethylene ketal; and
   d. a polyketal polymer comprising 1,4,-cyclohexanedimethoxy and 1,8-octanedioxy, wherein the polyketal polymer comprising 1,4,-cyclohexanedimethoxy and 1,8-octanedioxy is a poly(cyclohexane-1,4-diyl acetone dimethylene ketal-co-1,8-octane-acetone dimethylene ketal).

2. The polymer of claim 1, further comprising a linker.

3. The polymer of claim 2, wherein the linker is streptavidin, RDG, GST, ssDNA, hemoglobin, an amino acid sequence, an antibody, a polycarboxylic acid and/or a chelating agent.

4. The polymer of claim 2, wherein the linker binds a protein, peptide and/or carbohydrate.

5. The polymer of claim 4, wherein the protein, peptide and/or carbohydrate comprises a histidine tag.

6. The polymer of claim 4, wherein said protein is a therapeutic, prophylactic or diagnostic protein.

7. The polymer of claim 4, wherein said protein, peptide, and/or carbohydrate is a growth factor, cytokine, antioxidant enzyme, or antibody.

8. A biodegradable particle comprising
   (a) a biodegradable hydrophobic polyketal polymer comprising ketal groups, wherein each ketal group of the polymer has two oxygen atoms within the polymer backbone, wherein the polyketal polymer is selected from a group consisting of:
      i. a polyketal polymer comprising 1,4,-cyclohexanedimethoxy and 1,5-pentanedioxy, wherein the polyketal polymer comprising 1,4,-cyclohexanedimethoxy and 1,5-pentanedioxy is a poly(cyclohexane-1,4-diyl acetone dimethylene ketal-co-1,5-pentane-acetone dimethylene ketal);
      ii. a polyketal polymer comprising 1,4,-cyclohexanedimethoxy and 1,4-butanedioxy, wherein the polyketal polymer comprising 1,4,-cyclohexanedimethoxy and 1,4-butanedioxy is a poly(cyclohexane-1,4-diyl acetone dimethylene ketal-co-1,4-butane-acetone dimethylene ketal);
      iii a polyketal polymer comprising 1,4,-cyclohexanedirnethoxy and 1,6-hexanedioxy, wherein the polyketal polymer comprising 1,4,-cyclohexanedimethoxy and 1,6-hexanedioxy is a poly(cyclohexane-1,4-diyl acetone dimethylene ketal-co-1,6-hexane-acetone dimethylene ketal); and
      iv. a polyketal polymer comprising 1,4,-cyclohexanedimethoxy and 1,8-octanedioxy, wherein the polyketal polymer comprising 1,4,-cyclohexanedimethoxy and 1,8-octanedioxy is a poly(cyclohexane-1,4-diyl acetone dimethylene ketal-co-1,8-octane-acetone dimethylene ketal), and
   (b) a linker.

9. The particle of claim 8, wherein the linker binds a protein, peptide and/or carbohydrate.

10. A composition comprising
   a. a biodegradable hydrophobic polyketal polymer comprising ketal groups, wherein each ketal group of the polymer has two oxygen atoms within the polymer backbone, wherein the polyketal polymer is selected from a group consisting of:
      i. a polyketal polymer comprising 1,4 ,-cyclohexanedimethoxy and 1,5-pentanedioxy, wherein the polyketal polymer comprising 1,4,-cyclohexanedimethoxy and 1,5-pentanedioxy is a poly(cyclohexane-1,4-diyl acetone dimethylene ketal-co-1,5-pentane-acetone dimethylene ketal);
      ii. a polyketal polymer comprising 1,4,-cyclohexanedimethoxy and 1,4-butanedioxy, wherein the polyketal polymer comprising 1,4,-cyclohexanedimethoxy and 1,4-butanedioxy is a poly(cyclohexane-1,4-diyl acetone dimethylene ketal-co-1,4-butane-acetone dimethylene ketal);
      iii. a polyketal polymer comprising 1,4,-cyclohexanedimethoxy and 1,6-hexanedioxy, wherein the polyketal polymer comprising 1,4,-cyclohexanedimethoxy and 1,6-hexanedioxy is a poly(cyclohexane-1,4-diyl acetone dimethylene ketal-co-1,6-hexane-acetone dimetylene ketal); and
      iv. a polyketal polymer comprising 1,4,-cyclohexanedimethoxy and 1,8-octanedioxy, wherein the polyketal polymer comprising 1,4,-cyclohexanedimethoxy and 1,8-octanedioxy is a poly(cyclohexane-1,4-diyl acetone dimethylene ketal-co-1,8-octane-acetone dimethylene ketal),
   b. a linker, and
   c. a protein, peptide and/or carbohydrate attached to the linker.

11. The composition of claim 10, wherein the linker is streptavidin, RDG, GST, ssDNA, hemoglobin, an amino acid sequence, an antibody, a polycarboxylic acid and/or a chelating agent.

12. A biodegradable particle comprising
   (a) a biodegradable hydrophobic polyketal polymer comprising ketal groups, wherein each ketal group of the polymer has two oxygen atoms within the polymer backbone, wherein the polyketal polymer is selected from a group consisting of:
      i. a polyketal polymer comprising 1,4,-cyclohexanedimethoxy and 1,5-pentanedioxy, wherein the polyketal polymer comprising 1,4,-cyclohexanedimethoxy and 1,5-pentanedioxy is a poly(cyclohexane-1,4-diyl acetone dimethylene ketal-co-1,5-pentane-acetone dimethylene ketal);
      ii a polyketal polymer comprising 1,4,-cyclohexanedimethoxy and 1,4-butanedioxy, wherein the polyketal polymer comprising 1,4,-cyclohexanedimethoxy and 1,4-butanedioxy is a poly(cyclohexane-1,4-diyl acetone dimethylene ketal-co-1,4-butane-acetone dimethylene ketal);
      iii. a polyketal polymer comprising 1,4,-cyclohexanedimethoxy and 1,6-hexanedioxy, wherein the polyketal polymer comprising 1,4,-cyclohexanedimethoxy and 1,6-hexanedioxy is a poly(cyclohexane-1,4-diyl acetone dimethylene ketal-co-1,6-hexane-acetone dimethylene ketal); and iv. a polyketal polymer comprising 1,4,-cyclohexanedimethoxy and 1,8-octanedioxy, wherein the polyketal polymer comprising 1,4,-cyclohexanedimethoxy and 1,8-octanedioxy is a poly(cyclohexane-1,4-diyl acetone dimethylene ketal-co-1,8-octane-acetone dimethylene ketal); and (b) an active agent selected from a group consisting of a protein, peptide, carbohydrate, nucleic acids, or small molecules.

* * * * *